US006812225B2

(12) United States Patent
Pierson et al.

(10) Patent No.: US 6,812,225 B2
(45) Date of Patent: Nov. 2, 2004

(54) THERAPEUTIC HETEROCYCLIC COMPOUNDS

(75) Inventors: Edward Pierson, Wilmington, DE (US); Daniel Sohn, Sodertalje (SE); Markus Haeberlein, Sodertalje (SE); Timothy Davenport, Wilmington, DE (US); Marc Chapdelaine, Wilmington, DE (US); Carey Horchler, Wilmington, DE (US); John P. McCauley, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 11 days.

(21) Appl. No.: 10/051,776

(22) Filed: Jan. 16, 2002

(65) Prior Publication Data
US 2003/0013708 A1 Jan. 16, 2003

Related U.S. Application Data
(60) Provisional application No. 60/262,107, filed on Jan. 16, 2001.

(51) Int. Cl.[7] .................. A61K 31/37; A61K 31/38; A61K 31/35; C07D 335/04; C07D 311/04
(52) U.S. Cl. .................. 514/183; 514/456; 514/430; 549/23; 549/362; 549/396; 549/406; 549/407
(58) Field of Search .................. 514/183, 430, 514/456; 549/23, 362, 396, 406, 407

(56) References Cited

U.S. PATENT DOCUMENTS

| | | | |
|---|---|---|---|
| 3,862,143 A | 1/1975 | Klutchko et al. | |
| 3,937,837 A | 2/1976 | Klutchko et al. | |
| 4,189,498 A | 2/1980 | Kabbe et al. | |
| 4,307,020 A | 12/1981 | Kabbe et al. | |
| 5,112,856 A | 5/1992 | Gaginella et al. | |
| 5,171,865 A | 12/1992 | Kurono et al. | |
| 5,403,842 A | 4/1995 | Leonardi et al. | |
| 5,605,896 A | 2/1997 | Leonardi et al. | |
| 5,914,401 A | 6/1999 | Egle et al. | |
| 5,965,575 A | 10/1999 | Peglion et al. | |
| 5,968,954 A | 10/1999 | Peglion et al. | |
| 6,034,256 A | * 3/2000 | Carter et al. | .................. 549/456 |
| 6,153,625 A | 11/2000 | Peglion et al. | |
| 6,552,054 B1 | 4/2003 | Yasuma et al. | |

FOREIGN PATENT DOCUMENTS

| | | |
|---|---|---|
| DE | 2331138 A | 1/1974 |
| EP | 0000377 | 1/1979 |
| EP | 0017578 | 10/1980 |
| EP | 0104018 A2 | 3/1984 |
| EP | 0546389 | 6/1993 |
| GB | 2177084 | 1/1987 |
| JP | 2001-261657 | 9/2001 |
| WO | WO 9109853 | 7/1991 |
| WO | 9429293 | * 12/1994 |
| WO | WO 9734883 | 9/1997 |
| WO | WO 9827058 | 6/1998 |
| WO | WO 9827080 | 6/1998 |
| WO | WO 99/05140 | 2/1999 |
| WO | WO 9914207 | 3/1999 |
| WO | WO 9914212 | 3/1999 |
| WO | WO 9914213 | 3/1999 |
| WO | WO 0012623 | 3/2000 |
| WO | WO 00/40554 | 7/2000 |
| WO | WO 01/16127 | 3/2001 |
| WO | WO 01/161127 | 3/2001 |

OTHER PUBLICATIONS

Gaster et al,J. Med. Chem.41, 1218–35(1998).*
CAPLUS 128:265746, also cited as Berg et al, J. Med. Chem. Behavioral and Biochem. Pharmacology & Mol. Chgem. 41/11, 1934–42 1998.*
CAPLUS DN 122:314453, also cioted as WO 9429293.*
PCT Written Opinion PCT/SE02/00070.
PCT Written Opinion PCT/SE02/00069.
PCT Written Opinion PCT/SE02/00068.
International Search Report for International Application No. PCT/SE02/00070.
International Search Report for International Application No. PCT/SE02/00069.
International Search Report for International Application No. PCT/SE02/00068.
Chemistry Letters 1997, Raposo et al, "The Effect of Chromenone Receptors on the Selectivity of the Reaction between Pyrrolidine and 5–Hydroxymethyl–2–(5H)–Furanone", pp 173–174.
Journal of Medicinal Chemistry, Clitherow et al, "Evolution of a Novel Series of . . . Antagonists", vol. 37, No. 15, pp 2253–2257.

(List continued on next page.)

Primary Examiner—Richard L. Raymond
Assistant Examiner—Sudhaker B. Patel
(74) Attorney, Agent, or Firm—George A. Gilbert

(57) ABSTRACT

Provided herein is a compound having the formula (I):

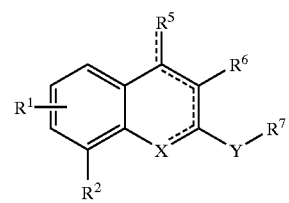

Wherein said compounds are useful for the treatment of psychiatric disorders including but not limited to depression, generalized anxiety, eating disorders, dementia, panic disorder, and sleep disorders. The compounds may also be useful in the treatment of gastrointestinal disorders, cardiovascular regulation, motor disorders, endocrine disorders, vasospasm and sexual dysfunction. The compounds are $5HT_{1B}$ and $5HT_{1D}$ antagonists.

9 Claims, No Drawings

OTHER PUBLICATIONS

Gaster, et al., "The Selective 5-HT$_{1B}$ Receptor Inverse Agonist 1'-Methyl-5-[[2'-methyl-4'-(5-methyl-1,2,4-oxadiazol-3-yl)biphenyl-4-yl]carbonyl]-2,3,6,7-tetrahydrospiro[furo[2,3-f]indole-3,4'-piperidine] (SB-224289) Potently Blocks Terminal 5-HT Autoreceptor Function Both in Vitro and in Vivo" *J. Med. Chem.*, 41, 1218–1235 (1998).

Russell, et al., "3-[3-(Piperidin-1-yl)propyl]indoles as Highly Selective h5-HT$_{1D}$Receptor Agonists", *J. Med. Chem.*, 42, 4981–5001, (1999).

Barnes, et al., "A review of central 5-HT receptors and their function", *Neuropharmacology* 38, 1083–1152, (1999).

Massot, et al., "5-HT 1B Receptors: A Novel Target for Lithium", *Neuropsychopharmacology* vol. 21, No. 4, 530–541.

Halazy, et al., "5-HT$_{1B/1D}$ antagonists and depression", *Exp. Opin. Ther. Patents*, 7(4) 339352 (1997).

Cryan et al., "5-HT$_{1A}$ and Beyond: The Role of Serotonin and its Receptors in Depression and the Antidepressant Response", *Hum. Psychopharmacol. Clin. Exp.*, 15, 113–135 (2000).

International Search Report.

Frank Kerrigan et al., "Synthesis of Arylpiperazines via Palladium–Catalysed Aromatic Amination Reactions of Bromoarenes with N–tert–butoxycarbonylpiperazine," Tetrahedron Letters, vol. 39, 1998, p. 2219–2222.

International Search Report.

* cited by examiner

THERAPEUTIC HETEROCYCLIC COMPOUNDS

This application claims priority to foreign patent Application Number 0103650-8, filed in Sweden on Nov. 2, 2001 which is pending and it also claims priority to U.S. Provisional Patent Application Number 60/262,107 filed on Jan. 16, 2001. This patent application is co-pending with PCT Application No. PCT/SE02/00068 filed on Jan. 15, 2002 in European Patent Office in Sweden. This invention relates to novel 8-amino derivatives, methods for their preparation, pharmaceutical compositions containing them and their use in therapy.

FIELD OF THE INVENTION

Background of the Invention

Serotonin (5-HT) has been implicated in many psychiatric disorders including but not limited to depression, generalized anxiety, eating disorders, dementia, panic disorder, and sleep disorders. Furthermore serotonin has been implicated in gastrointestinal disorders, cardiovascular regulation, motor disorders, endocrine disorders, vasospasm and sexual dysfunction. Serotonin receptors have been subdivided into at least 14 subtypes, see Barnes and Sharp, Neuropharmacology, 1999, 38, 1083–1152, incorporated herein by reference. These various subtypes are responsible for serotonin's action in many pathophysicogical conditions. The 5-$HT_1$ family of receptors has high affinity for serotonin and consists of five related receptors. This family includes the 5-$HT_{1B}$ and 5-$HT_{1D}$ receptor subtypes. Compounds that interact with the 5-$HT_1$ family are known to have therapeutic potential in the above mentioned disorders and diseases. In particular, compounds that are 5$HT_{1B}$ and 5$HT_{1D}$ antagonist have been known to be antidepressant and anxiolytic agents. Compounds that are 5$HT_{1B}$ and 5$HT_{1D}$ agonists have been used in the treatment of migraine.

SUMMARY OF THE INVENTION

Provided herein is a compound having the formula (I):

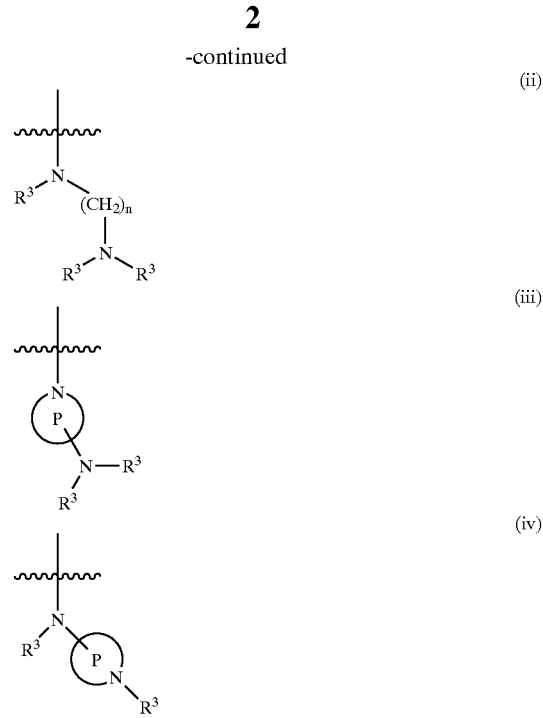

wherein
$R^1$ is, at each position, independently represented by hydrogen, optionally substituted alkyl, optionally substituted cycloalkyl, thiomethoxy, —NHA, —$NA_2$, —NHC(=O)A, aminocarbonyl, —C(=O)NHA, —C(=O)$NA_2$, halogen, hydroxy, —OA, cyano or aryl;
A is optionally substituted alkyl, optionally substituted cycloalkyl, optionally substituted alkenyl or optionally substituted alkynyl;
$R^2$ is represented by (i), (ii), (iii), or (iv) below:

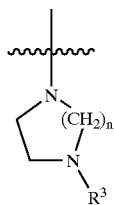

(i)

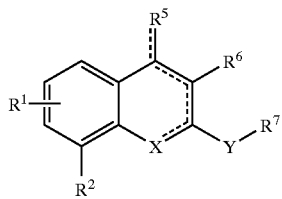

(ii)

(iii)

(iv)

$R^3$ is independently at each position represented by —H, optionally substituted $C_{1-6}$ alkyl, optionally substituted $C_{2-6}$ alkenyl, optionally substituted $C_{2-6}$ alkynyl, optionally substituted $C_{3-6}$ cycloalkyl or AOH;
n is 2, 3 or 4;
P is a heterocyclic ring;
$R^4$ is —H or optionally substituted $C_{1-4}$ alkyl;
$R^5$ is —H, =O, —$OR^4$, —$NR^4{}_2$=$NR^4$, —$SR^4$ or =S;
$R^6$ is —H or methyl;
X is O, N, NH or S;
Y is —C(=O)NH—, —C(=O)NA—, —C(=O)N(A)—, —NHC(=O)—, —C(=S)NH—, —$CH_2$NH—, —C(=O)$CH_2$—, —$CH_2$C(=O)—, —C(=O)-piperazine-, —NAC(=O)—, —C(=S)N(A)—, $CH_2$NA, NA$CH_2$ or a 5-membered heterocyclic;
$R^7$ is a monocyclic or bicyclic aromatic ring or a heterocycle optionally substituted by one or more substituents selected from $R^8$–$R^9$ and $R^{10}$; wherein $R^7$ is connected to Y either by a single bond as tether, or by a ring fusion comprising a bond and two ring atoms shared by both rings;
$R^8$ is —$CH_2$—, —C(=O)—, —$SO_2$—, —$SO_2$NH—, —C(=O)NH—, —O—, —S—, —S(=O)— a single bond as tether from $R^7$ to $R^9$, or a five-membered heterocyclic connected to $R^7$ by either a single bond or by a ring fusion comprising a bond and two ring atoms shared by both rings, $R^9$ is optionally substituted heterocycle, optionally substituted aryl, optionally substituted piperazinyl-R11, optionally substituted morpholinyl-R11 or optionally substituted, C(=O)A;
$R^{10}$ is optionally substituted alkyl, optionally substituted cycloalkyl, hydroxy, aryl, cyano, halogen, —C(=O)$NH_2$, methylthio, —NHA, —$NA_2$, —NHC(=O)A, —C(=O)NHA, —C(=O)$NA_2$, or —OA;
$R^{11}$ is —H, alkyl, AOH, —$SO_2$A, —$SO_2NH_2$, —$SO_2$NHA, —$SO_2NA_2$, —$SO_2NHAR^9$, —C(=O)$R^9$, -alkyl$R^9$, C(=O)A, C(=O)$NH_2$, C(=O)NHA, C(=O)$NA_2$ or C(=O)OA; or a pharmaceutically acceptable salt of said compound.

represents a bond which may be either a single bond or a double bond, with the proviso that multiple double bonds are separated from one another by at least one single bond.

In another aspect of the invention, $R^5$ and X are both O and thus provides a compound represented by the formula (II):

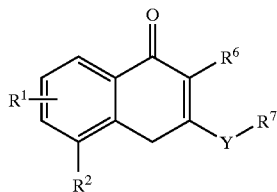

II wherein
$R^1$ is, at each position, independently represented by hydrogen, optionally substituted alkyl, optionally substituted cycloalkyl, thiomethoxy, —NHA, —NA$_2$, —NHC(=O)A, aminocarbonyl, —C(=O)NHA, —C(=O)NA$_2$, halogen, hydroxy, —OA, cyano or aryl;
A is optionally substituted alkyl, optionally substituted cycloalkyl, optionally substituted alkenyl or optionally substituted alkynyl;
$R^2$ is represented by (i), (ii), (iii), or (iv) below:

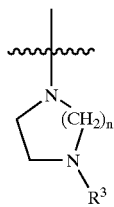
(i)

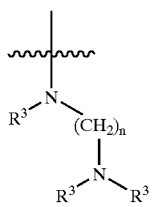
(ii)

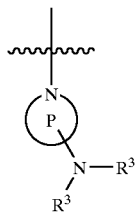
(iii)

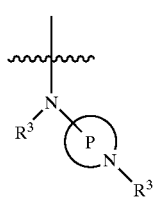
(iv)

$R^3$ is independently at each position represented by —H optionally substituted $C_{1-6}$ alkyl, optionally substituted $C_{2-6}$ alkenyl, optionally substituted $C_{2-6}$ alkynyl, optionally substituted $C_{3-6}$ cycloalkyl or AOH;
n is 2, 3 or 4;

P is a heterocyclic ring;
$R^6$ is —H or methyl;
Y is —C(=O)NH—, —C(=O)NA—, —C(=O)N(A)—, —NHC(=O)—, —C(=S)NH—, —CH$_2$NH—, —C(=O)—, —C(=O)CH$_2$—, —CH$_2$C(=O)—, —C(=O)-piperazine-, —[NAC(=O)—, —C(=S)N(A)—, —CH$_2$NA—, —NACH$_2$— or a 5-membered heterocyclic.
$R^7$ is a monocyclic or bicyclic aromatic ring or a heterocycle optionally substituted by one or more substituents selected from $R^8$–$R^9$ and $R^{10}$; wherein $R^7$ is connected to Y either by a single bond or by a ring fusion;
$R^8$ is —CH$_2$—, —C(=O)—, —SO$_2$—, —SO$_2$NH—, —C(=O)NH—, —O—, —S—, —S(=O)—, a single bond as tether from $R^7$ to $R^9$, a five membered heterocyclic connected to $R^7$ by either a single bond or by a ring fusion;
$R^9$ is optionally substituted heterocycle, optionally substituted aryl, optionally substituted piperazinyl-R11, optionally substituted morpholinyl-R11 or optionally substituted thiomorpholinyl or —C(=O)A;
$R^{10}$ is optionally substituted alkyl, optionally substituted cycloalkyl, hydroxy, aryl, cyano, halogen, —C(=O)NH$_2$—, methylthio, —NHA, —NA$_2$, —NHC(=O)A, —C(=O)NHA, —C(=O)NA$_2$ or OA;
$R^{11}$ is —H, alkyl, —AOH, —SO$_2$A, —SO$_2$NH$_2$, —SO$_2$NHA, —SO$_2$NA$_2$, —SO$_2$NHAR$^9$, —C(=O)R$^9$, -alkylR$^9$, C(=O)A, C(=O)NH$_2$, C(=O)NHA, C(=O)NA$_2$ or —C(=O)OA; or a pharmaceutically acceptable salt of said compound.

In another aspect of the invention, $R^5$ is H and X is O and thus is provided a compound represented by the formula (III):

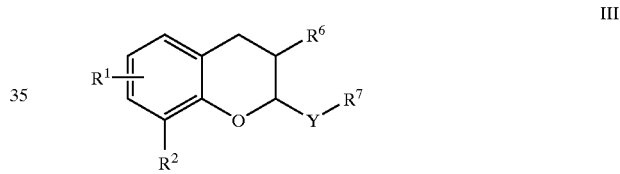

III wherein
$R^1$ is, at each position, independently represented by hydrogen, optionally substituted alkyl, optionally substituted cycloalkyl, thiomethoxy, —NHA, —NA$_2$, —NHC(=O)A, aminocarbonyl, —C(=O)NHA, —C(=O)NA$_2$, halogen, hydroxy, —OA, cyano or aryl;
A is optionally substituted alkyl, optionally substituted cycloalkyl, optionally substituted alkenyl or optionally substituted alkynyl;
$R^2$ is represented by (i), (ii), (iii), or (iv) below:

(i)

(ii)

-continued

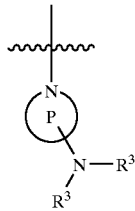
(iii)

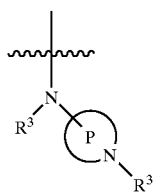
(iv)

R³ is —H, optionally substituted C₁₋₆ alkyl, optionally substituted C₂₋₆ alkenyl, optionally substituted C₂₋₆ alkynyl, optionally substituted C₃₋₆ cycloalkyl or AOH;
n is 2, 3 or 4;
P is a heterocyclic ring;
R⁶ is —H or methyl;
Y is —C(=O)NH—, —C(=O)NA—, —C(=O)N(A)—, —NHC(=O), —C(=S)NH—, —CH₂NH—, —C(=O)—, —C(=O)CH₂—, —CH₂C(=O)—, —C(=O)-piperazine-, —NAC(=O)—, —C(=S)N (A)—, CH₂NA, NACH₂ or a 5-membered heterocyclic.
R⁷ is a monocyclic or bicyclic aromatic ring or a heterocycle optionally substituted by one or more substituents selected from R⁸–R⁹ and R¹⁰; wherein R⁷ is connected to Y either by a single bond or by a ring fusion;
R⁸ is —CH₂—, —C(=O)—, —SO₂—, —SO₂NH—, —C(=O)NH—, —O—, —S—, —S(=O)—, a single bond as tether from R⁷ to R⁹, 5-membered heterocycle connected to R⁷ by either a single bond or by a ring fusion;
R⁹ is optionally substituted heterocycle, optionally substituted aryl, optionally substituted piperazinyl-R11, optionally substituted morpholinyl-R11 or optionally substituted or C(=O)A;
R¹⁰ is optionally substituted alkyl, optionally substituted cycloalkyl, hydroxy, aryl, cyano, halogen, —C(=O) NH₂—, methylthio, —NHA, —NA₂, —NHC(=O)A, C(=O)NHA, C(=O)NA₂ or OA;
R¹¹ is —H, alkyl, AOH, —SO₂A, —SO₂NH₂, —SO₂NHA, —SO₂NA₂, —SO₂NHAR⁹, —C(=O)R⁹, -alkylR⁹, C(=O)A, C(=O)NH₂, C(=O)NHA, C(=O)NA₂ or —C(=O)OA; or a pharmaceutically acceptable salt of said compound.

In another aspect of the invention, X is N and R⁵ is O and thus provides a compound represented by the formula (IV):

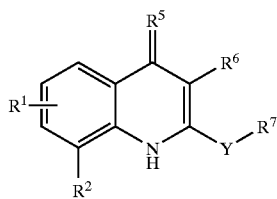
IV wherein
R¹ is, at each position, independently represented by hydrogen, optionally substituted alkyl, optionally substituted cycloalkyl, methoxy, thiomethoxy, —NHA, —NA₂, —NHC(=O)A, aminocarbonyl, —C(=O)NHA, —C(=O)NA₂, halogen, hydroxy, —OA, cyano or aryl;
A is optionally substituted alkyl, optionally substituted cycloalkyl, optionally substituted alkenyl or optionally substituted alkynyl;
R² is represented by (i), (ii), (iii), or (iv) below:

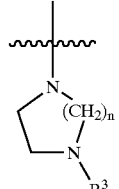
(i)

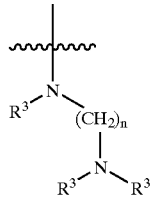
(ii)

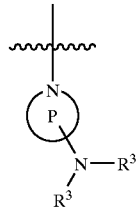
(iii)

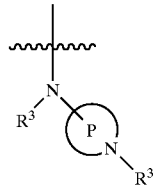
(iv)

R³ is —H, optionally substituted C₁₋₆ alkyl, optionally substituted C₂₋₆ alkenyl, optionally substituted C₂₋₆akynyl, optionally substituted C₃₋₆ cycloalkyl or AOH;
n is 2, 3 or 4;
P is a heterocyclic ring;
R⁴ is —H or optionally substituted C₁₋₄ alkyl;
R⁵ is =O, =NR⁴ or =S;
R⁶ is —H or methyl;
Y is —C(=O)NH—, —C(=O)NA—, —C(=O)N(A)—, —NHC(=O)—, —C(=S)NH—, —CH₂NH—, —C(=O)CH₂—, —CH₂C(=O)—, —C(=O)-piperazine-, —C(=O)R⁸—, —NAC(=O)—, —C(=S) N(A)—, —CH₂N(A)—, —N(A)CH₂— or a 5-membered heterocyclic.
R⁷ is a monocyclic or bicyclic aromatic ring or a heterocycle optionally substituted by one or more substituents selected from R⁸–R⁹ and R¹⁰; wherein R⁷ is connected to Y either by a single bond or by a ring fusion;
R⁸ is —CH₂—, —C(=O)—, —SO₂—, —SO₂NH—, —C(=O)NH—, —O—, —S—, —S(=O)—, a single bond as tether from R⁷ to R⁹, a five-membered heterocyclic connected to R⁷ by either a single bond or by a ring fusion;
R⁹ is optionally substituted heterocycle, optionally substituted aryl, optionally substituted piperazinyl-R11, optionally substituted morpholinyl-R11 or optionally substituted thiomorpholinyl or —C(=O)A;

$R^{10}$ is optionally substituted alkyl, optionally substituted cycloalkyl, hydroxy, aryl, cyano, halogen, —C(=O)NH$_2$—, methylthio, —NHA, —NA$_2$, —NHC(=O)A, —C(=O)NHA, —C(=O)NA$_2$ or OA;

$R^{11}$ is —H, alkyl, AOH, —SO$_2$A, —SO$_2$NH$_2$, —SO$_2$NHA, —SO$_2$NA$_2$, —SO$_2$NHAR$^9$, —C(=O)R$^9$, -alkylR$^9$, C(=O)A, C(=O)NH$_2$, C(=O)NHA, C(=O)NA$_2$ or —C(=O)OA; or a pharmaceutically acceptable salt of said compound.

In another aspect of the invention, X is N and thus provides a compound represented by the formula (V):

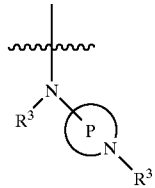

V wherein $R^1$ is, at each position, independently represented by hydrogen, optionally substituted alkyl, optionally substituted cycloalkyl, thiomethoxy, —NHA, —NA$_2$, —NHC(=O)A, aminocarbonyl, —C(=O)NHA, —C(=O)NA$_2$, halogen, hydroxy, —OA, cyano or aryl;

A is optionally substituted alkyl, optionally substituted cycloalkyl, optionally substituted alkenyl or optionally substituted alkynyl;

$R^2$ is represented by (i), (ii), (iii), or (iv) below:

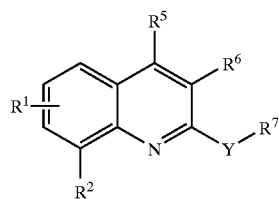

(i)

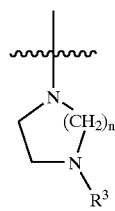

(ii)

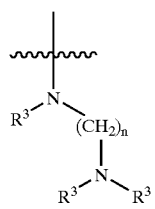

(iii)

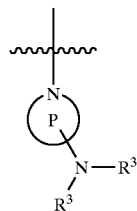

(iv)

$R^3$ is —H, optionally substituted $C_{1-6}$ alkyl, optionally substituted $C_{2-6}$ alkenyl, optionally substituted $C_{2-6}$ alkynyl, optionally substituted $C_{3-6}$ cycloalkyl or AOH;

n is 2, 3 or 4;

P is a heterocyclic ring;

$R^4$—H or optionally substituted $C_{1-4}$ alkyl;

$R^5$ is —H, —OR$^4$, —NR$^4{}_2$ or —SR$^4$;

$R^6$ is —H or methyl;

Y is —C(=O)NH—, —C(=O)NA—, —C(=O)N(A)—, —NHC(=O)—, —C(=S)NH—, —CH$_2$NH—, —C(=O)—C(=O)CH$_2$—, —CH$_2$C(=O)—, —C(=O)-piperazine-, —N(A)C(=O)—, —C(=S)N(A)—, —CH$_2$N(A), —N(A)CH$_2$— or a 5-membered heterocyclic.

$R^7$ is a monocyclic or bicyclic aromatic ring or a heterocycle optionally substituted by one or more substituents selected from $R^8$–$R^9$ and $R^{10}$; wherein $R^7$ is connected to Y either by a single bond or by a ring fusion;

$R^8$ is —CH$_2$—, —C(=O)—, —SO$_2$—, —SO$_2$NH—, —C(=O)NH—, —O—, —S—, —S(=O)—, a single bond as tether from $R^7$ to $R^9$, a five membered heterocyclic connected to $R^7$ by either a single bond or by a ring fusion;

$R^9$ is optionally substituted heterocycle, optionally substituted aryl, optionally substituted piperazinyl-R11, optionally substituted morpholinyl-R11 or optionally substituted or —C(=O)A;

$R^{10}$ is optionally substituted alkyl, optionally substituted cycloalkyl, hydroxy, aryl, cyano, halogen, —C(=O)NH$_2$—, methylthio, —NHA, —NA$_2$, —NHC(=O)A, —C(=O)NHA, —C(=O)NA$_2$ or OA;

$R^{11}$ is —H, alkyl, AOH, —SO$_2$A, —SO$_2$NH$_2$, —SO$_2$NHA, —SO$_2$NA$_2$, —SO$_2$NHAR$^9$, —C(=O)R$^9$, -alkylR$^9$, C(=O)A, C(=O)NH$_2$, C(=O)NHA, C(=O)NA$_2$, and C(=O)OA; or a pharmaceutically acceptable salt of said compound.

The term "hydrocarbyl" refers to any structure comprising only carbon and hydrogen atoms up to 14 carbon atoms.

The term "alkyl" used alone or as a suffix or prefix, refers to straight or branched chain hydrocarbyl radicals comprising 1 to about 12 carbon atoms.

The term "alkenyl" refers to straight or branched chain hydrocarbyl radicals having at least one carbon-carbon double bond and comprising at least 2 up to about 12 carbon atoms.

The term "alkynyl" refers to straight or branched chain hydrocarbyl radicals having at least one carbon-carbon triple bond and comprising at least 2 up to about 12 carbon atoms.

The term "cycloalkyl" refers to ring-containing hydrocarbyl radicals comprising at least 3 up to about 12 carbon atoms.

The term "cycloalkenyl" refers to ring-containing hydrocarbyl radicals having at least one carbon-carbon double bond and comprising at least 3 up to about 12 carbon atoms.

The term "cycloalkynyl" refers to ring-containing hydrocarbyl radicals having at least one carbon-carbon triple bond and comprising about 7 up to about 12 carbon atoms.

The term "aromatic" refers to hydrocarbyl radicals having one or more polyunsaturated carbon rings having aromatic character, (e.g., 4n+2 delocalized electrons) and comprising 6 up to about 14 carbon atoms.

The term "aryl" refers to aromatic radicals including both monocyclic aromatic radicals comprising 6 carbon atoms and polycyclic aromatic radicals comprising up to about 14 carbon atoms.

The term "alkylene" refers to divalent alkyl moieties, wherein said moiety serves to link two structures together.

The term "heterocycle" or "heterocyclic" or "heterocyclic moiety" refers to ring-containing monovalent and divalent radicals having one or more heteroatoms, independently selected from N, O and S, as part of the ring structure and comprising at least 3 and up to about 20 atoms in the rings preferably 5 and 6 membered rings. Heterocyclic moieties may be saturated or unsaturated, containing one or more double bonds, and heterocyclic moieties may contain more than one ring.

The term "heteroaryl" refers to heterocyclic monovalent and divalent radicals having aromatic character.

Heterocyclic moieties include for example monocyclic moieties such as: aziridine, oxirane, thiirane, azetidine, oxetane, thietane, pyrrolidine, pyrroline, imidazolidine, pyrazolidine, dioxolane, sulfolane 2,3-dihydrofuran, 2,5-dihydrofuran tetrahydrofuran, thiophane, piperidine, 1,2,3, 6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide. In addition heterocyclic moieties include heteroaryl rings such as: pyridyl, pyrazinyl, pyrimidinyl, pyridazinyl, thienyl, furyl, pyrrolyl, imidazolyl, thiazolyl, oxazolyl, pyrazolyl, isothiazolyl, isoazulyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl. Additionally, heterocyclic moieties encompass polycyclic moieties such as: indole, indoline, quinoline, tetrahydroquinoline, isoquinoline, tetrahydroisoquinoline, 1,4-benzodioxan, coumarin, dihydrocoumarin, benzofuran, 2,3-dihydrobenzofuran, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocyclic moieties include polycyclic heterocyclic moieties wherein the ring fusion between two or more rings comprises more than one bond common to both rings and more than two atoms common to both rings. Examples of such bridged heterocycles include quinuclidine, diazabicyclo[2.2.1]heptane and 7-oxabicyclo[2.2.1]heptane.

The term "halo" or "halogen" refers to fluorine, chlorine, bromine and iodine radicals.

The term "alkoxy" refers to radicals of the general formula —O—R, wherein R is selected from a hydrocarbyl radical. Alkoxy moieties include methoxy, ethoxy, propoxy, isopropoxy, butoxy, t-butoxy, isobutoxy, cyclopropylmethoxy, allyloxy, and propargyloxy.

The term amine or amino refers to radicals of the general formula —NRR', wherein R and R' are independently selected from hydrogen or a hydrocarby radical.

DETAILED DESCRIPTION OF THE INVENTION

In a further aspect of the invention, A, $R^1$ and $R^3$, each independently, as an alkyl, alkenyl, alkynyl and as a cycloalkyl, may optionally be substituted with halogen, nitro, cyano, hydroxy, trifluoromethyl, amino, carboxy, carboxamido, amidino, carbamoyl, mercapto, sulfamoyl, $C_{1-4}$ alkyl, $C_{2-4}$ alkenyl, $C_{2-4}$ alkynyl, $C_{3-6}$ cycloalkyl, $C_{3-6}$ cycloalkenyl, $C_{1-4}$ alkoxy, $C_{1-4}$ alkanoyl, $C_{1-4}$ alkanoyloxy, NH($C_{1-4}$ alkyl), N($C_{1-4}$ alkyl)$_2$, $C_{1-4}$ alkanoylamino, ($C_{1-4}$ alkanoyl)$_2$amino, N-($C_{1-4}$ alkyl)carbamoyl, N,N-($C_{1-4}$ alkyl)$_2$carbamoyl, ($C_{1-4}$)S, ($C_{1-4}$ alkyl)S(O), ($C_{1-4}$ alkyl)S(O)$_2$, ($C_{1-4}$)alkoxycarbonyl, N-($C_{1-4}$ alkyl)sulfamoyl, N,N-$C_{1-4}$ alkyl)sulfamoyl, $C_{1-4}$ alkylsolfonylamino, and heterocyclic.

Examples of optional substituents for aryl and heterocyclic groups, when not otherwise defined, are halogen, nitro, cyano, hydroxy, trifluoromethyl, amino, carboxy, carboxamido, amidino, carbamoyl, mercapto, sulfamoyl, $C_{1-4}$ allyl, $C_{2-4}$ alkenyl, $C_{2-4}$ alkynyl, $C_{3-6}$ cycloalkyl, $C_{3-6}$ cycloalkenyl, $C_{1-4}$ alkoxy, $C_{1-4}$ alkanoyl, $C_{1-4}$ alkanoyloxy, N-($C_{1-4}$ alkyl), N($C_{1-4}$ alkyl)$_2$, $C_{1-4}$ alkanoylamino, ($C_{1-4}$ alkanoyl)$_2$amino, N-($C_{1-4}$ alkyl)carbamoyl, N,N-($C_{1-4}$ alkyl)$_2$carbamoyl, ($C_{1-4}$)S, ($C_{1-4}$ alkyl)S(O), ($C_{1-4}$ alkyl)S(O)$_2$, ($C_{1-4}$)alkoxycarbonyl, N-($C_{1-4}$ alkyl)sulfamoyl, N,N-$C_{1-4}$ alkyl)sulfamoyl, $C_{1-4}$ alkylsolfonylamino, and heterocyclic.

A, $R^1$ and $R^3$ each independently as an alkyl, alkenyl or alkynyl may be straight or branched, preferably having 1–6 carbon atoms. A, $R^1$ and $R^3$ preferably have 3–6 atoms when each are independently a cyclic alkyl. Other preferable values for A, $R^1$ and $R^3$ when each are an alkyl include methyl, ethyl, n-propyl, isopropyl, n-butyl, isobutyl, tert-butyl, cyclopentyl, neopentyl and cyclohexyl. Preferable values for $R^1$ when $R^1$ is a halogen are fluorine, chlorine, and bromine. Other preferable values for $R^1$ when $R^1$ is at position 6 on the bicyclic ring are methyl, ethyl, ethoxy and methoxy. Preferable values for $R^1$ when $R^1$ is at position 5 on the bicyclic ring are —H, methyl, ethyl and methoxy. When $R^1$ is at position 5- on the bicyclic ring, $R^1$ is more preferably —H. When $R^1$ is at position 7- on the bicyclic ring, $R^1$ is preferably —H.

$R^2$ is preferably represented by Formula i. Preferably $R^2$ is represented by formula i, wherein n equals 2. Most preferably $R^2$ is represented by N-methyl piperazinyl.

$R^3$ is preferably represented by hydrogen, methyl, ethyl, n-propyl, isopropyl, n-butyl, isobutyl, and tert-butyl. $R^3$ is most preferably represented by methyl.

$R^4$ is preferably represented by hydrogen, methyl, ethyl, n-propyl, isopropyl and trimethylsilanyl-ethoxymethoxy. $R^4$ is most preferably represented by methyl.

$R^6$ is preferably represented by H.

Y represents a linking group. Y is preferably —C(=O)N(CH$_3$)—, when Y is —C(=O)N(A)—. Y may also be —C(=O)-piperazine. When Y represents a five-membered heterocyclic ring, Y may be represented by, for example, pyrrole, thiophene, furan, imidazole, thiazole, oxazole, pyrazole, isothiazole, isoxazole, 1,2,3-triazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole or 1,3,4-oxadiazole.

More preferably, Y is —C(=O)NH—.

Examples of $R^7$ that represent monocyclic or bicyclic aromatic ring or a heterocycle include, but are not limited to, phenyl; 1- and 2-naphthyl; 2-, 3- and 4-pyridyl; 2- and 3-thienyl; 2- and 3-furyl; 1-, 2- and 3-pyrrolyl; imidazolyl; thiazolyl; oxazolyl; pyrazolyl; isothiazolyl; isoxazolyl; 1,2,3-triazolyl; 1,2,3-thiadiazolyl; 1,2,3-oxadiazolyl; 1,2,4-triazolyl; 1,2,4-tlhiadiazolyl; 1,2,4-oxadiazolyl; 1,3,4-triazolyl; 1,3,4-thiadiazolyl; 1,3,4 oxadiazolyl; quinolyl; isoquinolyl; indolyl; benzothienyl; benzofuryl; benzimidazolyl; benzthiazolyl; benzoxazolyl; or triazinyl.

$R^7$ may also be represented by the Formula (v):

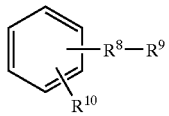
(v)

$R^7$ may further be represented by the Formula (vi):

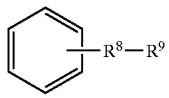
(vi)

When the values for $R^7$ are as set forth above, $R^8$ may be a single bond as tether, —C(=O)—, —CH$_2$—, —C(=O)—, —SO$_2$—, —S(=O)—, —S—, —O—, —C(=O)NH—, —SO$_2$NH—, or a five membered heterocycle connected to $R^7$ by a single bond or by ring fusion; and $R^9$ may represent an aryl, heterocyclic or heteroaryl each independently optionally substituted with halogen, nitro, cyano, hydroxy, trifluoromethyl, amino, carboxy, carbamoyl, mercapto, sulfamoyl, $C_{1-4}$ alkyl, $C_{2-4}$ alkenyl, $C_{2-6}$ alkynyl, $C_{3-6}$ cycloalkyl, $C_{3-6}$ cycloalkenyl, $C_{1-4}$ alkoxy, $C_{1-4}$ alkanoyl, $C_{1-4}$ alkanoyloxy, N-($C_{1-4}$ alkyl), N($C_{1-4}$ alkyl)$_2$, $C_{1-4}$ alkanoylamino, ($C_{1-4}$ alkanoyl)$_2$amino, N-($C_{1-4}$ alkyl) carbamoyl, N,N-($C_{14}$)$_2$-carbamoyl, $C_{1-4}$)S, $C_{1-4}$S(O), ($C_{1-4}$ alkyl)S(=O$_2$, ($C_{1-4}$)alkoxycarbonyl, N-($C_{1-4}$ alkyl) sulfamoyl, N,N-$C_{1-4}$ alkyl)sulfamoyl, $C_{1-4}$ alkylsolfonylamino, heterocyclic. Preferably $R^9$ is a an optionally substituted heterocyclic moiety.

More preferably $R^9$ represents piperazine, thiomorpholine or morpholine each independently optionally substituted on carbon with at least one substituent selected from A. $R^8$ may be a five membered heterocycle, incorporating at least one heteroatom selected from N, O, or S and it may be connected to $R^7$ by a ring fusion, preferably when $R^7$ is phenyl. When $R^8$ is a single bond as tether, $R^9$ is preferably methoxy, cyano, a five-membered heterocycle optionally substituted with at least one substituent represented by A or $R^{11}$ for example compounds represented by the Formulas (vii), (viii) and (ix):

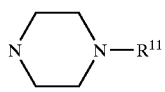
(vii)

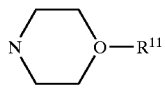
(viii)

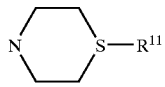
(ix)

When $R^8$ is represented by a 5-membered heterocyclic comprising N and further when it is connected to $R^7$ by a ring fusion, $R^9$ is preferably —C(=O)A attached at the nitrogen atom, $R^9$ is most preferably —C(=O)CH$_2$CH$_3$.

When $R^7$ is phenyl or a 6-membered heterocyclic ring, $R^9$ is attached via the $R^8$ tether at the 2-, 3- or 4-position of the phenyl or a 6-membered heterocyclic ring. Preferably, $R^9$ is attached via the $R^8$ tether at the 3- or 4-position of the phenyl or a 6-membered heterocyclic ring. More preferably, $R^9$ is attached via the $R^8$ tether at the 4 position of the phenyl or a 6-membered heterocyclic ring.

$R^{10}$ may be represented by alkyl or cycloalkyl each independently optionally substituted with halogen, nitro, cyano, hydroxy, trifluoromethyl, amino, carboxy, carbamoyl, mercapto, sulfamoyl, $C_{1-4}$ alkyl, $C_{2-4}$ alkenyl, $C_{2-4}$ alkynyl, $C_{3-6}$ cycloalkyl, $C_{3-6}$ cycloalkenyl, $C_{1-4}$ alkoxy, $C_{1-4}$ alkanoyl, $C_{1-4}$ alkanoyloxy, N-($C_{1-4}$ alkyl), N($C_{1-4}$ alkyl)$_2$, $C_{1-4}$ alkanoylamino, ($C_{1-4}$ alkanoyl)$_2$amino, N-($C_{1-4}$ alkyl)carbamoyl, N,N-($C_{1-4}$)$_2$carbamoyl, $C_{1-4}$)S, $C_{1-4}$S(O), ($C_{1-4}$ alkyl)S(O)$_2$, ($C_{1-4}$)alkoxycarbonyl, N-($C_{1-4}$ alkyl)sulfamoyl, N,N-$C_{1-4}$ alkyl)sulfamoyl, $C_{1-4}$ alkylsulfonylamino, or heterocyclic. $R^{10}$ is preferably a halogen, preferably chlorine or fluorine, cyano, or —OCH$_3$. When $R^{10}$ is a halogen it is preferably chlorine or fluorine. When $R^7$ is a phenyl or 6-membered heteroaromatic ring, $R^{10}$ is attached at the 2-, 3- or 4-position of the phenyl or a 6-membered heterocyclic ring. Preferably, $R^{10}$ is attached at the 2- or 3-position of the phenyl or a 6-membered heterocyclic ring when $R^9$ is attached via the $R^8$ tether at the 4-position of the phenyl or a 6-membered heterocyclic ring. More preferably, $R^{10}$ is attached at the 3-position of the phenyl or a 6-membered heterocyclic ring when $R^9$ is attached via the $R^8$ tether at the 4-position of the phenyl or a 6-membered heterocyclic ring.

When $R^8$ is represented by a single bond as tether, $R^9$ is preferably represented by an optionally substituted heterocyclic, optionally substituted on carbon with at least one substituent selected from A and further substituted on a heteroatom opposite to the heteroatom attached to the tether, with a substituent represented by $R^{11}$ (see e.g., Formulas (vii), (viii) and (ix)). The preferred heterocyclic compounds for R8 are piperazine, morpholine, or thiomorpholine.

When $R^{11}$ represents SO$_2$A it is preferably represented by an alkylsufonyl, more preferably —SO$_2$CH$_3$, —SO$_2$CH$_2$CH$_3$, SO$_2$-n-C$_3$H$_7$, SO$_2$-i-C$_3$H$_7$, SO$_2$-n-C$_4$H$_{10}$, or —SO$_2$-t-C$_4$H$_{10}$. When $R^{11}$ represent C(=O)A, it is preferably represented by an alkylcarbonyl more preferably —C(=O)CH$_3$, —C(=O)CH$_2$CH$_3$, C(=O)-n-C$_4$H$_{10}$, —C(=O)-i-C$_4$H$_{10}$, —C(=O)-t-C$_4$H$_{10}$, or —C(=O) C$_3$H$_7$—. When $R^{11}$ is represented by C(=O)NHA or C(=O)NA$_2$ it is preferably an alkyl or dialkyl carbamoyl more preferably C(=O)NCH$_2$CH$_3$, C(=O)NH-cycloC$_6$H$_{12}$, or C(=O)NH-cycloC$_5$H$_{10}$. When $R^{11}$ is represented by C(=O)R$^9$ it is preferably —C(=O)-pyrrolidine, or —C(=O)-morpholine. When $R^{11}$ is represented by SO$_2$NA$_2$ it is preferably SO$_2$N(CH$_3$)$_2$. When $R^{11}$ is represented by AOH, it is preferably represented by, CH$_2$CH$_2$OH or —C(=O)CH$_2$CH$_{20}$H. $R^{11}$ may also be represented by —C(=O)OC$_4$H$_{10}$.

In preferred embodiments, when Y is represented by —C(=O)NH:
  (a) $R^1$ is halogen or methoxy, most preferably fluorine, at the 6$^{th}$ position of the bicyclic ring, and is preferably hydrogen, methyl, ethyl or methoxy at the 5$^{th}$ position of the bicyclic ring, and is hydrogen at the 7$^{th}$ position on the bicyclic ring;
  (b) $R^2$ is methyl piperazine;
  (c) $R^6$ is hydrogen;
  (d) $R^7$ is phenyl substituted with R8–R9
  (e) $R^8$ is a single bond as tether;
  (f) $R^9$ is a heterocyclic moiety, preferably morpholine or piperazine attached to $R^8$ by nitrogen and optionally substituted on the other nitrogen (for piperazine) with $R^{11}$ or optionally substituted on the oxygen with $R^{11}$ when $R^9$ is morpholine;

(g) $R^{11}$ is AOH or $—SO_2A$ wherein A is represented by methyl or ethyl.

The compounds provided herein are useful in the form as a free base, but may also be provided in the form of a pharmaceutically acceptable salt, and/or in the form of a pharmaceutically acceptable hydrate. For example pharmaceutically acceptable salts of compounds of Formula I, Formula II, Formula III, Formula IV or Formula V include those derived from mineral acids such as for example: hydrochloric acid, nitric acid, phosphoric acid, sulfuric acid, hydrobromic acid, hydroiodic acid, nitrous acid, and phosphorous acid. Pharmaceutically acceptable salts may also be developed with organic acids including aliphatic mono and dicarboxylates and aromatic acids. Other pharmaceutically-acceptable salts of compounds of the present invention include for example hydrochloride, sulfate, pyrosulfate, bisulfate, bisulfite, nitrate, and phosphate.

Processes for the manufacture of the compounds of Formula I, Formula II, Formula III, Formula IV and Formula V are provided as further features of the invention. Many of the Compounds described herein can be made by processes known in the chemical arts for the production of structurally analogous compounds. Accordingly, the compounds of this invention may be prepared by employing procedures known in the literature starting from known compounds or readily prepared intermediates. For example, the core bicyclic, heterocyclic structure may be made by first preparing a chromone, quinolone or quinoline.

For compounds of the present invention that have Y as an amide linker, the compounds are preferably made by the general procedure for amide coupling, that is by coupling an amine with an acid hydrochloride. The amines used in the current invention if not commercially available may be made by known techniques. For example as a first step in the process of making compound of Formula I, Formula II, Formula III, Formula IV or Formula V, a nitro compound may be reduced to an amine. The nitro compound may be a nitrophenyl compound. The resulting amines may be reacted with an acid hydrochloride. Provided herein is a process for preparation of a precursor compound or use in practicing aspects of the present invention by reacting a compound of Formula (VIa):

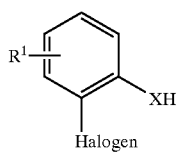

VIa ($R^1$, $R^2$, $R^3$, $R^7$, and X, are as defined for Formula I unless otherwise specified), with for example a compound represented by:

wherein R' is represented by alkyl, preferably lower alkyl (e.g., $C_1$–$C_6$) most preferably methyl or ethyl, to form a precursor compound of Formula (VIb):

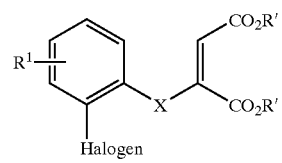

VIb $R^1$ is preferably fluorine, chlorine, methyl, methoxy, ethoxy or hydrogen. The Halogen is preferably Chlorine or Bromine. The reaction may be carried out in the presence of a catalyst such as tetrabultyammonium fluoride in THF. The reaction may be stirred for example at room temperature and refluxed with heat.

Further provided herein is a process for the preparation of a precursor compound comprising hydrolyzing the esters of compound (VIb) to form intermediate (VIc):

VIc

This reaction may be carried our for example by reacting a compound of Formula (VIb) with a base such as sodium hydroxide (aqueous). Also provided here is a process for the preparation of an intermediate by the cyclization of compound (VIc) to form intermediate VId Intermediate compound (VId) may be formed by refluxing a compound of Formula (VIc) with a strong acid (e.g., $H_2SO$) and further refluxed with heat and an alkyl alcohol for example R"OH wherein R" is $C_1$–$C_4$ alkyl, preferably ethyl.

In an additional aspect of the invention, a process is provided for the preparation of an intermediate by reacting a compound of Formula (VId) with an amine of $R^2$ in the presence of a catalyst and a base to form intermediate Formula (VIe):

VIe

In a further embodiment of the invention, a compound of Formula (VId) is reacted with a catalyst selected from the group consisting of nickel and palladium. Preferably the palladium is provided in the presence of a phosphine ligand for example 2,2'-bis(diphenylphosphino)-1,1'-binapthyl. The palladium may be provided as tris(dibenzylideneacetone)dipalladium. The base is preferably selected from the group consisting of potassium carbonate, sodium carbonate, cesium carbonate and triethylamine and mixtures thereof.

Further provided herein is an acid hydrochloride of a compound of Formula (VIe) which is intermediate Formula (VIf):

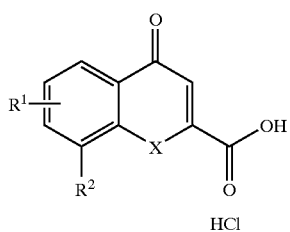

VIf

The intermediate Formula (VIf) may be formed for example by heating a compound of Formula (VIe) in the presence of an acid and water (e.g., $HCl/H_2O$).

In another aspect of the invention provided is intermediate Formula (VIg):

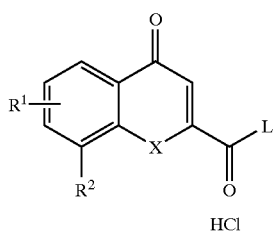

VIg

Thus, in another aspect of the invention, a leaving group is added to the carboxylate of a compound of Formula (VII). L is a leaving group. This intermediate is useful in that the acid is activated to provide an electrophile. L is preferably represented by chlorine in intermediate Formula (VIg) which is prepared by reacting a compound of Formula (VIf) with thionyl chloride ($SOCl_2$).

Provided herein is a compound of Formula (VIh):

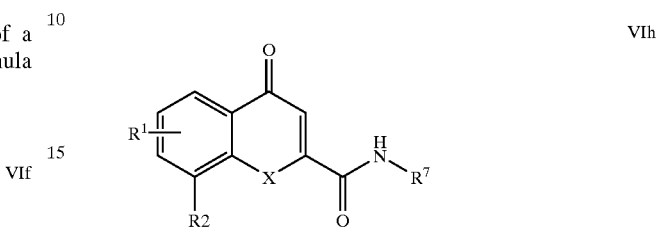

VIh

Methods for reacting amines with acid chlorides may be used to prepare compounds of formula I such as a compound of Formula (VIh) For example, a method for the preparation of (VIh) may include reacting a compound of Formula (VIg) with $H_2N$—$R^7$ in the presence of DIPEA.

Alternatively, compounds of Formula (VIh) may also be prepared by reacting a compound of Formula (VIf) with $H_2N$—$R^7$ in the presence for example 1-hydroxybenzotriazole (HOBT), O-(1H-Benzotriazol-1-yl)-N,N,N'N'-pentamethyleneuronium tetraflubrborate (TBTU), and (dimethylamino)pyridine, preferably in that order.

Compounds of Formulas (VIe), (VIf), and (VIg), and (VIh) may also comprise a pharmaceutically acceptable salt of said compounds.

The compounds and processes above may also be used to prepare the chroman derivatives of Formula (I) via the saturation of the double bond (4H-chromene) in the bicyclic compound. Depending on the reduction conditions, the 4-oxo derivative may or may not be obtained.

A method for preparing the acid hydrochlorides useful in synthesis of a chromone is set forth in Scheme 1 below:

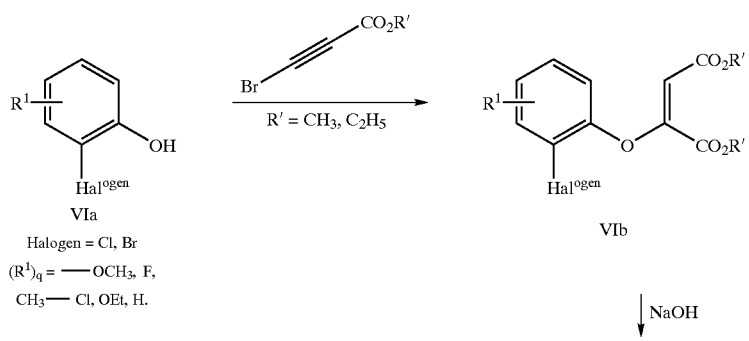

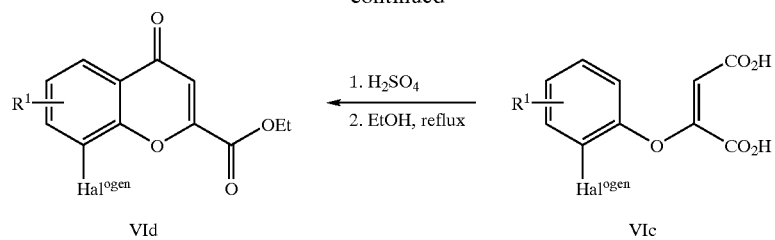
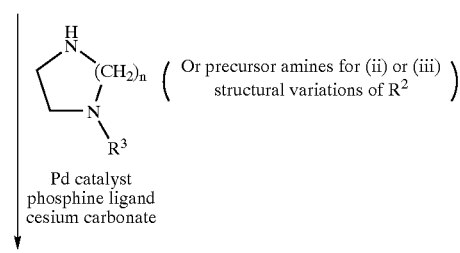
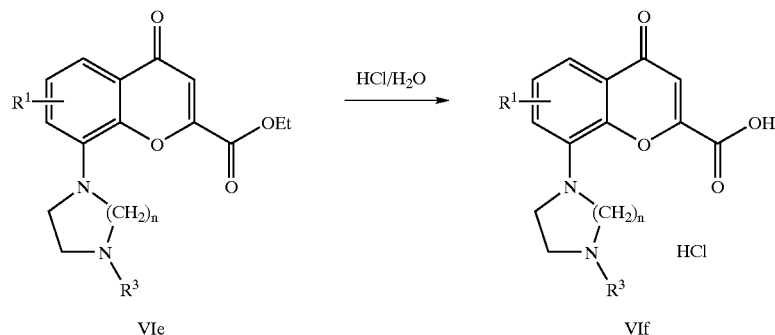
Scheme 1: Preparation of chromone-2-carboxylic acids as intermediates in the synthesis of compounds of the present invention.
Alternatively, the chromone-2-carboxylic acid may be converted to the acid chloride and reacted immediately with an appropriate amine, as depicted in Scheme 2, below:
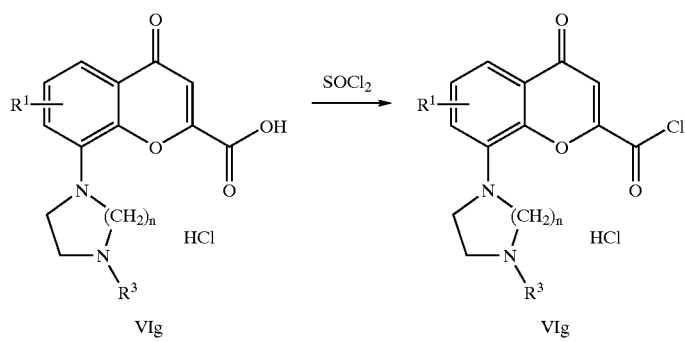
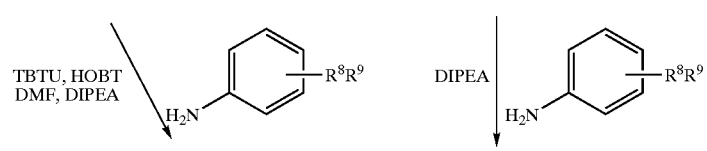

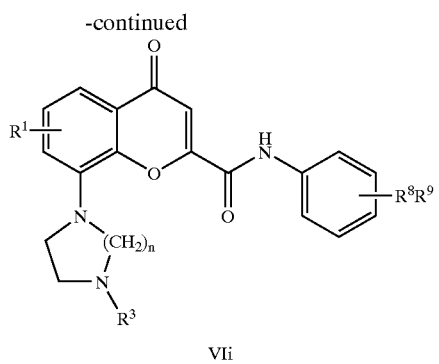

VIi

Scheme 2: Amide synthesis via acid chloride intermediate.

Additional functional group manipulations include, but are not limited to, O-dealkylation and N-dealkylation (Scheme 3).

Quinoline and quinolone compounds of the present invention are prepared and derivatized via synthetic routes similar to those employed for synthesis of the chromone-2-carboxamides described above and in Schemes 1–3. These synthetic routes to quinoline and quinolone compounds of the present invention are depicted in Scheme 4, infra.

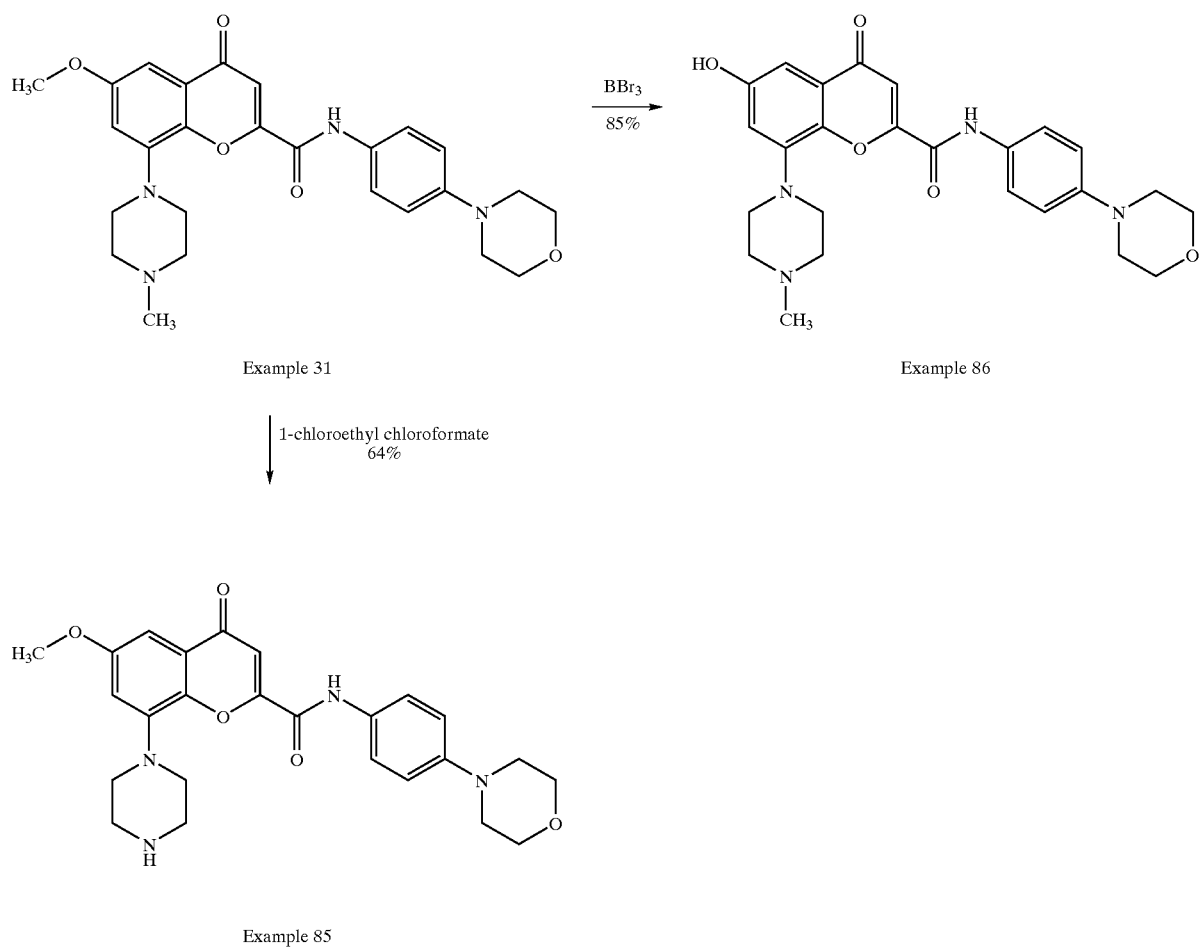

Scheme 3: Functional group manipulation with compounds of the present invention includes, but is not limited to, N- and O-dealkylation.

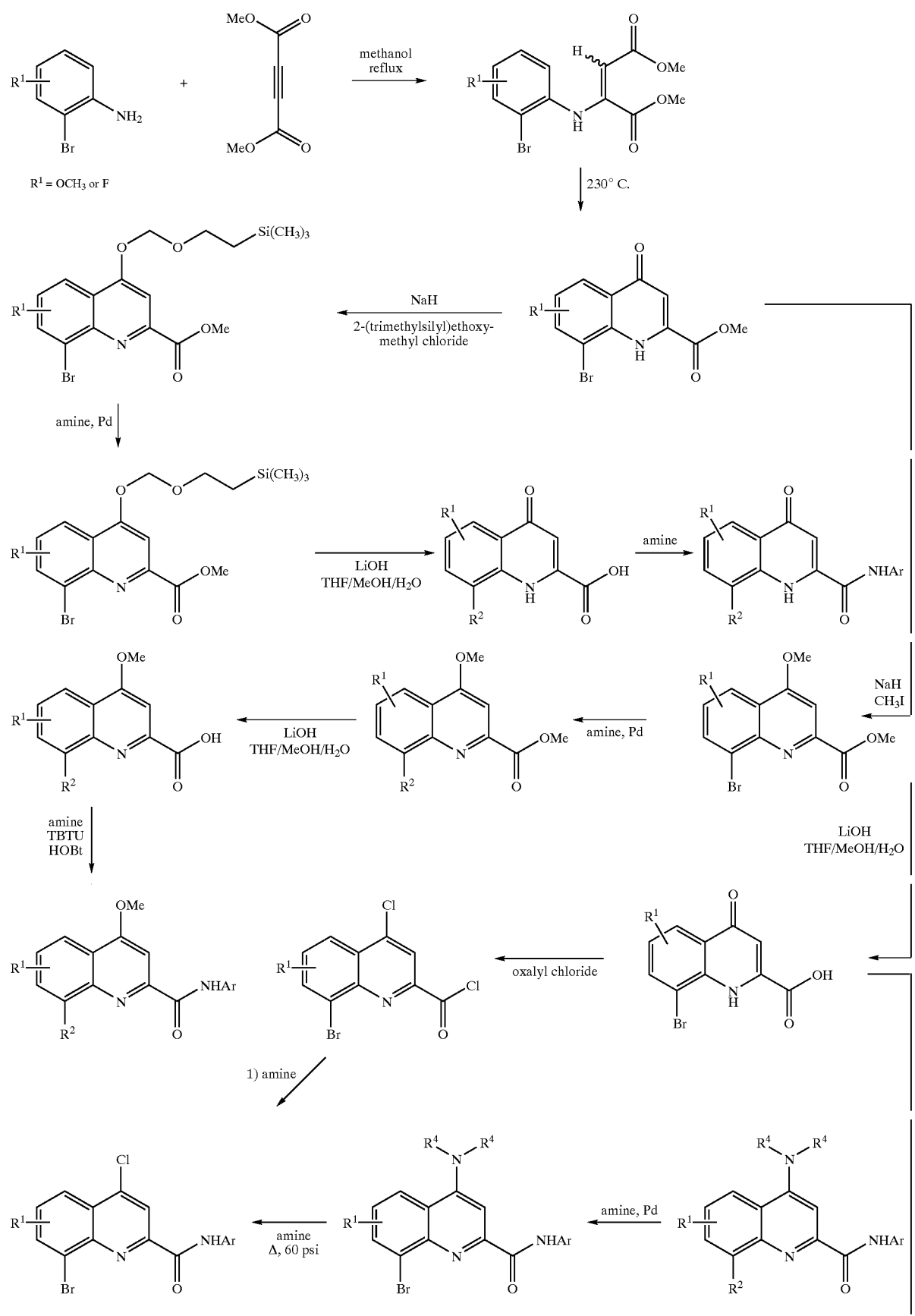

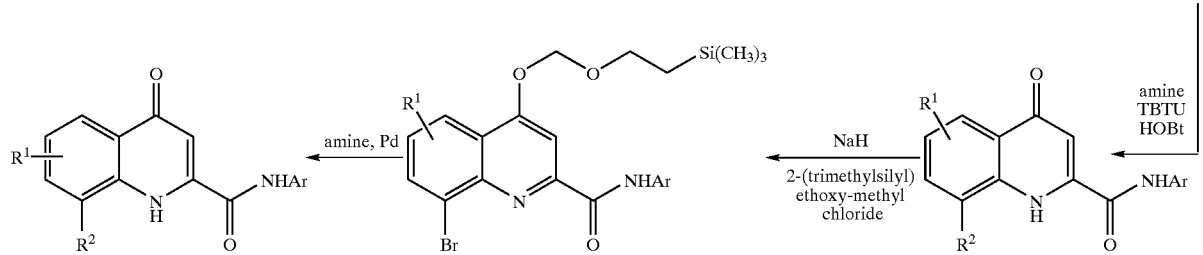

It will be appreciated by those skilled in the art that certain compounds of the present invention contain for example asymmetrically substituted carbon and/or sulfur atoms, and accordingly may exist in and be isolated in, optically-active and racemic forms. Some compounds may exhibit polymorphism, thus it is to be understood that the present invention encompasses racemic, optically-active, polymorphic or stereoisomeric forms, or mixtures thereof, which forms possess properties useful in the treatment of the disorders set forth below. Preparation of optically active forms is well known in the art how (for example by resolution of racemic forms by recrystallization techniques, synthesis from optically-active starting materials, chiral synthesis, or by chromatographic separation using a chiral stationary phase) and how to determine efficacy for the treatment of the disorder described above.

Compounds of Formula I, Formula II, Formula IV and Formula V have been found by the inventors to be useful as 5-$HT_{1B}$ and 5$HT_{1D}$ antagonists. The compounds of Formula I, Formula II, Formula IV and Formula V, and their pharmaceutically acceptable salts, may also be used in a method for the treatment of depression, generalized anxiety, eating disorders, dementia, panic disorder, sleep disorders, gastrointestinal disorders, motor disorders, endocrine disorders, vasospasm and sexual dysfunction. The treatment of these disorders comprises administering to a warm-blooded animal, preferably a mammal, more preferably a human, in need of such treatment, an effective amount of a compound of Formula I, Formula II, Formula IV or Formula V, or a pharmaceutically acceptable salt of said compound.

Compounds of Formula III have been found to be 5-$HT_{1B}$ and 5$HT_{1D}$ agonists. The compounds of Formula III, and their pharmaceutically acceptable salts, may also be used in a method for the treatment of migraine. The treatment of this disorder comprises administering to a warm-blooded animal, preferably a mammal, more preferably a human, in need of such treatment, an effective amount of a compound of Formula III or a pharmaceutically acceptable salt of said compound.

Further provided herein are compounds of Formula I, Formula II, Formula IV or Formula V, and their pharmaceutically acceptable salts, for use in the treatment of depression, generalized anxiety, eating disorders, dementia, panic disorder, sleep disorders, gastrointestinal disorders, motor disorders, endocrine disorders, vasospasm and sexual dysfunction of a warm-blooded animal, preferably a mammal, more preferably a human, in need of such therapy.

Further provided herein is a method of treatment of a warm-blooded animal, preferably a mammal, more preferably a human, suffering from disorders such as depression, generalized anxiety, eating disorders, dementia, panic disorder, sleep disorders, gastrointestinal disorders, motor disorders, endocrine disorders, vasospasm and sexual dysfunction comprising administering to such animal an effective amount of a compound of Formula I, Formula II, Formula IV or Formula V, or a pharmaceutically acceptable salt of the compound.

Further provided is the use of a compound of Formula I, Formula II, Formula IV or Formula V in the preparation of a medicament for the treatment of a disorder such as depression, generalized anxiety, eating disorders, dementia, panic disorder, sleep disorders, in gastrointestinal disorders, motor disorders, endocrine disorders, vasospasm and sexual dysfunction in a warm-blooded animal, preferably a mammal, more preferably a human, suffering from such disorder.

Further provided is the use of a compound of Formula III in the preparation of a medicament for the treatment of a disorder such as migraine in a warm-blooded animal, preferably a mammal, more preferably a human, suffering from such disorder.

The invention further provides a pharmaceutical composition suitable for the treatment of the above describe disorders comprising administering to a warm-blooded animal having such disorder an effective amount of a pharmaceutical composition of a compound of Formula I, Formula II, Formula III, Formula IV or Formula V, or a pharmaceutically acceptable salt.

The invention also provides a pharmaceutical composition comprising a compound of Formula I, Formula II, Formula III, Formula IV or Formula V as defined herein, or a pharmaceutically acceptable salt, in combination with a pharmaceutically acceptable carrier. Preferred compounds of Formula I, Formula II, Formula III, Formula IV and Formula V for use in the compositions of the invention are as described above.

All compounds described herein demonstrate binding affinities (observed Ki values), in an assay described below, of less than about 10 $\mu$M. Further, compounds of the present invention not only demonstrate 5$HT_{1B}$ antagonist activity by reversing 5$HT_{1B}$ agonist-induced hypothermia in the guinea pig, these compounds are considered to be orally active, and hence, they are the preferred compounds. Examples 1, 10, 11, 31, 32, 34, 44, 55, 56, 57, 71 and 72, infra, demonstrate 5$HT_{1B}$ antagonist activity in a dosage range of 0.006–5.5 mg/kg. In addition, compounds described herein demonstrate activity in the learned helplessness assay for antidepressant/antianxiety activity. Examples 31, 44, 71 and 72, infra, demonstrate activity in the learned helplessness assay. In addition, compounds were tested for maximal intrinsic activity (IA), and were found to have measured IA's of negative 50% to positive 150% in the GTPγS assay described below, thus demonstrating a range of response from agonism (low percentages) to antagonism (high percentages).

The compounds described herein may be provided or delivered in a form suitable for oral use, for example in a tablet, lozenge, hard and soft capsule, aqueous solution, oily solution, emulsion, and suspension. The compounds may be also be provided for topical administration, for example, as a cream, ointment, gel, spray, or aqueous solutions, oily solutions, emulsions or suspensions. The compounds described herein may also be provided in a form suitable for nasal administration for example, as a nasal spray, nasal drops, or dry powder. The compositions may also be administered to the vagina or rectum in the form of a suppository. The compounds described herein may also be administered parentally, for example by intravenous, intravesicular, subcutaneous, or intramuscular injection or infusion. The compounds may be administered by insufflation (for example as a finely divided powder). The compounds may also be administered transdermally or sublingually.

The compositions of the invention may accordingly be obtained by conventional procedures using conventional pharmaceutical excipients, well known in the art. Thus, compositions intended for oral use may contain, for example, one or more coloring, sweetening, flavoring and/or preservative agents.

The amount of active ingredient that is combined with one or more excipients to produce a single dosage form will necessarily vary depending upon the host treated and the particular route of administration. The size of the dose for therapeutic or prophylactic purposes of a compound of the Formula I, Formula II, Formula III, Formula IV or Formula V will naturally vary according to the nature and severity of the conditions, the age and sex of the animal or patient and the route of administration, according to well known principles of medicine. Various assays and in vivo tests are known for determining the utility of the compounds in the disorders noted above and specifically as agonists and antagonists of $5HT_{1B}$ and $5HT_{1D}$.

The utility of the compounds for example to treat depression may be shown via a learned helplessness test in guinea pigs, which is used extensively as correlative to antidepressant activity in humans. The learned helplessness test may be carried out as follows: Seventy male Hartley guinea pigs, each weighing about 350–425 gm are fed ad lib, and are housed under a 12-hour light/dark cycle. The procedure consists of two phases: The induction phase and the avoidance training phase. In the induction phase, subjects are placed into standard shuttle cages (20 L×16 W×21 centimeters H) which are fitted with a grid floor. Electrical stimulation (1.25 mA, 10 sec duration) is delivered to the floor of the cage every 90-sec during 1 hour daily sessions. Subjects have no opportunity to escape or to avoid shocks. Induction is conducted for 2 consecutive days.

In avoidance training, testing is also conducted in the shuttle cages, except that the subjects are not returned to the same chamber in which induction had occurred. Additionally, all cages are fitted with a partition with an arch in the center of the cage, through which animals can pass between the left and right halves of the cage. The procedure employed is a standard shuttle avoidance procedure in which a compound, conditioned stimulus (a 10-sec presentation of a tone and turning on of a lamp on the side of the cage that the guinea pig was occupying) serves to indicate presentation of electrical current to the floor of the cage. Shock is presented for a 5 sec period, 5 sec after initiation of the conditioned stimulus. Entry into the opposite side of the shuttle cage via the arched partition prior to shock onset results in the end of the trial (avoidance response). If shock is delivered, entry into the opposite side of the cage results in termination of the shock and CS (escape). Reversal of learned helplessness in the induction subjects correlates to antidepressant activity of the test compound.

Avoidance training, 45-min in duration, is conducted on 2 consecutive days, beginning 48 hr after the final induction session. Seventy subjects are assigned to 1 of 6 groups of 11–12 animals. The groups are as follows:

1) No induction group. The subjects are placed into the shuttle cages but are not given inescapable shock, the animals are subsequently trained in the avoidance procedure and the vehicle is administered;
2) Induction vehicle control group;
3) Imipramine 17.8 mg/kg;
4) 0.3 mg/kg compounds;
5) 1 mg/kg compounds; and
6) 5 mg/kg compounds.

Groups 2–6 are given induction and avoidance training sessions. Injections are administered immediately following induction sessions and 1 hour prior to avoidance training sessions. A second injection is administered 7–8 hours following the first injection, for a total of 9 injections administered over 5 days. No injections are administered following the final avoidance training session.

Compounds of the present invention may be administered in a volume of 1 ml/kg bwt. Imipramine is dissolved in DI water. The compounds are dissolved in DI water, to which was added a few drops of lactic acid (pH 5.5). The vehicle control is DI water prepared with lactic acid to the same pH as the-treated groups.

The primary dependent variable is escape failure during avoidance training. 2-way analysis of variance (ANOVA) is used to assess overall treatment effect, with Dunn's post hoc analysis used to compare the vehicle-treated group with the drug-treated groups. The no-induction group is used to gauge whether learned helplessness is established, by comparison to the vehicle treated group.

An alternative method for determining the utility of the compounds of the present invention is to investigate the in vivo activity of the compounds using a guinea pig hypothermia test (J. Med. Chem., 41: 1218–1235 (1998)). Compounds that bind to $5\text{-}HT_{1B}$ receptors are known to be useful in treating disorders described above (e.g., depression, generalized anxiety, eating disorders, dementia, panic disorder, sleep disorders, gastrointestinal disorders, motor disorders, endocrine disorders, vasospasm and sexual dysfunction. While not wishing to be bound to any theory, it is believed that $5\text{-}HT_{1B}$ receptors on nerve terminals control the amount of release of s5-ht into the synapse. Thus, it can be shown that compounds of Formula I, Formula II, Formula IV and Formula V, and their pharmaceutically acceptable salts, are able to act as $5\text{-}HT_{1B}$ antagonists and block the agonist-induced effect of hypothermia (a drop in body temperature of about 2° C. observed within 0.5–1.5 hours following administration of a $5\text{-}HT_{1B}$ agonist) as a method for assessing whether the novel compounds are effective as antagonists at the $5\text{-}HT_{1B}$ receptor.

The hypothermia test is conducted as follows: A telethermometer fitted with a flexible probe will be used. The tip of the probe is immersed in a test tube containing a lubrication agent between usage. Core temperature is measured by inserting the probe into the rectum and by waiting for the temperature to stabilize, which occurs within the 20–60 seconds. Core temperature is measured once (pretest) prior to administration of the test substance in order to establish a baseline temperature for all animals. Guinea pigs are then dosed with the test substance (candidate 5-ht1b antagonist) either subcutaneously or intraperitoneally. In general, 30 min following dosing with antagonist, agonist is administered subcutaneously. The temperature is then recorded 30-, 60, 90-min following agonist. In some studies, in order to record time course of antagonist activity, up to 12 hours may be allowed to elapse between administration of antagonist and agonist. The drugs may either be injected subcutaneously, intraperitoneally or orally (using a flexible plastic gavage tube, or a stainless steel gavage tube). In addition, animals may be observed on the days following drug administration in order to monitor for unexpected toxicity. The body temperature of the guinea pigs is recorded separately for each guinea pig at each test time point, and submitted to a ANOVA with one between subjects factor: dose, and one within subject factor: time. Following a significant two-way interaction (p<0.05), Dunnett's t-test is performed to compare the drug treatment with either the saline or the effects of treatment with the hypothermic agent.

Male Guinea Pig (Dunkin-Hartley), maximum 3 animals per cage, are used. The animals may be grouped in sets of 5 during testing. The animals will not be deprived of food or water during their time in the laboratory. The routes of administration are: S.C., I.P., P.O. The maximum dose (volume) is 2 ml/kg s.c. or i.p., 5 ml/kg P.O. three times daily.

This method may function as a primary in vivo screen for compounds having an affinity for $5\text{-ht}_{1b}$ receptors as a determination of antagonist activity. Each experiment may consist of separate groups of 5 subjects per treatment level. One group is given vehicle prior to agonist administration and may serve as the control group, i.e., hypothermia will be unaltered by introduction of an antagonist. The other groups are administered different doses of antagonist prior to agonist administration, but no more than 5 groups are tested at a time. In order to determine full dose effect functions for compounds (to determine drug potency) 4–6 doses of each compound are evaluated. That results in about 25–35 animals per drug to be evaluated. Dose-response curves are generated and ED50 values are determined. ED50 values for compounds of the present invention range from 0.006–5.5 mg/kg.

Other assays that may be used to measure for example affinity of compounds of the present invention for $5HT_{1B}$ and $5HT_{1D}$ receptors are described in J. Med. Chem 41:1218–1235, 1228 (1998) and J. Med. Chem 42:4981–5001, (1999) and incorporated by reference herein. These assays may be used with some modifications: Frozen membrane preparations of a stably transfected chinese hamster ovary (CHO) cell line expressing $5\text{-HT}_{1B}$ receptors and $5\text{-HT}_{1D}$ receptors are thawed rapidly, briefly vortexed, and diluted in assay buffer (AB) containing 50 mM Tris-HCl, 4 mM $MgCl_2$, 4 mM $CaCl_2$, 1 mM EDTA, and adjusted to pH 7.4 with NaOH. Final protein concentrations are—0.185 mg/ml for $5\text{-HT}_{1B}$, and 0.4 mg/ml for $5\text{-HT}_{1D}$ membranes. Test compounds are evaluated in competition assays using [$^3$H]-GR125743 (Amersham). The ligand concentration in both assays was 0.27 nM. Kd for [$^3$H]-GR125743 may vary from 0.15 mM to 0.25 nM. The $5\text{-HT}_{1B}$ and $5\text{-HT}_{1D}$ assays are performed simultaneously on one 96-well assay plate, one drug/compound per plate. Ten serial dilutions (1 uM to 4 pM, final concentration) of compound are prepared in DMSO from 10 mM stock solutions. Incubation mixtures are prepared in quadruplicate in 96-deep well assay plates (Matrix 1 ml). Final assay volumes per well are 10 µl compound/nonspecific; 100 µl membranes; 100 µl [3H]-GR125743; and 790 µl AB. Specific binding is defined by using 10 uM Methiothepine. The assay plates are shaken for 5 min., and then incubated for an additional 55 min. Then the assay plates are filtered through Beckman GF/B filters (soaked >2 hrs. in PEI) using a Packard Filtermate 196. Filters are washed 2× with 1 ml ice-cold wash buffer (5 mM Tris-HCl—$pH_{7.4}$ with NaOH). After the filters are dried, 35 µl of Microscint20 is added to each well. The plates are then counted on a Packard TopCount to determine CPM's per well. Ki values are determined for each test compound utilizing the graphic and analytical software package, GraphPad Prism. Compounds are then ranked in order of potency, and selectivity for $5\text{-HT}_{1B}$ over $5\text{-HT}_{1D}$ receptors.

A method that may be used to determine a compound's affinity for $5\text{-HT}_{1B}$ and $5HT_{1D}$ receptors is a guinea pig cortical test. This assay is described in detail by Roberts, et al, Br. J. Pharmacol., 1996, 117, 384–388, which is incorporated by reference herein. The test is carried out as follows: Guinea pigs are decapitated and the cortici is dissected out, weighed and homogenized in 50 mM Tris-HCl, pH 7.7 with an Ultra-Turrax followed by centrifugation for 10 min at 48000×g and 5° C. The pellet is resuspended and recentrifuged. The final pellet is suspended in 0.32 M sucrose buffer to a concentration of 0.5 g original wet weight per mL and stored frozen at −70° C. The radioligand binding assay is carried out as follows: [$^3$H]GR125743 saturation studies are tested in duplicate with 3–4 mg w.w. per tube in 5 mL buffer (50 mM Tris, 4 mM CaCl2, 4 mM MgCl2 and 1 mM EDTA at pH 7.7), and a concentration range of 0.012–2 nM (10–12 concentrations) for the radioligand. Non-specific binding is determined in the presence of 10 mM methiothepin. In competition experiments 4–8 mg w.w. per tube and a radioligand concentration of 0.2 nM are used with 10–12 concentrations of the competing drug. The assays are run for 2–4 hours at 30° C. and terminated by rapid filtration through Whatman GF/B filters (pretreated with 0.1% polyethyleneimine) using a Brandel cell harvester. Bovine serum albumin (0.1%) is added to the washing buffer to reduce non-specific binding. Data from the experiments may be analyzed using the iterative non-linear curve-fitting program LIGAND. The $K_d$ values obtained from the saturation studies are used in the calculation of the Ki values by the LIGAND program. The $K_d$ value of [$^3$H]GR125743 may result in a measurement of 46±4 pM and the $B_{max}$ in a measurement of 4.9±0.2 pmol/g w.w.

A GTPγS binding assay may used to determine whether a compound is a $5HT_{1B}$ or $5HT_{1D}$ agonist or antagonist. One assay available measures agonist stimulated GTP binding for example as set forth by Lazareno, S. (1999) *Methods in Molecular Biology* 106: 231–245. Membrane preparations of a stably transfected CHO cell line expressing human $5\text{-HT}_{1B}$ receptors are purchased for example from Unisyn, Hopkinton, Mass. Frozen membranes are thawed, briefly sonicated, and diluted to 167 µg/ml protein in assay buffer containing 20 mM HEPES, 100 mM NaCl, 1 mM $MgCl_2$ and 1 µM GDP, pH adjusted to 7.4 with NaOH. Diluted membranes are briefly homogenized with a Polytron and allowed to equilibrate at room temperature for at least 15 minutes before use. Serial dilutions (10 µM to 1 pM, final concentration) of test compounds are prepared in buffer with and without 100 nM 5-HT (final concentration) from 10 mM DMSO stock solutions. Incubation mixtures are prepared in quadruplicate in 96-well, deep-well plates and consisted of 180 µL of membranes (30 µg protein) and 40 µL of compound with or without 5-HT. After an incubation period of 15 minutes at room temperature, 20 µL of [$^{35}$S]GTPγS (NEN; 100 pM final concentration) is added to begin the assay. Mixtures are shaken for 2 minutes and incubated at room temperature for an additional 28 minutes. The reaction is stopped by rapid filtration through Beckman GF/B glass fiber filters using a 96-well Packard cell harvester. Filters are washed four times with 1 mL ice-cold water. The filter plates are nominally dried and 30 µL of scintillation cocktail (MicroScint 40, Packard) is added to each well. CPMs for each well is determined using a TopCount Scintillation Counter (Packard). Maximum stimulation of [$^{35}$S]GTPγS binding is defined in the presence of 100 nM 5-HT. Basal [35S]GTPγS binding is defined in buffer alone. IC50 values are defined as the concentration of compound at which 50% of the 100 nM 5-HT response [was] obtained. Maximal intrinsic activity (IA) of a compound is defined as the percent maximal 5-HT-induced stimulation by 10 μM compound in the absence of 5-HT. As an inter-assay standard, a concentration response curve of 5-HT (1 μM to 1 pM final) in the absence of compounds was included in each assay and an $EC_{50}$ was determined.

Preferred compounds of the present invention include, but are not limited to, the following compositions listed in Table 1 on the following pages.

TABLE 1

Compounds

| Example # | Structure | Name |
|---|---|---|
| 1 | 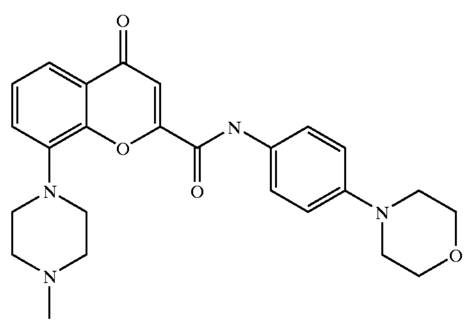 | 8-(4-methyl-1-piperazinyl)-N-[4-(4-morpholinyl)phenyl]-4-oxo-4H-chromene-2-carboxamide |
| 2 | 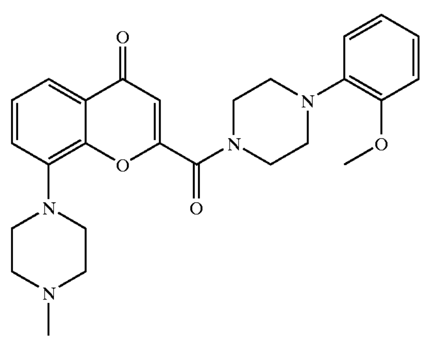 | 2-{1-[4-(2-Methoxy-phenyl)-piperazin-1-yl]-methanoyl}-8-(4-methyl-piperazin-I-yl)-chromen-4-one |
| 3 | 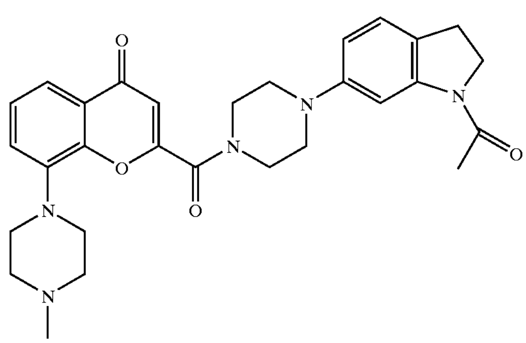 | 2-{1-[4-(1-Acetyl-2,3-dihydro-1H-indol-6-yl)-piperazin-1-yl]-methanoyl}-8-(4-methyl-piperazin-1-yl)-chromen-4-one |

TABLE 1-continued

Compounds

| Example # | Structure | Name |
|---|---|---|
| 4 | 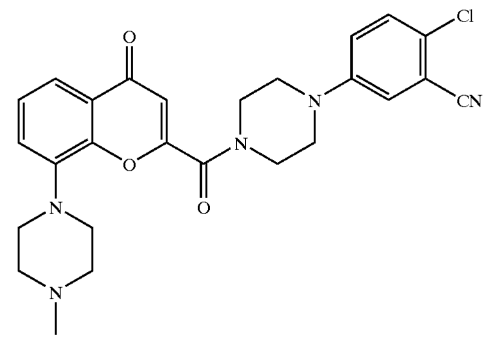 | 2-Chloro-5-(4-{1-[8-(4-methyl piperazin-1-yl)-4-oxo-4H-chromen-2-yl]-methanoyl}-piperazin-1-yl)-benzonitrile |
| 5 | 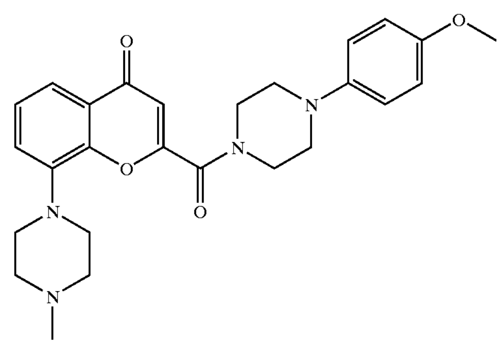 | 2-{1-[4-(4-Methoxy-phenyl)-piperazin-1-yl]-methanoyl}-8-(4-methyl-piperazin-1-yl)-chromen-4-one |
| 6 | 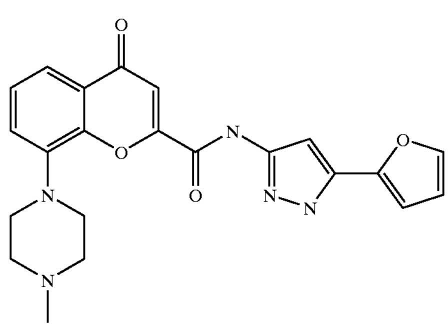 | 8-(4-Methyl-piperazin-1-yl)-4-oxo-4H-chromene-2-carboxylic acid (5-furan-2-yl-1H-pyrazol-3-yl)-amide |
| 7 | 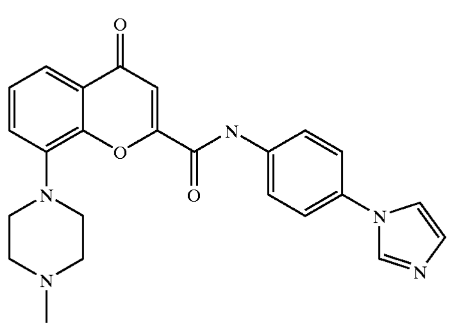 | 8-(4-Methyl-piperazin-1-yl)-4-oxo-4H-chromene-2-carboxylic acid (4-imidazol-1-yl-phenyl)-amide |

TABLE 1-continued

Compounds

| Example # | Structure | Name |
|---|---|---|
| 8 | 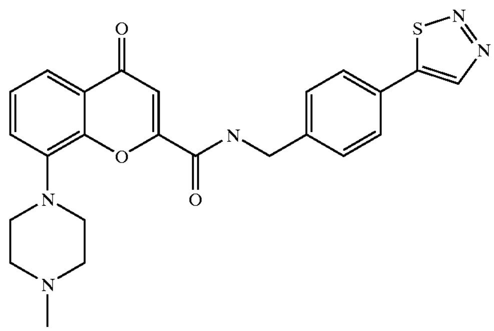 | 8-(4-Methyl-piperazin-1-yl)-4-oxo-4H-chromene-2-carboxylic acid (4-[1,2,3]thiadiazol-5-yl-phenyl)-amide |
| 9 | 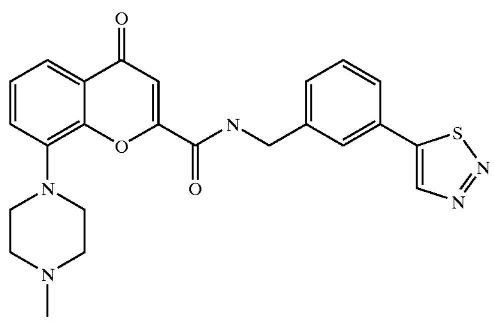 | 8-(4-Methyl-piperazin-1-yl)-4-oxo-4H-chromene-2-carboxylic acid 4-[1,2,3]thiadiazol-5-yl-benzylamide |
| 10 | 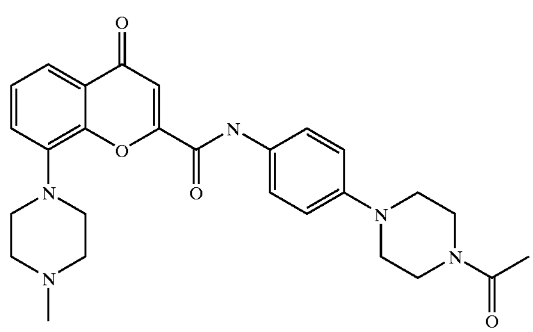 | 8-(4-Methyl-piperazin-1-yl)-4-oxo-4H-chromene-2-carboxylic acid [4-(4-acetyl-piperazin-1-yl)-phenyl]-amide |
| 11 | 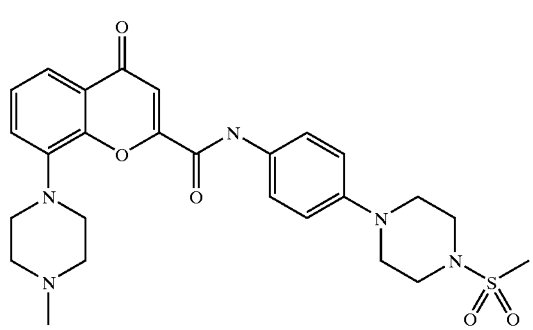 | 8-(4-Methyl-piperazin-1-yl)-4-oxo-4H-chromene-2-carboxylic acid [4-(4-methanesulfonyl-piperazin-1-yl)-phenyl]-amide |

TABLE 1-continued

Compounds

| Example # | Structure | Name |
|---|---|---|
| 12 | 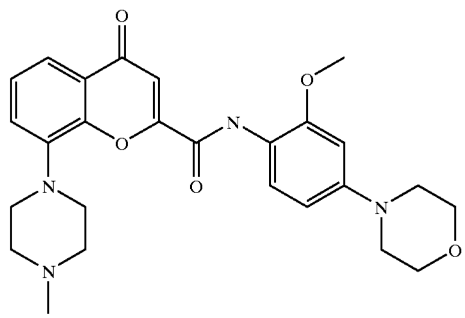 | 8-(4-Methyl-piperazin-1-yl)-4-oxo-4H-chromene-2-carboxylic acid (2-methoxy-4-morpholin-4-yl-phenyl)-amide |
| 13 | 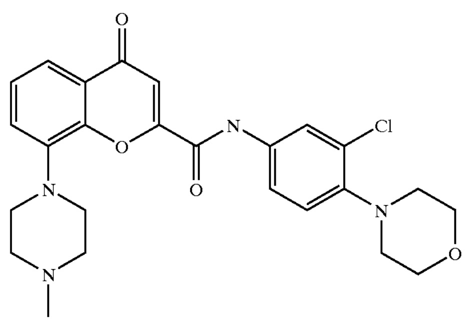 | 8-(4-Methyl-piperazin-1-yl)-4-oxo-4H-chromene-2-carboxylic acid (3-chloro-4-morpholin-4-yl-phenyl)-amide |
| 14 | 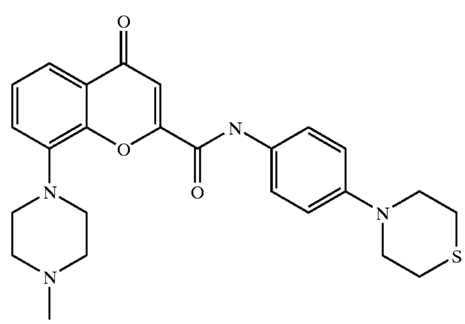 | 8-(4-Methyl-piperazin-1-yl)-4-oxo-4H-chromene-2-carboxylic acid (4-thiomorpholin-4-yl-phenyl)-amide |
| 15 | 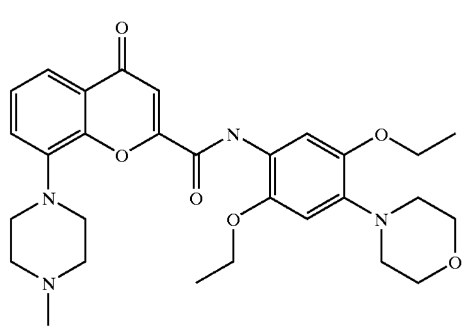 | 8-(4-Methyl-piperazin-1-yl)-4-oxo-4H-chromene-2-carboxylic acid (2,5-diethoxy-4-morpholin-4-yl-phenyl)-amide |

TABLE 1-continued

Compounds

| Example # | Structure | Name |
|---|---|---|
| 16 | 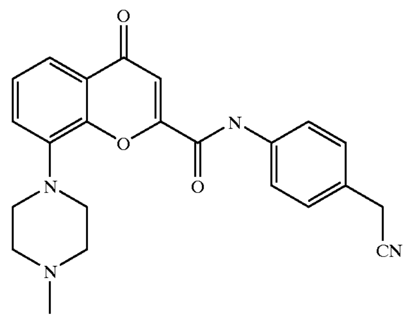 | 8-(4-Methyl-piperazin-1-yl-4-oxo-4H-chromene-2-carboxylic acid (4-cyanomethyl-phenyl)-amide |
| 17 | 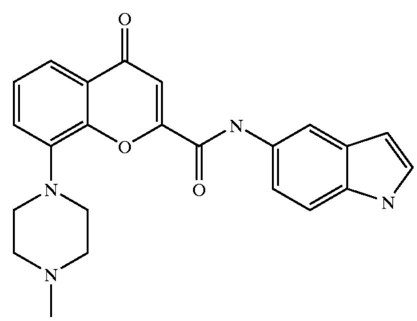 | 8-(4-Methyl-piperazin-1-yl)-4-oxo-4H-chromene-2-carboxylic acid (1H-indol-5-yl)-amide |
| 18 | 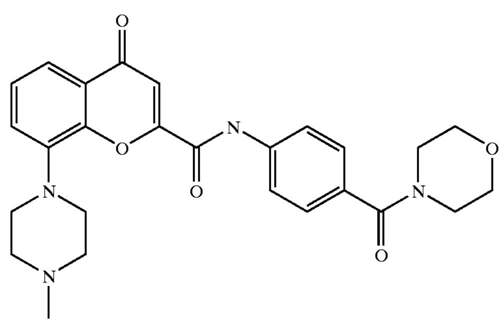 | 8-(4-Methyl-piperazin-1-yl)-4-oxo-4H-chromene-2-carboxylic acid [4-(1-morpholin-4-yl-methanoyl)-phenyl]-amide |
| 19 | 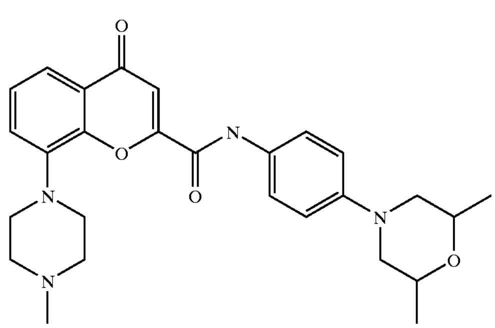 | 8-(4-Methyl-piperazin-1-yl)-4-oxo-4H-chromene-2-carboxylic acid [4-(2,6-dimethyl-morpholin-4-yl)-phenyl]-amide |

TABLE 1-continued

Compounds

| Example # | Structure | Name |
|---|---|---|
| 20 | 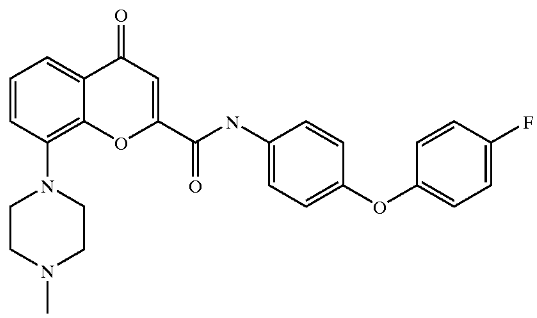 | 8-(4-Methyl-piperazin-1-yl)-4-oxo-4H-chromene-2-carboxylic acid [4-(4-fluoro-phenoxy)-phenyl]-amide |
| 21 | 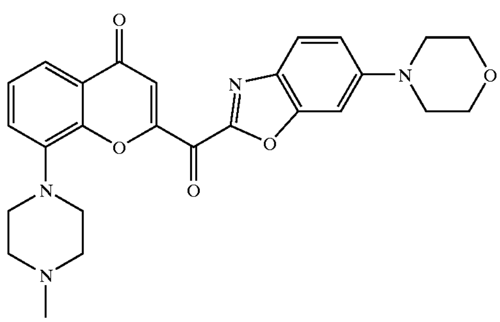 | 8-(4-Methyl-piperazin-1-yl)-2-(6-morpholin-4-yl-benzooxazol-2-yl)-chromen-4-one |
| 22 | 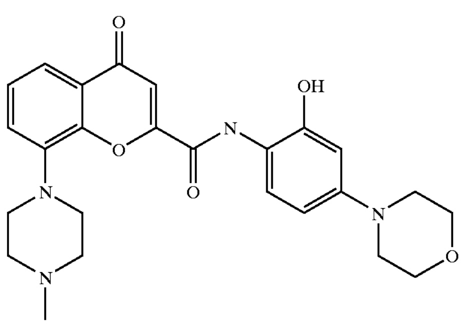 | 8-(4-Methyl-piperazin-1-yl)-4-oxo-4H-chromene-2-carboxylic acid (2-hydroxy-4-morpholin-4-yl-phenyl) amide |
| 23 | 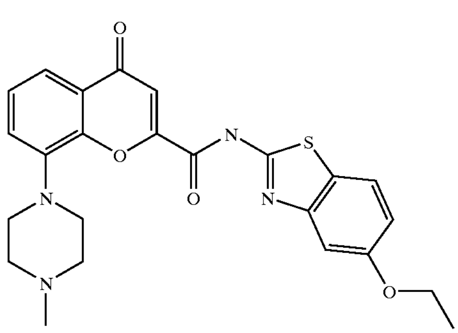 | 8-(4-Methyl-piperazin-1-yl)-4-oxo-4H-chromene-2-carboxylic acid (5-ethoxy-benzothiazol-2-yl)-amide |

TABLE 1-continued

Compounds

| Example # | Structure | Name |
|---|---|---|
| 24 | 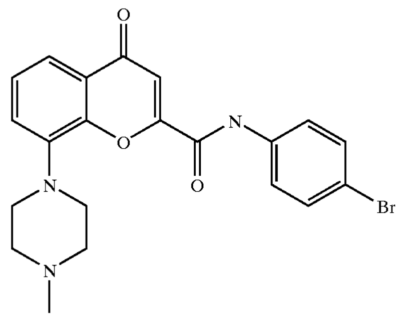 | 8-(4-Methyl-piperazin-1-yl)-4-oxo-4H-chromene-2-carboxylic acid (4-bromo-phenyl)-amide |
| 25 | 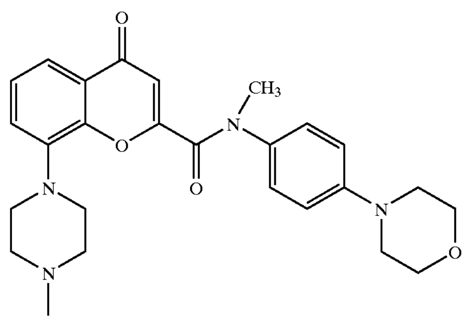 | 8-(4-Methylpiperazin-1-yl)-4-oxo-4H-chromene-2-carboxylic acid methyl-(4-morpholin-4-yl-phenyl)amide |
| 26 | 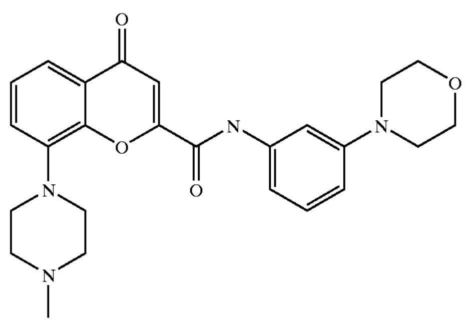 | 8-(4-Methyl-piperazin-1-yl)-4-oxo-4H-chromene-2-carboxylic acid (3-morpholin-4-yl-phenyl)-amide |
| 27 | 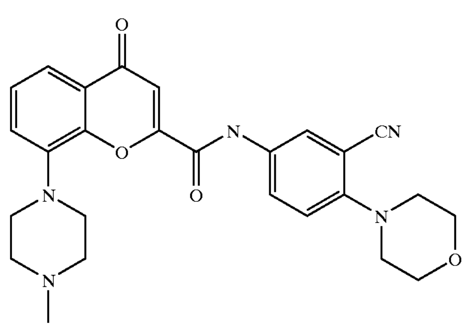 | 8-(4-Methyl-piperazin-1-yl)-4-oxo-4H-chromene-2-carboxylic acid (3-cyano-4-morpholin-4-yl-phenyl)amide |

TABLE 1-continued

Compounds

| Example # | Structure | Name |
|---|---|---|
| 28 | | 8-(4-Methyl-piperazin-1-yl)-4-oxo-4H-chromene-2-carboxylic acid (3-fluoro-4-morpholin-4-yl-phenyl)-amide |
| 29 | | 4-[4-({1-[8-(4-Methyl-piperazin-1-yl)-4-oxo-4H-chromen-2-yl]-methanoyl}-amino)-phenyl]-piperazine-1-carboxylic acid tert-butyl ester |
| 30 | | 8-(4-Methyl-piperazin-1-yl)-4-oxo-4H-chromene-2-carboxylic acid (4-piperazin-1-yl-phenyl)-amide |
| 31 | | 6-Methoxy-8-(4-methyl-piperazin-1-yl)-4-oxo-4H-chromene-2-carboxylic acid (4-morpholin-4-yl-phenyl)-amide |

TABLE 1-continued

Compounds

| Example # | Structure | Name |
|---|---|---|
| 32 | 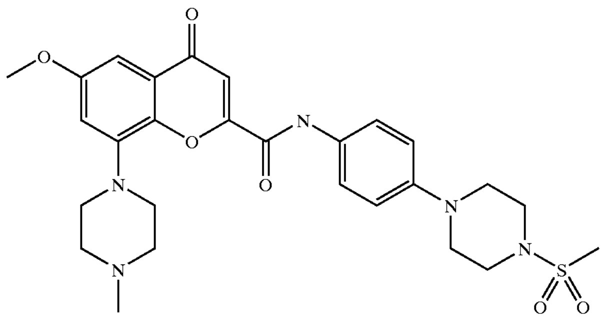 | 6-Methoxy-8-(4-methyl-piperazin-1-yl)-4-oxo-4H-chromene-2-carboxylic acid [4-(4-methanesulfonyl-piperazin-1-yl)-phenyl]-amide |
| 33 | 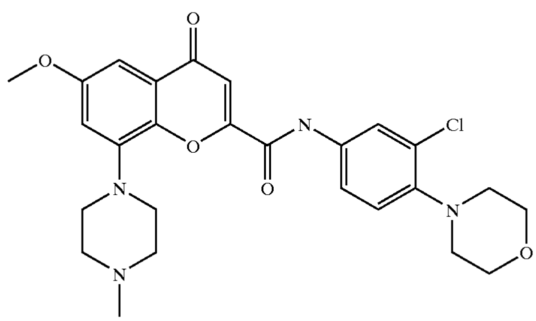 | 6-Methoxy-8-(4-Methyl-piperazin-1-yl)-4-oxo-4H-chromene-2-carboxylic acid (3-chloro-4-morpholin-4-yl-phenyl)-amide |
| 34 | 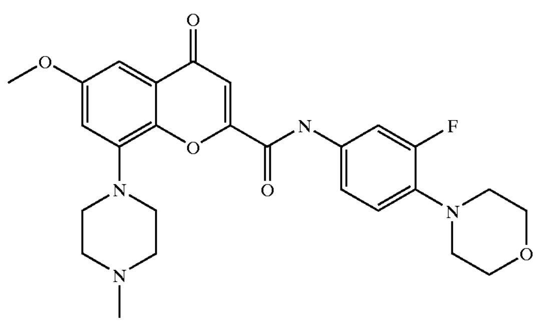 | 6-Methoxy-8-(4-methyl-piperazin-1-yl)-4-oxo-4H-chromene-2-carboxylic acid (3-fluoro-4-morpholin-4-yl-phenyl)-amide |
| 35 | 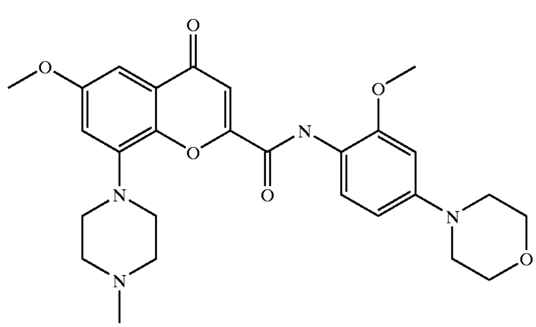 | 6-Methoxy-8-(4-methyl-piperazin-1-yl)-4-oxo-4H-chromene-2-carboxylic acid (2-methoxy-4-morpholin-4-yl-phenyl)-amide |

TABLE 1-continued

Compounds

| Example # | Structure | Name |
|---|---|---|
| 36 | 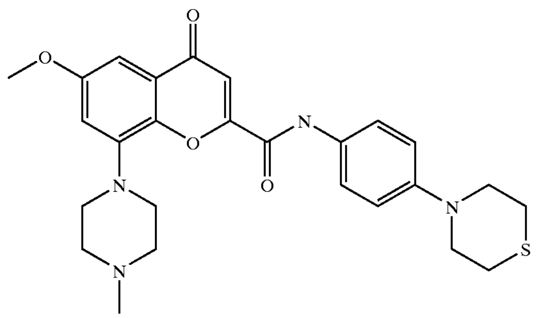 | 6-Methoxy-8-(4-methyl-piperazin-1-yl)-4-oxo-4H-chromene-2-carboxylic acid (4-thiomorpholin-4-yl-phenyl)-amide |
| 37 | 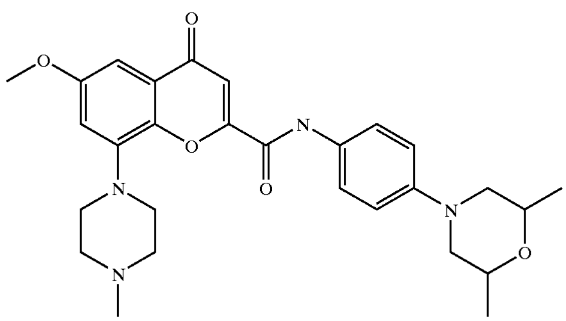 | 6-Methoxy-8-(4-methyl-piperazin-1-yl)-4-oxo-4H-chromene-2-carboxylic acid [4-(2,6-dimethyl-morpholin-4-yl)-phenyl]-amide |
| 38 | 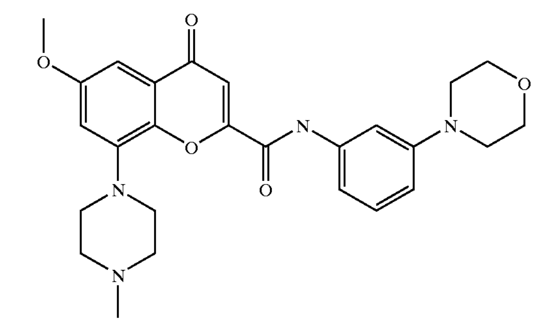 | 6-Methoxy-8-(4-methyl-piperazin-1-yl)-4-oxo-4H-chromene-2-carboxylic acid (3-morpholin-4-yl-phenyl)-amide |
| 39 | 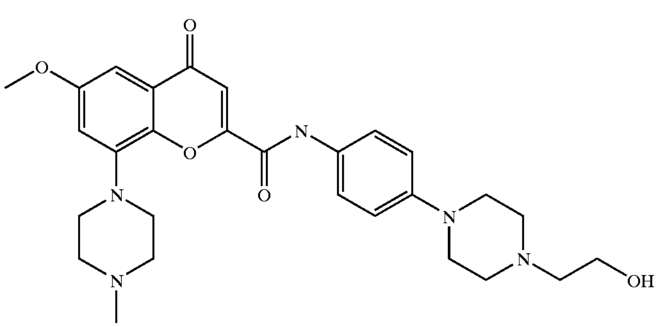 | 6-Methoxy-8-(4-methyl-piperazin-1-yl)-4-oxo-4H-chromene-2-carboxylic acid {4-[4-(2-hydroxy-ethyl)-piperazin-1-yl]-phenyl}-amide |

TABLE 1-continued

Compounds

| Example # | Structure | Name |
|---|---|---|
| 40 | 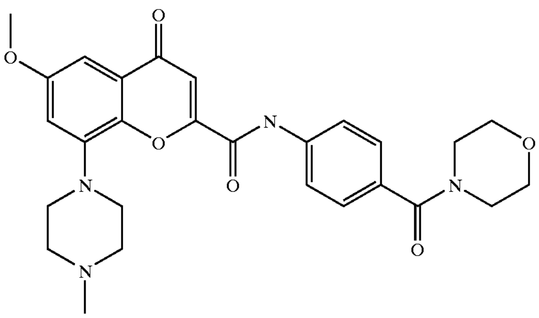 | 6-Methoxy-8-(4-methyl-piperazin-1-yl)-4-oxo-4H-chromene-2-carboxylic acid [4-(1-morpholin-4-yl-methanoyl)-phenyl]-amide |
| 41 | 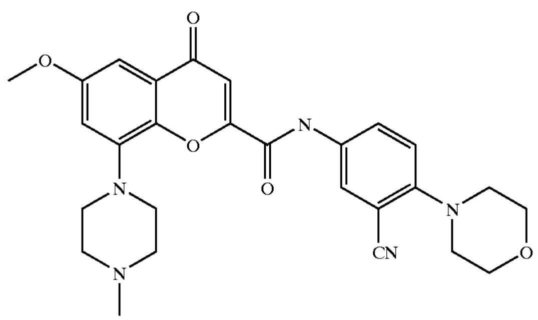 | 6-Methoxy-8-(4-methyl-piperazin-1-yl_-4-oxo-4H-chromene-2-carboxylic acid (3-cyano-4-morpholin-4-yl-phenyl)-amide |
| 42 | 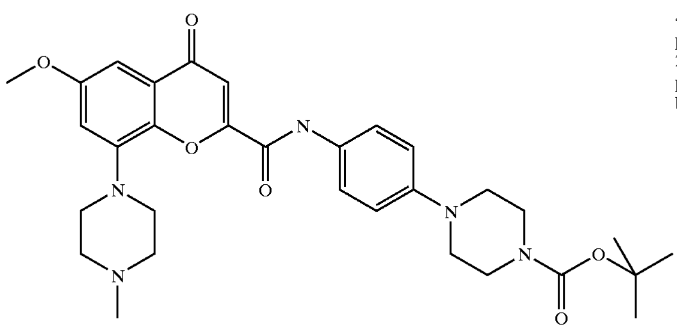 | 4-[4-({1-[6-Methoxy-8-(4-methyl-piperazin-1-yl)-4-oxo-4H-chromen-2-yl]-methanoyl}-amino)-phenyl]-piperazine-1-carboxylic acid tert-butyl ester |
| 43 | 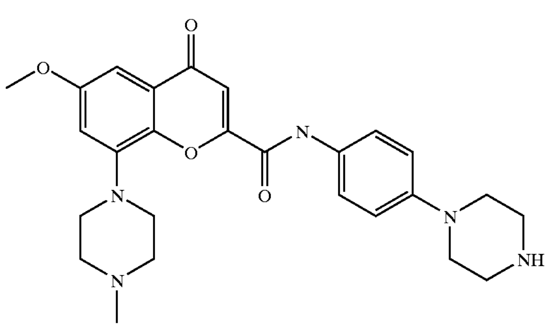 | 6-Methoxy-8-(4-methyl-piperazin-1-yl)-4-oxo-4H-chromene-2-carboxylic acid (4-piperazin-1-yl-phenyl)-amide |

TABLE 1-continued

Compounds

| Example # | Structure | Name |
|---|---|---|
| 44 | 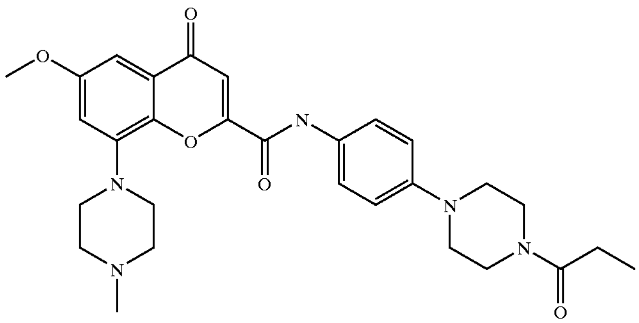 | 6-Methoxy-8-(4-methyl-piperazin-1-yl)-4-oxo-4H-chromene-2-carboxylic acid [4-(4-propionyl-piperazin-1-yl)-phenyl]-amide |
| 45 | 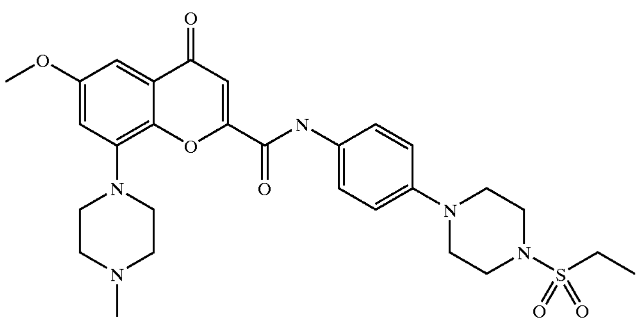 | 6-Methoxy-8-(4-methyl-piperazin-1-yl)-4-oxo-4H-chromene-2-carboxylic acid [4-(4-ethane sulfonyl-piperazin-1-yl)-phenyl]-amide |
| 46 | 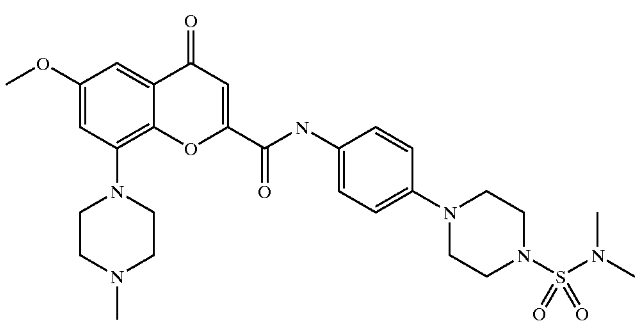 | 6-Methoxy-8-(4-methyl-piperazin-1-yl)-4-oxo-4H-chromene-2-carboxylic acid [4-(4-dimethyl sulfamoyl-piperazin-1-yl)-phenyl]-amide |
| 47 | 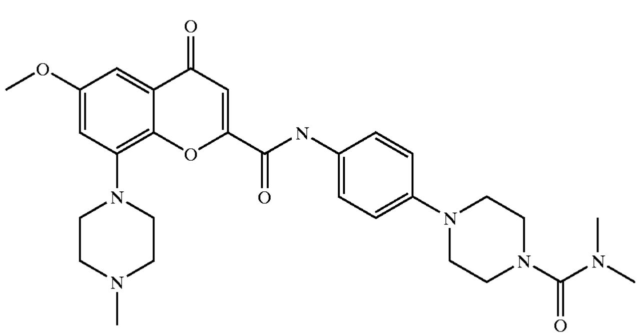 | 4-[4-({1-[6-Methoxy-8-(4-methyl-piperazin-1-yl)-4-oxo-4H-chromen-2-yl]-methanoyl}-amino)-phenyl]-piperazine-1-carboxylic acid dimethylamide |

TABLE 1-continued

Compounds

| Example # | Structure | Name |
|---|---|---|
| 48 | 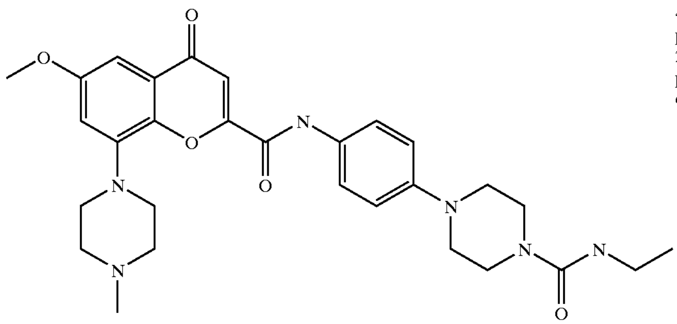 | 4-[4-({1-[6-Methoxy-8-(4-methyl-piperazin-1-yl)-4-oxo-4H-chromen-2-yl]-methanoyl}-amino)-phenyl]-piperazine-1-carboxylic acid ethylamide |
| 49 | 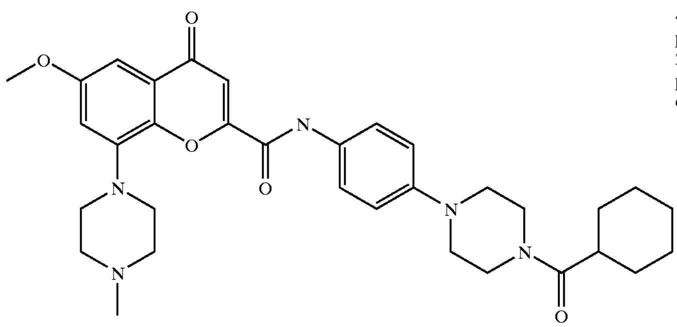 | 4-[4-({1-6-Methoxy-8-(4-methyl-piperazin-1-yl)-4-oxo-4H-chromen-2-yl]-methanoyl}-amino)-phenyl]-piperazine-1-carboxylic acid cyclohexylamide |
| 50 | 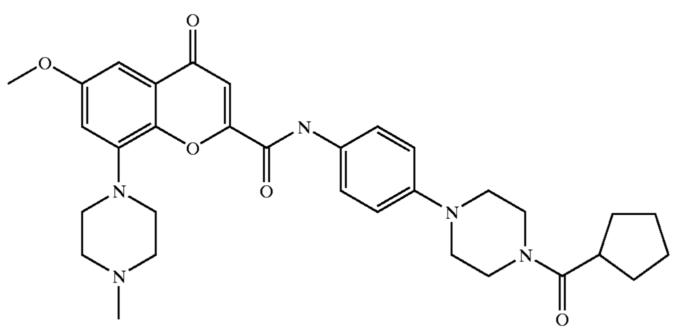 | 4-[4-({1-[6-Methoxy-8-(4-methyl-piperazin-1-yl)-4-oxo-4H-chromen-2-yl]-methanoyl}-amino)-phenyl]-piperazine-1-carboxylic acid cyclopentylamide |
| 51 | 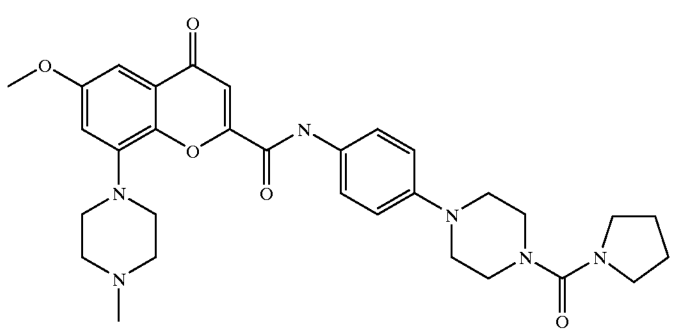 | 6-Methoxy-8-(4-methyl-piperazin-1-yl)-4-oxo-4H-chromene-2-carboxylic acid {4-[4-(1-pyrrolidin-1-yl-methanoyl)-piperazin-1-yl]-phenyl}-amide |

TABLE 1-continued

Compounds

| Example # | Structure | Name |
|---|---|---|
| 52 | 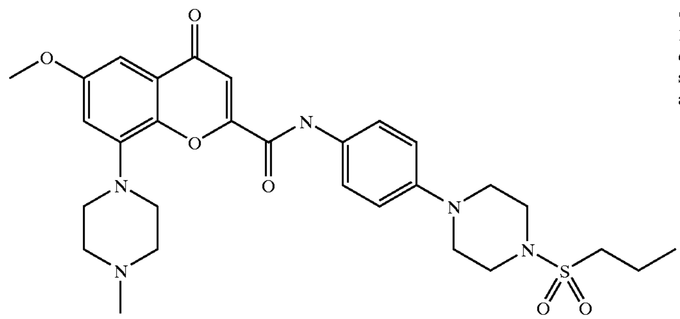 | 6-Methoxy-8-(4-methyl-piperazin-1-yl)-4-oxo-4H-chromene-2-carboxylic acid {4-[4-(propane-2-sulfonyl)-piperazin-1-yl]-phenyl}-amide |
| 53 | 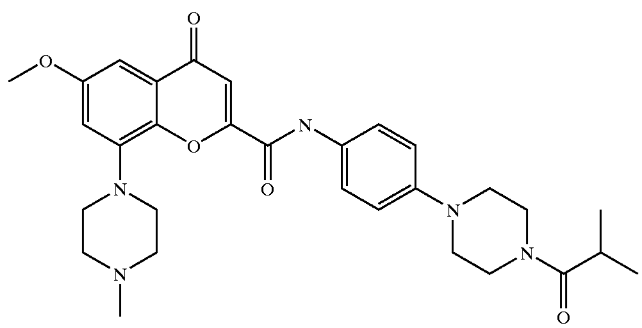 | 6-Methoxy-8-(4-methyl-piperazin-1-yl)-4-oxo-4H-chromene-2-carboxylic acid {4-[4-(2-methyl-propanoyl)-piperazin-1-yl]-phenyl}-amide |
| 54 | 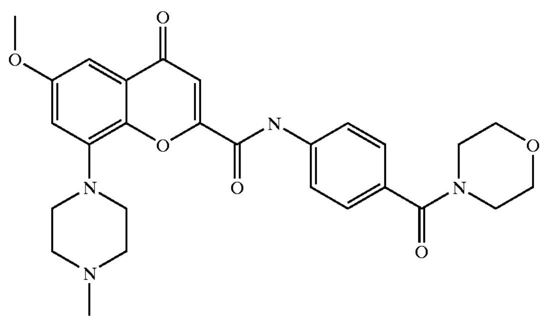 | 6-Methoxy-8-(4-methyl-piperazin-1-yl)-4-oxo-4H-chromene-2-carboxylic acid {4-[4-(1-morpholin-4-yl-methanoyl)-piperazin-1-yl]-phenyl}-amide |
| 55 | 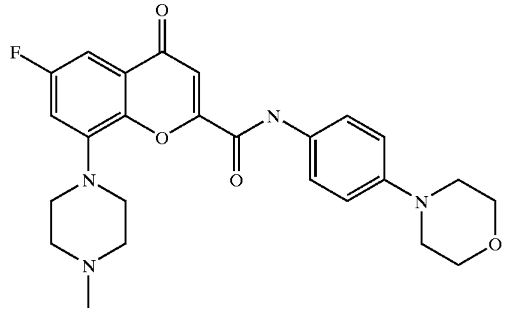 | 6-Fluoro-8-(4-methyl-piperazin-1-yl)-4-oxo-4H-chromene-2-carboxylic acid (4-morpholin-4-yl-phenyl)-amide |

TABLE 1-continued

Compounds

| Example # | Structure | Name |
|---|---|---|
| 56 | 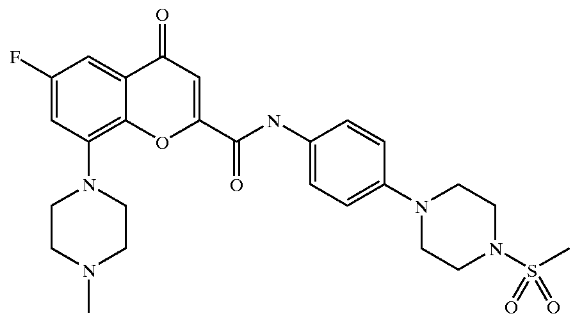 | 6-Fluoro-8-(4-methyl-piperazin-1-yl)-4-oxo-4H-chromene-2-carboxylic acid [4-(4-methanesulfonyl-piperazin-1-yl)-phenyl]-amide |
| 57 | 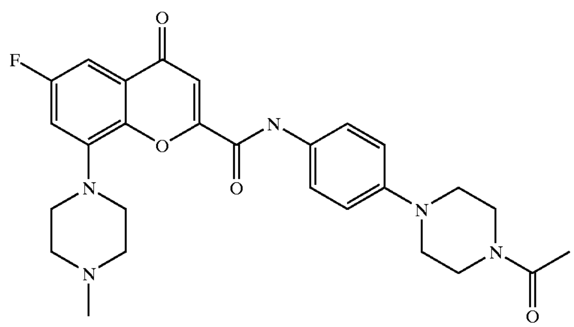 | 6-Fluoro-8-(4-methyl-piperazin-1-yl)-4-oxo-4H-chromene-2-carboxylic acid [4-(4-acetyl-piperazin-1-yl)-phenyl]-amide |
| 58 | 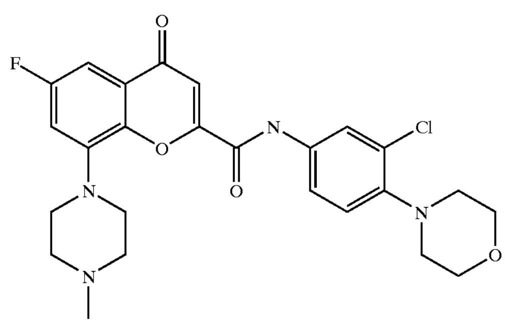 | 6-Fluoro-8-(4-methyl-piperazin-1-yl)-4-oxo-4H-chromene-2-carboxylic acid (3-chloro-4-morpholin-4-yl-phenyl)-amide |
| 59 | 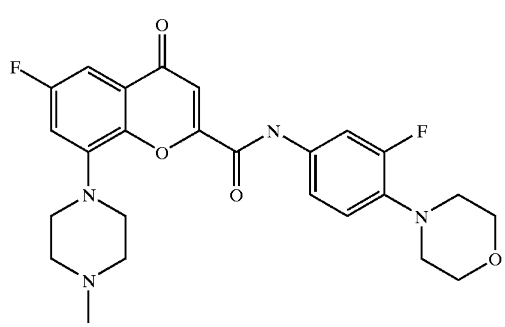 | 6-Fluoro-8-(4-methyl-piperazin-1-yl)-4-oxo-4H-chromene-2-carboxylic acid (3-fluoro-4-morpholin-4-yl-phenyl)-amide |

TABLE 1-continued

Compounds

| Example # | Structure | Name |
|---|---|---|
| 60 | | 6-Fluoro-8-(4-methyl-piperazin-1-yl)-4-oxo-4H-chromene-2-carboxylic acid (3-cyano-4-morpholin-4-yl-phenyl)-amide |
| 61 | | 6-Fluoro-8-(4-methyl-piperazin-1-yl)-4-oxo-4H-chromene-2-carboxylic acid [4-(1-morpholin-4-yl-methanoyl)-phenyl]-amide |
| 62 | | 6-Methyl-8-(4-methyl-piperazin-1-yl)-4-oxo-4-H-chromene-2-carboxylic acid (4-morpholin-4-yl-phenyl)-amide |
| 63 | | 6-Methyl-8-(4-methyl-piperazin-1-yl)-4-oxo-4H-chromene-2-carboxylic acid [4-(1-morpholin-4-yl-methanoyl)-phenyl]-amide |

TABLE 1-continued

Compounds

| Example # | Structure | Name |
|---|---|---|
| 64 | 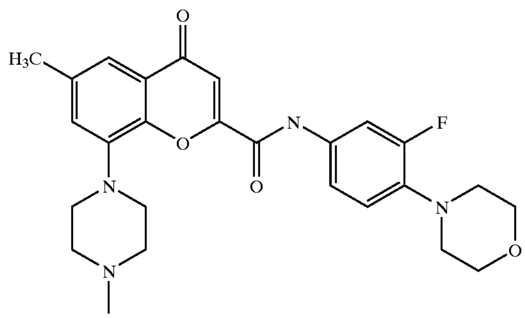 | 6-Methyl-8-(4-methyl-piperazin-1-yl)-4-oxo-4H-chromene-2-carboxylic acid (3-fluoro-4-morpholin-4-yl-phenyl)-amide |
| 65 | 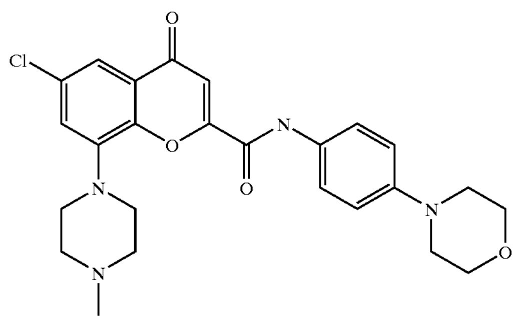 | 6-Chloro-8-(4-methyl-piperazin-1-yl)-4-oxo-4H-chromene-2-carboxylic acid (4-morpholin-4-yl-phenyl)-amide |
| 66 | 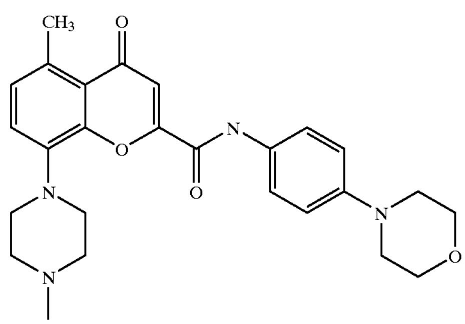 | 5-Methyl-8-(4-methyl-piperazin-1-yl)-4-oxo-4H-chromene-2-carboxylic acid (4-morpholin-4-yl-phenyl)-amide |
| 67 | 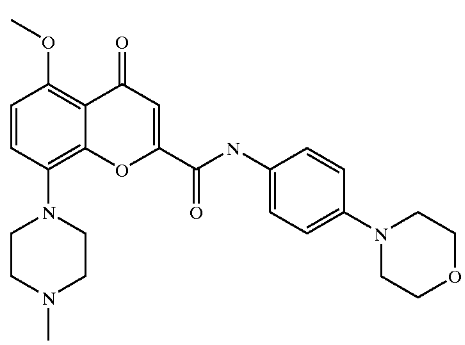 | 5-Methoxy-8-(4-methyl-piperazin-1-yl)-4-oxo-4H-chromene-2-carboxylic acid (4-morpholin-4-yl-phenyl)-amide |

TABLE 1-continued

Compounds

| Example # | Structure | Name |
|---|---|---|
| 68 | 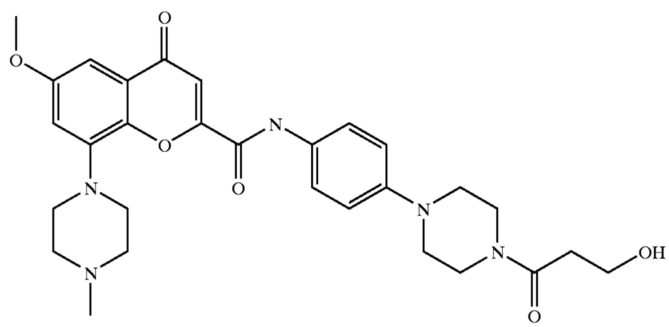 | 6-Methoxy-8-(4-methyl-piperazin-1-yl)-4-oxo-4H-chromene-2-carboxylic acid {4-[4-(3-hydroxy-propanoyl)-piperazin-1-yl]-phenyl}-amide |
| 69 | 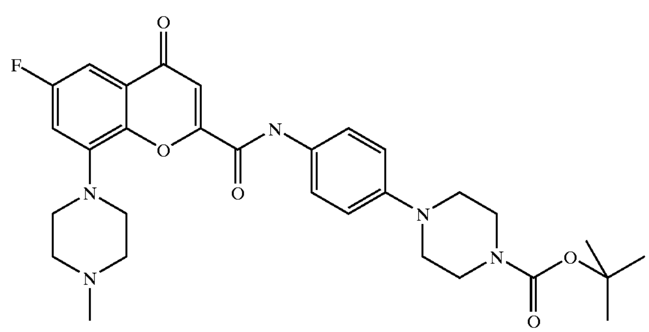 | 4-[4-({1-[6-Fluoro-8-(4-methyl-piperazin-1-yl)-4-oxo-4H-chromen-2-yl]-methanoyl}-amino)-phenyl]-piperazine-1-carboxylic acid tert-butyl ester |
| 70 | 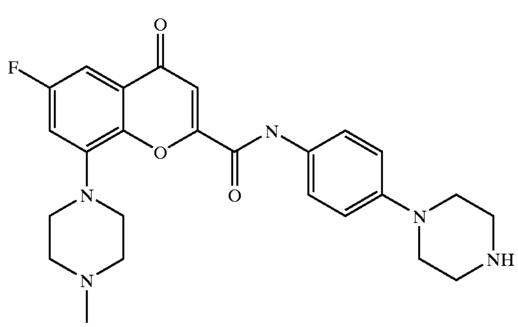 | 4-[4-({1-[6-Fluoro-8-(4-methyl piperazin-1-yl)-4-oxo-4H-chromene-2-carboxylic acid (4-piperazin-1-yl-phenyl)-amide |
| 71 | 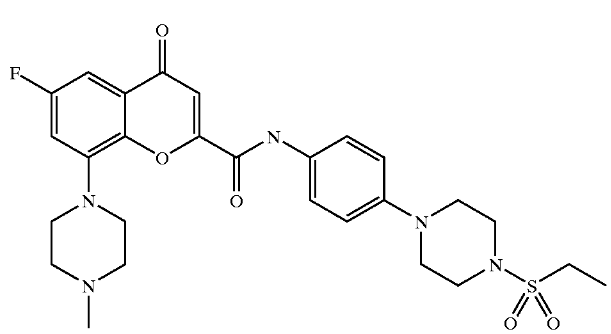 | 6-Fluoro-8-(4-methyl-piperazin-1-yl)-4-oxo-4H-chromene-2-carboxylic acid [4-(4-ethane sulfonyl-piperazin-1-yl)-phenyl]-amide |

TABLE 1-continued

Compounds

| Example # | Structure | Name |
|---|---|---|
| 72 | | 6-Fluoro-8-(4-methyl-piperazin-1-yl)-4-oxo-4H-chromene-2-carboxylic acid [4-(4-propionyl-piperazin-1-yl)-phenyl]-amide |
| 73 | | 6-Fluoro-8-(4-mehtyl-piperazin-1-yl)-4-oxo-4H-chromene-2-carboxylic acid {4-[4-(3-hydroxy-propanoyl)-piperazin-1-yl]-phenyl}-amide |
| 74 | | N-[8-(4-Methyl-piperazin-1-yl)-4-oxo-4H-chromen-2-yl]-4-morpholin-4-yl-benzamide |
| 75 | racemic | 8-(4-Methyl-piperazin-1-yl)-chroman-2-carboxylic acid (4-morphlin-4-yl-phenyl)-amide |

TABLE 1-continued

Compounds

| Example # | Structure | Name |
|---|---|---|
| 76 | 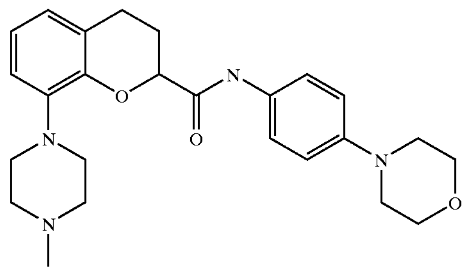 | (+)-8-(4-Methyl-piperazin-1-yl)-chroman-2-carboxylic acid (4-morpholin-4-yl-phenyl)-amide |
| 77 | 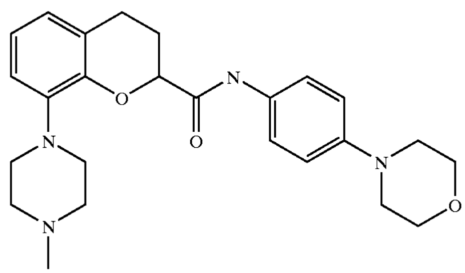 | (−)-8-(4-Methyl-piperazin-1-yl)-chroman-2-carboxylic acid (4-morpholin-4-yl-phenyl)-amide |
| 78 | 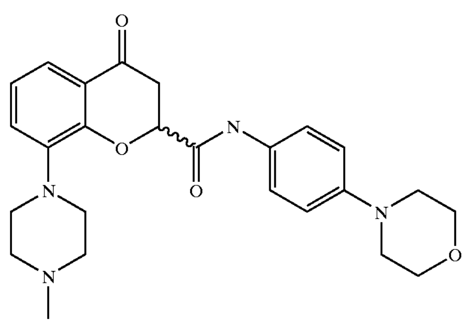 | racemic-8-(4-methyl-piperazin-1-yl)-4-oxo-chroman-2-carboxylic acid (4-morpholin-4-yl-phenyl)-amide |
| 79 | 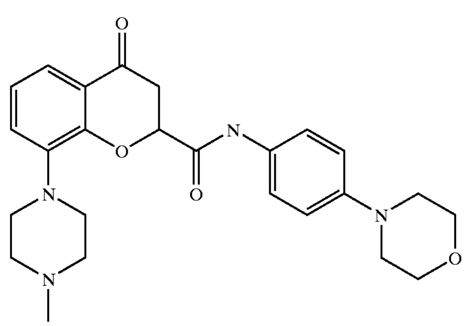 | 8-(4-Methyl-piperazin-1-yl)-4-oxo-chroman-2-carboxylic acid (4-morpholin-4-yl-phenyl)-amide (faster running isomer) |
| 80 | 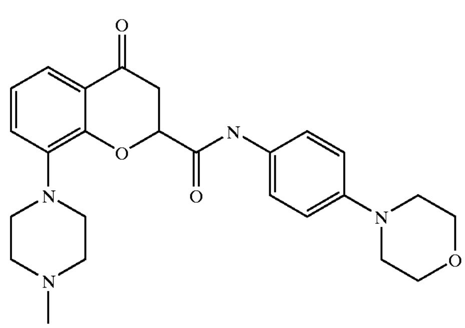 | 8-(4-Methyl-piperazin-1-yl)-4-oxo-chroman-2-carboxylic acid (4-morpholin-4-yl-phenyl)-amide (slower running isomer). |

TABLE 1-continued

Compounds

| Example # | Structure | Name |
|---|---|---|
| 81 | 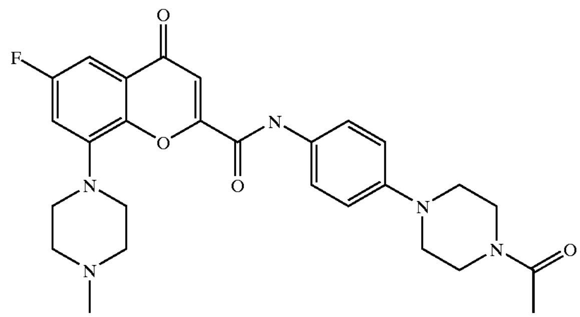 | 4-[4-({1-[6-Fluoro-8-(4-methyl-piperazin-1-yl)-4-oxo-4H-chromen-2-yl)-methanoyl}-amino)-phenyl]-piperazine-1-carboxylic acid ethylamide |
| 82 | 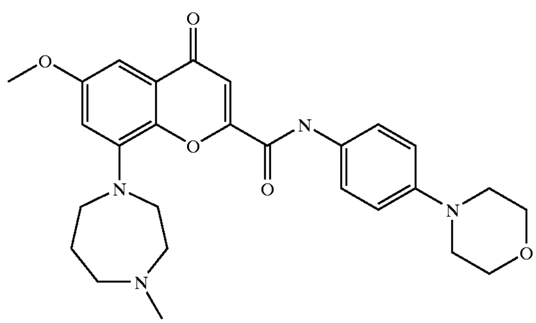 | 6-Methoxy-8-(4-methyl-[1,4]diazepan-1-yl)-4-oxo-4H-chromene-2-carboxylic acid (4-morpholin-4-yl-phenyl)-amide |
| 83 | 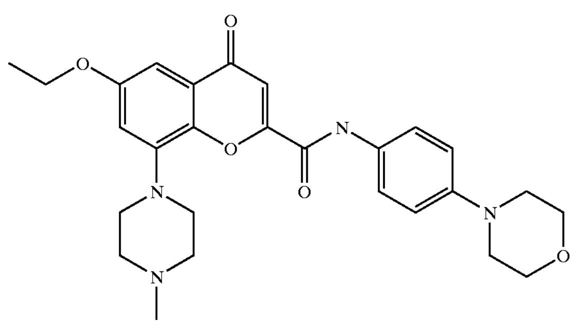 | 6-Ethoxy-8-(4-methyl-piperazin-1-yl)-4-oxo-4H-chromene-2-carboxylic acid (4-morpholin-4-yl-phenyl)-amide |
| 84 | 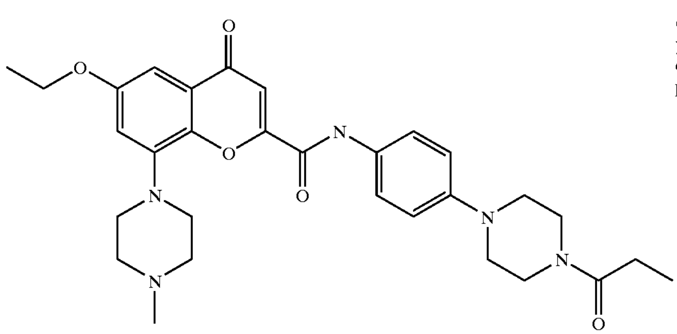 | 6-Ethoxy-8-(4-methyl-piperazin-1-yl)-4-oxo-4H-chromene-2-carboxylic acid [4-(4-propionyl-piperazin-1-yl)-phenyl]-amide |

TABLE 1-continued

Compounds

| Example # | Structure | Name |
|---|---|---|
| 85 | 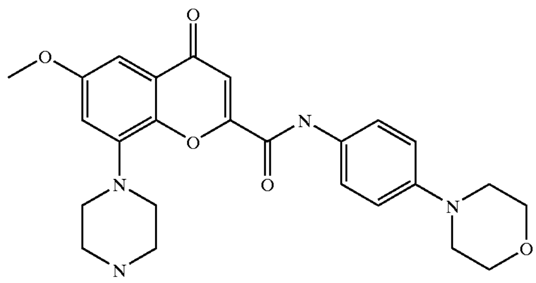 | 6-Methoxy-4-oxo-8-piperazin-1-yl-4H-chromene-2-carboxylic acid (4-morpholin-4-yl-phenyl)-amide |
| 86 | 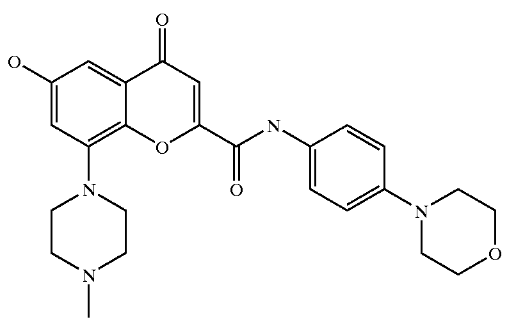 | 6-Hydroxy-8-(4-methyl-piperazin-1-yl)-4-oxo-4H-chromene-2-carboxylic acid (4-morpholin-4-yl-phenyl)-amide |
| 87 | 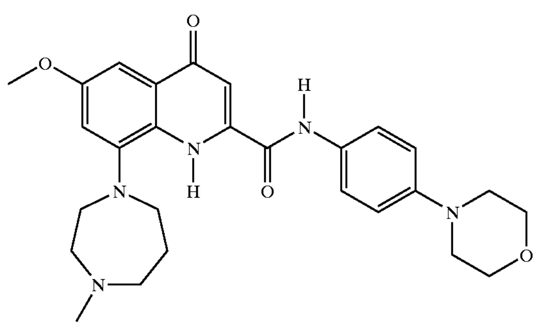 | 6-Methoxy-8-(4-methyl-[1,4]diazepan-1-yl)-4-oxo-1,4-dihydro-quinoline-2-carboxylic acid (4-morpholin-4-yl-phenyl)-amide |
| 88 | 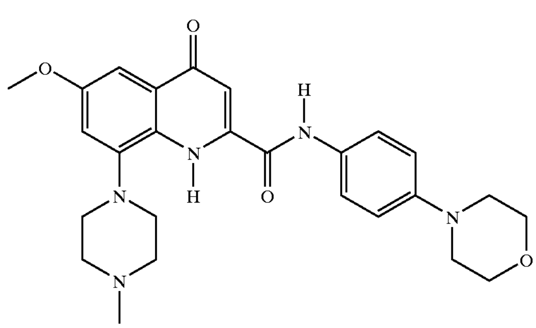 | 6-Methoxy-8-(4-methyl-piperazin-1-yl)-4-oxo-1,4-dihydro-quinoline-2-carboxylic acid (4-morpholin-4-yl-phenyl)-amide |

TABLE 1-continued

Compounds

| Example # | Structure | Name |
|---|---|---|
| 89 | | 6-Methoxy-8-(4-methyl-piperazin-1-yl)-4-oxo-1,4-dihydro-quinoline-2-carboxylic acid [4-(4-propionyl-piperazin-1-yl)-phenyl]-amide |
| 90 | | 6-Fluoro-8-(4-methyl-piperazin-1-yl)-4-oxo-1,4-dihydro-quinoline-2-carboxylic acid (4-morpholin-4-yl-phenyl)-amide |
| 91 | | 6-Fluoro-8-(4-methyl-piperazin-1-yl)-4-oxo-1,4-dihydro-quinoline-2-carboxylic acid [4-(4-propionyl-piperazin-1-yl)-phenyl]-amide |
| 92 | | 8-[(2-Dimethylamino-ethyl)-methyl-amino]-6-methoxy-4-oxo-1,4-dihydro-quinoline-2-carboxylic acid (4-morpholin-4-yl-phenyl)-amide |

TABLE 1-continued

Compounds

| Example # | Structure | Name |
|---|---|---|
| 93 | 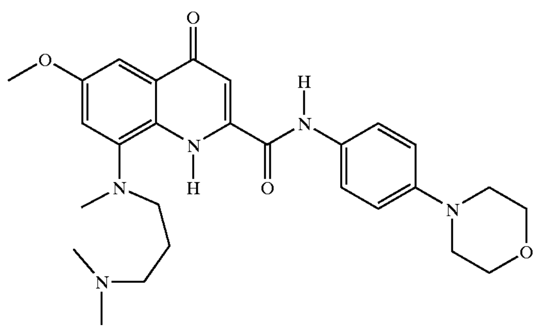 | 8-[(3-Dimethylamino-propyl)-methyl-amino]-6-methoxy-4-oxo-1,4-dihydro-quinoline-2-carboxylic acid (4-morpholin-4-yl-phenyl)-amide |
| 94 | 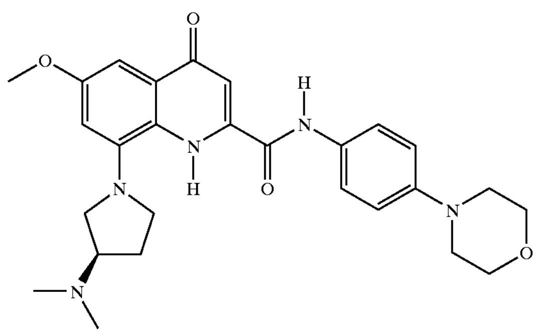 | 8-((3R)-(+)-3-Dimethylamino-pyrrolidin-1-yl)-6-methoxy-4-oxo-1,4-dihydro-quinoline-2-carboxylic acid (4-morpholin-4-yl-phenyl)-amide |
| 95 | 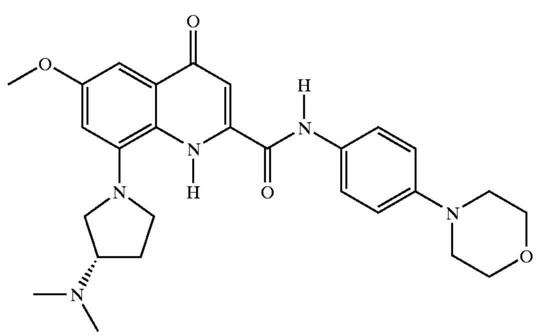 | 8-((3S)-(−)-3-Dimethylamino-pyrrolidin-1-yl)-6-methoxy-4-oxo-1,4-dihydro-quinoline-2-carboxylic acid (4-morpholin-4-yl-phenyl)-amide |
| 96 | 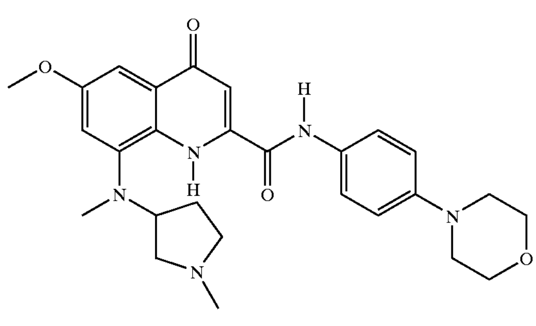 | 6-Methoxy-8-[methyl-(1-methyl-pyrrolidin-3-yl)-amino]-4-oxo-1,4-dihydro-quinoline-2-carboxylic acid (4-morpholin-4-yl-phenyl)-amide |

TABLE 1-continued

Compounds

| Example # | Structure | Name |
|---|---|---|
| 97 | 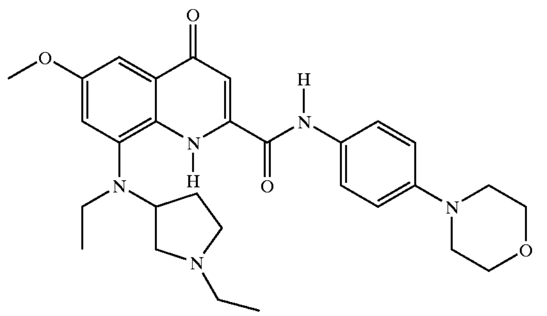 | 8-[Ethyl-(1-ethyl-pyrrolidin-3-yl) amino]-6-methoxy-4-oxo-1,4-dihydro-quinoline-2-carboxylic acid (4-morpholin-4-yl-phenyl)-amide |
| 98 | 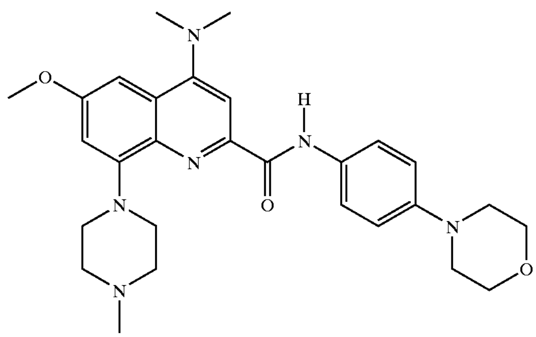 | 4-dimethylamino-6-methoxy-8-(4-methyl-piperazin-1-yl)-quinoline-2-carboxylic acid (4-morpholin-4-yl phenyl)-amide |
| 99 | 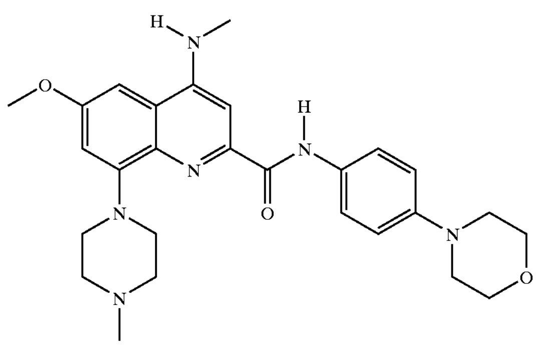 | 6-methoxy-4-methylamino-8-(4-methyl-piperazin-1-yl)-quinoline-2-carboxylic acid (4-morpholin-4-yl-phenyl)-amide |
| 100 | 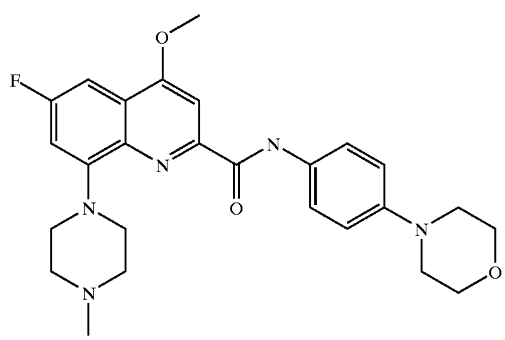 | 6-fluoro-4-methoxy-8-(4-methyl-piperazin-1-yl)-quinoline-2-carboxylic acid (4-morpholin-4-yl-phenyl)-amide |

TABLE 1-continued

Compounds

| Example # | Structure | Name |
|---|---|---|
| 101 | 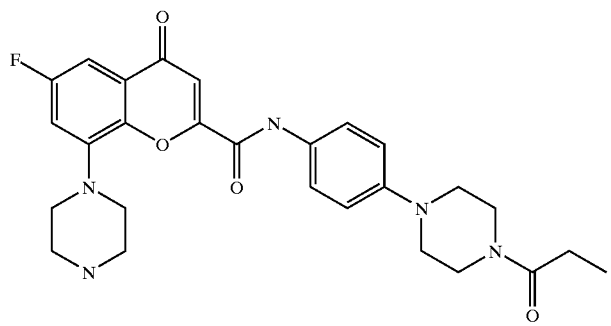 | 6-Fluoro-4-oxo-8-piperazin-1-yl-4H-chromene-2-carboxylic acid (4-morpholin-4-yl-phenyl)-amide |

Also provided herein are the pharmaceutically acceptable salts of the compounds set forth in Table 1.

The following reference examples illustrate the making of intermediates in the synthesis of the compounds of the present invention, and are not intended to limit the invention in any manner.

REFERENCE EXAMPLE 1

Preparation of Reference Example 1

8-(4-Methyl-piperazin-1-yl)-4-oxo-4H-chromene-2-carboxylic acid hydrochloride

Reference Example 1a (E,Z)-2-(2-Bromo-phenoxy)-but-2-enedioic acid diethyl ester Diethyl acetylenedicarboxylate (20 ml, 0.162 mol) was added to 2-bromophenol (28 g, 0.162 mol), in anhydrous 2-propanol (60 ml) followed by the addition of a catalytic amount of tetrabutylammonium fluoride (0.5 ml, 1.0 M in THF). The solution was stirred at room temperature four hours and was then heated to reflux for one hour. The mixture was cooled to room temperature, then concentrated under vacuum to an oil (51 g=91%).

Reference Example 1b (E,Z)-2-(2-Bromo-phenoxy)-but-2-enedioic acid (E,Z)-2-(2-Bromo-phenoxy)-but-2-enedioic acid diethyl ester (51 g, 148 mmol) as prepared in Reference Example 1a was suspended in ethanol (95 ml) and a solution of sodium hydroxide (12.9 g, 0.323 mol) in water (95 ml) was added. The solution was refluxed for 1 h to give a clear orange solution. The mixture was cooled to room temperature and acidified with 6 M HCl (50 ml). The mixture was then concentrated under vacuum and the residue azeotroped (4x) with ethanol. The solid was filtered, washed with water and dried to give (2Z)-2-(2-bromo-4-methoxyphenoxy)-2-butenedioic acid as a light orange solid (24.3 g, 88% yield). This crude product was used without further purification.

Reference Example 1c

Ethyl-8-Bromo-4-oxo-4H-chromene-2-carboxylate

Sulfuric acid (95 mL) was added to crude (E,Z)-2-(2-Bromo-phenoxy)-but-2-enedioic acid as prepared in Reference Example 1b. After heating the mixture with a heat gun for 45 a min an orange milky solution was obtained. This solution was slowly added to refluxing absolute ethanol (500 mL). After the addition, the reaction was refluxed for 30 min then allowed to cool. Crystals started to form after 20 min and the reaction was put in the refrigerator overnight. The solid was filtered, washed with cold ethanol/water 9:1 and dried to give ethyl 8-bromo-4-oxo-4H-chromene-2-carboxylate as an off-white solid (11.7 g, 24% yield, mp 124–126° C.).

Reference Example 1d

Ethyl-8-(4-Methyl-piperazin-1-yl)-4-oxo-4H-chromene-2-carboxylic acid

Ethyl 8-bromo-4-oxo-4H-chromene-2-carboxylate as prepared in Reference Example 1c (Davies, Stephen et al., J. Chem. Soc. Perkin Trans I p 2597, 1987) (3.0 g, 10.1 mmol) was azeotroped with anhydrous toluene then the white solid was dissolved in 100 mL anhydrous toluene and transferred to the reaction vessel. The mixture was subjected to vacuum/argon (x2) and the following were added in order (positive argon pressure): N-methylpiperazine (1.3 ml, 11.1 mmol), 2,2'-bis(diphenylphosphino)-1,1'-binaphthyl (0.75 g, 1.2 mmol), tris(dibenzylideneacetone)dipalladium(0) (0.48 g, 0.5 mmol) then cesium carbonate (4.6 g, 14.1 mmol). The mixture was again subjected to vacuum/argon and was heated at 80° C. overnight.

The cooled reaction mixture was filtered through diatomaceous earth and the toluene solution was applied directly to a 600 ml filter funnel (silica 230–400 mesh ASTM packed in ethyl acetate) and then washed with ethyl acetate (2 l). The product was eluted with 5–8% methanol/chloroform and the desired was collected to give 2.5 g of a slightly impure orange yellow solid (mp 120–123° C.). The impure product was chromatographed on a Waters Delta Prep 4000 using 1 PrepPak cartridge (Porasil 37–55 cm 125 Å) eluting with 3–5% methanol/chloroform. The product was collected and dried to give ethyl 8-(4-methyl-1-piperazinyl)-4-oxo-4H-chromene-2-carboxylate as a yellow solid (2.25 g, 70% yield mp 124–125° C.).

GC/MS (EI, M+) m/z 316.

Reference Example 1e 8-(4-methyl-1-piperazinyl)-4-oxo-4H-chromene-2-carboxylic acid hydrochloride Ethyl 8-(4-methyl-1-piperazinyl)-4-oxo-4H-chromene-2-carboxylate as prepared in Reference Example 1d (1.01 g, 3.19 mmol) was suspended in 6 M HCl (60 ml) and to reflux for 1.5 h (after 20 min a clear solution was obtained).

The reaction was allowed to cool. The solution was concentrated in vacuo and anhydrous toluene was added (×3) and the solution was again concentrated in vacuo to give 8-(4-methyl-1-piperazinyl)-4-oxo-4H-chromene-2-carboxylic acid hydrochloride as a yellow powder (1.02 g, quantitative yield). LC/MS (M+1) m/z 289.

REFERENCE EXAMPLE 2

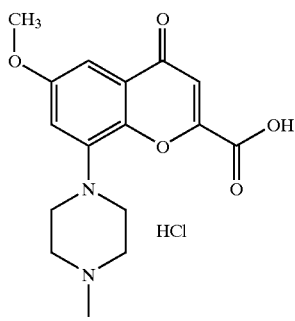

Preparation of 6-Methoxy-8-(4-Methyl-piperazin-1-yl)-4-oxo-4H-chromene-2-carboxylic acid hydrochloride Reference Example 2a Diethyl (2Z)-2-(2-bromo-4-methoxyphenoxy)-2-butenedioate Ethyl acetylenedicarboxylate (17.8 ml, 0.145 mol) was added to 2-bromo-4-methoxyphenol (Synlett p 1241, 1997) (27.3 g, 0.134 mol), in anhydrous 2-propanol (55 ml) followed by the addition of a catalytic amount of tetrabutylammonium fluoride (0.4 ml, 1.0 M in THF). The solution was stirred at room temperature overnight and was then heated to reflux for 30 min. Upon cooling a precipitate formed. The solution was cooled and filtered to give diethyl (2Z)-2-(2-bromo-4-methoxyphenoxy)-2-butenedioate as a yellow solid (29.9 g, 62% yield). Note: the solid contains 10% of diethyl (2E)-2-(2-bromo-4-methoxyphenoxy)-2-butenedioate. GC/MS (EI, M+) m/z 344 and 346.

Reference Example 2b (2Z)-2-(2-bromo-4-methoxyphenoxy)-2-butenedioic acid

Diethyl, (2Z)-2-(2-bromo-4-methoxyphenoxy)-2-butenedioate (29.9 g, 86.6 mmol) as prepared in Reference Example 2a was suspended in ethanol (55 ml) and a solution of sodium hydroxide (7.0 g, 0.175 mol) in water (55 ml) was added. The solution was refluxed for 1 h to give a clear orange solution. Most of the ethanol was removed in vacuo then 6 M HCl (50 ml) was added. The solid was filtered, washed with water and dried to give (2Z)-2-(2-bromo-4-methoxyphenoxy)-2-butenedioic acid as a light orange solid (24.3 g, 88% yield).

Reference Example 2c

Ethyl-6-methoxy-8-bromo-4-oxo-4H-chromene-2-carboxylate

Sulfuric acid (50 ml) was added to (2Z)-2-(2-bromo-4-methoxyphenoxy)-2-butenedioic acid (24.3 g, 86.6 mmol; as prepared in Reference Example 2b above). After heating the mixture with a heat gun for 5–10 min a clear deep brown solution was obtained. This solution was slowly added to refluxing absolute ethanol (250 ml). After the addition the reaction was refluxed for 30 min then allowed to cool. Crystals started to form after 20 min and the reaction was put in the refrigerator overnight. The solid was filtered, washed with cold ethanol/water 9:1 and dried to give ethyl 8-bromo-6-methoxy-4-oxo-4H-chromene-2-carboxylate as an off-white solid (12.3 g, 50% yield, mp 159–161° C.).

Reference Example 2d

Ethyl-6-methoxy-8-(4-Methyl-piperazin-1-yl)-4-oxo-4H-chromene-2-carboxylate

Ethyl 8-bromo-4-oxo-4H-chromene-2-carboxylate (9.2 g, 28.1 mmol), as prepared in Example 2c above, was azeotroped with anhydrous toluene then the white solid was dissolved in 300 ml anhydrous toluene in a 500 mL single-neck round bottom flask. The mixture was degassed by alternating argon sparge and vacuum (3×), and the following were added in order: N-methylpiperazine (4.0 ml, 35.1 mmol), 2,2'-bis(diphenylphosphino)-1,1'-binaphthyl (1.05 g, 1.69 mmol), tris(dibenzylideneacetone)dipalladium(0) (0.50 g, 0.56 mmol) then cesium carbonate (12.8 g, 39.3 mmol). The mixture was again degassed via alternating argon sparge and vacuum and was heated at 80° C. for 17 h. Additional tris(dibenzylideneacetone)dipalladium(0) (0.10 g, 0.11 mmol) and 2,2'-bis(diphenylphosphino)-1,1'-binaphthyl (0.20 g, 0.32 mmol) was added and the reaction was stirred at 80° C. for another 55 h at which time the conversion was essentially complete.

The cooled reaction mixture was diluted with tetrahydrofuran (250 mL), filtered and concentrated under vacuum. The residue was purified by chromatography on a silica column eluted with 2–5% methanol/chloroform and the desired fractions were collected and concentrated under vacuum and the residue triturated with methylene chloride to give 7.4 g (76%) of a yellow powder.

Reference Example 2e

6-Methoxy-8-(4-Methyl-piperazin-1-yl)-4-oxo-4H-chromene-2-carboxylic acid

Ethyl-6-methoxy-8-(4-Methyl-piperazin-1-yl)-4-oxo-4H-chromene-2-carboxylate (1.0 g, 2.89 mmol), as prepared in Reference Example 2d above, was suspended in 6 M HCl (60 ml) and methanol (10 mL) and warmed to reflux for 3.0 h. The reaction was allowed to cool. The solution was concentrated in vacuo and anhydrous toluene was added (×3) and the solution was again concentrated in vacuo. The residue was dried under vacuum (17 h) to yield 6-methoxy-8-(4-methyl-1-piperazinyl)-4-oxo-4H-chromene-2-carboxylic acid hydrochloride as a yellow powder (1.0 g, quantitative yield).

REFERENCE EXAMPLE 3

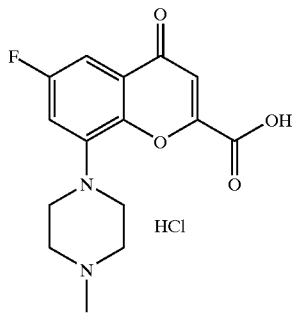

6-Fluoro-8-(4-methyl-piperazin-1-yl)-4-oxo-4H-chromene-2-carboxylic acid hydrochloride

Reference Example 3a

Diethyl (EZ)-2-(2-bromo-4-fluorophenoxy)-2-butenedioate

This compound was synthesized from 2-bromo-4-fluorophenol and diethylacetylenedicarboxylate, using the same synthetic procedures and the same stoichiometry as demonstrated in Reference Example 1a above.

Reference Example 3b (EZ)-2-(2-Bromofluorophenoxy)-2-butenedioic acid

This compound was synthesized from diethyl (EZ)-2-(2-bromo-4-fluorophenoxy)-2-butenedioate, as prepared in Reference Example 3a above, using the same synthetic procedures and the same stoichiometry as demonstrated in Reference Example 1b above.

Reference Example 3c

Ethyl-6-fluoro-8-bromo-4-oxo-4H-chromene-2-carboxylate

This compound was synthesized from (EZ)-2-(2-bromo-4-fluorophenoxy)-2-butenedioic acid, as prepared in Reference Example 3b above, using the same synthetic procedures and the same stoichiometry as demonstrated in Reference Example 1c above.

Reference Example 3d

Ethyl-6-fluoro-8-(4-Methyl-piperazin-1-yl)-4-oxo-4H-chromene-2-carboxylate

This compound was synthesized from ethyl-6-fluoro-8-bromo-4-oxo-4H-chromene-2-carboxylate, as prepared in Reference Example 3c above, using the same synthetic procedures and the same stoichiometry as demonstrated in Reference Example 1d above.

Reference Example 3e

6-Fluoro-8-(4-methyl-piperazin-1-yl)-4-oxo-4H-chromene-2-carboxylic acid hydrochloride This compound was synthesized starting from ethyl-6-methoxy-8-(4-Methyl-piperazin-1-yl)-4-oxo-4H-chromene-2-carboxylate, as prepared in Example 3d, using the same synthetic procedures and the same stoichiometry as demonstrated in Reference Example 1e above.

REFERENCE EXAMPLE 4

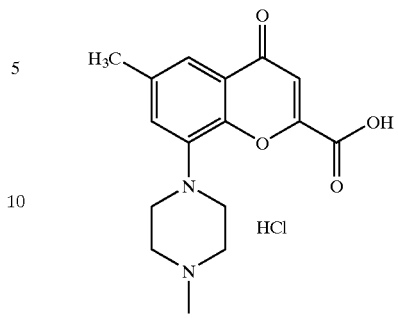

Preparation 6-Methyl-8-(4-methyl-piperazin-1-yl)-4-oxo-4H-chromene-2-carboxylic acid hydrochloride

Reference Example 4a

Diethyl (E,Z)-2-(2-bromo-4-methylphenoxy)-2-butenedioate

2-Bromo-4-methyl phenol (10 mL, 83 mmol) was dissolved in diethyl ether (90 mL). To this was added dropwise triethyl amine (13.7 mL, 98 mmol) followed by dimethyl acetylene dicarboxylate (11.2 mL, 91 mmol). The resulting mixture was stirred overnight at room temperature. The reaction was worked up by adding diethyl ether (200 mL) and tetrahydrofuran (50 mL) and washing the resulting mixture with 1N HCl (200 mL), water (200 mL) and brine (100 mL). The organic phase was then dried (Na$_2$SO$_4$), filtered and concentrated to a red-brown oil which was used without further purification.

Reference Example 4b (2E,Z)-2-(2-Bromo-4-fluorophenoxy)-2-butenedioic acid

This compound was synthesized from diethyl (E,Z)-2-(2-bromo-4-methylphenoxy)-2-butenedioate, as prepared in Reference Example 4a above, using the same synthetic procedures and the same stoichiometry as demonstrated in Example 1b above.

Reference Example 4c

Ethyl-6-methyl-8-bromo-4-oxo-4H-chromene-2-carboxylate

This compound was synthesized from (2Z)-2-(2-bromo-4-methylphenoxy)-2-butenedioic acid, as prepared in Reference Example 4b above, and using the same synthetic procedures and the same stoichiometry as demonstrated in Reference Example 1c above.

Reference Example 4d

Ethyl-6-methyl-8-(4-Methyl-piperazin-1-yl)-4-oxo-4H-chromene-2-carboxylate

This compound was synthesized from ethyl-&methyl-8-bromo-4-oxo-4H-chromene-2-carboxylate, as prepared in Reference Example 4c above, using the same synthetic procedures and the same stoichiometry as demonstrated in Reference Example 1d above.

Reference Example 4e

6-Methyl-8-(4-methyl-piperazin-1-yl)-4-oxo-4H-chromene-2-carboxylic acid hydrochloride This compound was synthesized starting with ethyl6-methyl-8-(4-Methyl-piperazin-1-yl)-4-oxo-4H-chromene-2- carboxylate, as prepared in Reference Example 4d, using the same synthetic procedures and the same stoichiometry as demonstrated in Reference Example 1e above.

REFERENCE EXAMPLE 5

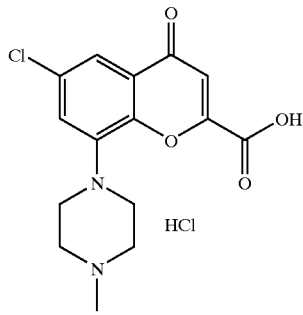

Preparation of 6-Chloro-8-(4-methyl-piperazin-1-yl)-4-oxo-4H-chromene-2-carboxylic acid hydrochloride Reference Example 5a Diethyl (E,Z)-2-(2-bromo-4-chlorophenoxy)-2-butenedioate This compound was prepared from 2-bromo-4-chloro phenol and dimethyl acetylenedicarboxylate by the same synthetic procedures and in the same stoichiometry as the preparation described in Reference Example 4a.

Reference Example 5b (2E,Z)-2-(2-Bromo-4-chlorophenoxy)-2-butenedioic acid

This compound was synthesized from diethyl (E,Z)-2-(2-bromo-4-chlorophenoxy)-2-butenedioate, as prepared in Reference Example 5a above, as using the same synthetic procedures and the same stoichiometry as demonstrated in Reference Example 1b above.

Reference Example 5c

Ethyl-6-chloro-8-bromo-4-oxo-4H-chromene-2-carboxylate

This compound was synthesized from (2E,Z)-2-(2-bromo-4-chlorophenoxy)-2-butenedioic acid, as prepared in Reference Example 5b above, using the same synthetic procedures and the same stoichiometry as demonstrated in Example 1c above.

Reference Example 5d

Ethyl-6-chloro-8-(4-Methyl-piperazin-1-yl)-4-oxo-4H-chromene-2-carboxylate

This compound was synthesized from ethyl-6-chloro-8-bromo-4-oxo-4H-chromene-2-carboxylate, as prepared in Reference Example 5c above, using the same synthetic procedures and the same stoichiometry as demonstrated in Example 1d above.

Reference Example 5e

6-Chloro-8-(4-methyl-piperazin-1-yl)-4-oxo-4H-chromene-2-carboxylic acid hydrochloride This compound was synthesized starting with ethyl-6-chloro-8-(4-methyl-piperazin-1-yl)-4-oxo-4H-chromene-2-carboxylate, prepared in Reference Example 5d above, using the same synthetic procedures and the same stoichiometry as demonstrated in Reference Example 1e above.

REFERENCE EXAMPLE 6

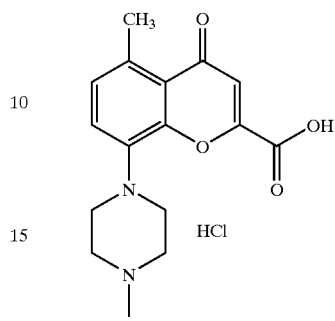

Preparation of 5-Methyl-8-(4-methyl-piperazin-1-yl)-4-oxo-4H-chromene-2-carboxylic acid hydrochloride Reference Example 6a Diethyl (E,Z)-2-(2-chloro-5-methylphenoxy)-2-butenedioate This compound was prepared from 2-chloro-5-methylphenol and dimethyl acetylenedicarboxylate by the same synthetic procedures and in the same stoichiometry as the preparation described in Reference Example 1a.

Reference Example 6b (2EZ)-2-(2-chloro-5-methylphenoxy)-2-butenedioic acid

This compound was synthesized from diethyl (E,Z)-2-(2-chloro-5-methylphenoxy)-2-butenedioate, as prepared in Reference Example 6a above, using the same synthetic procedures and the same stoichiometry as demonstrated in Reference Example 1b above.

Reference Example 6c

Ethyl-5-methyl-87 chloro-4-oxo-4H-chromene-2-carboxylate

This compound was synthesized from (2Z)-2-(2-chloro-5-methylphenoxy)-2-butenedioic acid, as prepared in Reference example 6b, using the same synthetic procedures and the same stoichiometry as demonstrated in Reference Example 1c above.

Reference Example 6d

Ethyl-5-methyl-8-(4-Methyl-piperazin-1-y)-4-oxo-4H-chromene-2-carboxylate

Ethyl 5-methyl-8-chloro-4-oxo-4H-chromene-2-carboxylate (1.0 g, 3.6 mmol) as prepared in Reference Example 6c above, was azeotroped with anhydrous toluene then the white solid was dissolved in 100 ml anhydrous toluene in a 250 mL single-neck round bottom flask. The mixture was degassed by alternating argon sparge and vacuum (3x), and the following were added in order: N-methylpiperazine (0.6 ml, 5.37 mmol), (2'-dicyclohexylphosphanyl-biphenyl-2-yl)dimethyl-amine (JACS 1998, 120, p 9722) (40 mg, 0.1 mmol), tris(dibenzylideneacetone)dipalladium(0) (66 mg, 0.072 mmol) then cesium carbonate (1.6 g, 5.37 mmol). The mixture was again degassed via alternating argon sparge and vacuum and was heated at 80° C. for 17 h. Additional tris(dibenzylideneacetone)dipalladium(0) (66 mg, 0.072 mmol) and (2'-dicyclopentylphosphanyl-biphenyl-2-yl)-dimethyl-amine (40 g, 0.1 mmol) were added and the reaction was stirred at 80° C. for another four days at which time the conversion was still only about 50% complete by HPLC. Tetrahydrofuran (100 mL) was added, and the combined mixture was filtered, concentrated under vacuum and purified by chromatography on silica eluted with 2.5% methanol in chloroform. The desired fractions were concentrated under vacuum to yield a yellow powder (250 mg=21%).

Reference Example 6e

5-Methyl-8-(4-methyl-piperazin-1-yl)-4-oxo-4H-chromene-2-carboxylic acid hydrochloride This compound was synthesized starting with ethyl-5-methyl-8-(4-methyl-piperazin-1-yl)-4-oxo-4H-chromene-2-carboxylate, as prepared in Reference Example 6d, and using the same synthetic procedures and the same stoichiometry as demonstrated in Example 1e above.

REFERENCE EXAMPLE 7

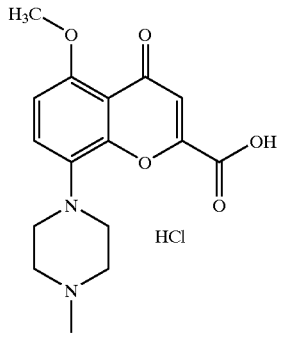

Preparation of 5-Methoxy-8-(4-methyl-piperazin-1-yl)-4-oxo-4H-chromene-2-carboxylic acid hydrochloride Reference Example 7a (EZ)-2-(2-Bromo-5-methoxyphenoxy)-2-butenedioate This compound was prepared from 2-bromo-5-methoxyphenol and dimethyl acetylenedicarboxylate by the same synthetic procedures and in the same stoichiometry as the preparation described in Reference Example 1a.

Reference Example 7b (EZ)-2-(2-Bromo-5-methoxyphenoxy)-2-butenedioic acid

This compound was synthesized from diethyl (E,Z)-2-(2-bromo-5-methoxyphenoxy)-2-butenedioate, as prepared in Reference Example 7a, using the same synthetic procedures and the same stoichiometry as demonstrated in Reference Example 1b above.

Reference Example 7c

Ethyl-5-methoxy-8-bromo-4-oxo-4H-chromene-2-carboxylate

This compound was synthesized from (E,Z)-2-(2-bromo-5-methoxyphenoxy)-2-butenedioic acid, as prepared in Reference Example 7b above, using the same synthetic procedures and the same stoichiometry as demonstrated in Reference Example 1c above.

Reference Example 7d

Ethyl-5-methoxy-8-(4-Methyl-piperazin-1-yl)-4-oxo-4H-chromene-2-carboxylate

This compound was synthesized from ethyl-5-methoxy-8-bromo-4-oxo-4H-chromene-2-carboxylate, as prepared in Reference Example 7c above, using the same synthetic procedures and the same stoichiometry as demonstrated in Reference Example 1d above.

Reference Example 7e

5-Methoxy-8-(4-methyl-piperazin-1-yl)-4-oxo-4H-chromene-2-carboxylic acid hydrochloride This compound was prepared from ethyl-5-methoxy-8-(4-Methyl-piperazin-1-yl)-4-oxo-4H-chromene-2-carboxylate, as prepared in Reference Example 7d above, using the same method as the preparation in 1e.

REFERENCE EXAMPLE 8

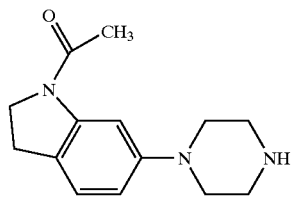

Preparation of 1-(6-Piperazin-1-yl-2,3-dihydro-indol-1-yl)-ethanone

Reference Example 8a

1-[5-(4-Benzyl-piperazin-1-yl)-2,3-dihydro-indol-1-yl]-ethanone 1-acetyl-5-bromoindoline (3.0 g, 12.5 mmol) was dissolved in toluene (60 mL). To this was added, sodium t-butoxide (1.68 g, 17.5 mmol), N-benzylpiperazine (2.4 mL, 13.8 mmol), S-BINAP (0.93 g, 1.5 mmol) and Pd$_2$(dba)$_3$ (0.46 g, 0.5 mmol). The mixture was degassed via three cycles of vacuum and nitrogen sparge and then stirred at 95° C. until GC analysis confirmed that the reaction was complete (1 h). The mixture was diluted with ethyl acetate (150 mL), washed with water and extracted with 2N HCl (2×100 mL). The combined aqueous extract was basified with concentrated ammonium hydroxide and extracted with ethyl acetate (2×100 mL). The combined organic extract was dried (MgSO$_4$) and concentrated to yield a solid (2.7 g) which was purified by chromatography to yield a white solid (1.81 g, 43%). Mp=150.5–152.8° C.

Reference Example 8b 1-(6-Piperazin-1-yl-2,3-dihydro-indol-1-yl)-ethanone

1-[5-(4-Benzyl-piperazin-1-yl)-2,3-dihydro-indol-1-yl]ethanone (0.37 g, 1.1 mmol), as prepared in Reference Example 8a above, was dissolved in methanol (5 mL). Pd/C (90 mg, 10%) and ammonium formate (0.9 g, 14 mmol) was added and the resulting mixture was heated to 65° C. for two hours. The mixture was filtered and the filter cake washed with hot methanol. The combined filtrate was concentrated to yield the desired product (0.26 g, 90%).

REFERENCE EXAMPLE 9

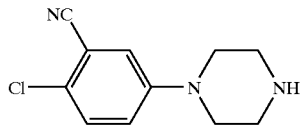

Preparation of 2-chloro-5-piperazin-1-yl benzonitrile

Reference Example 9a

3-Cyano-4-chloroaniline

2-Chloro-5-nitrobenzonitrile (25 g, 137 mmol) was dissolved in ethanol (275 mL). Stannous chloride dihydrate (154.5 g, 0.685 M) was added and the mixture stirred at 70° C. for 30 min. The mixture was then cooled to room temperature and poured into crushed ice. The mixture was made basic with solid sodium hydroxide. This mixture was extracted with ethyl acetate (3×100 mL). The extracts were combined, washed with brine, dried (MgSO₄), concentrated and the residue dried under vacuum and recrystallized from ethanol to yield light brown needles (10.6 g, 51%).

Reference Example 9b 2-chloro-5-piperazin-1-yl benzonitrile

3-Cyano-4-chloroaniline (10.1 g, 66 mmol), as prepared in Reference Example 9a, was dissolved in n-butanol (300 mL) bis-(2-chloroethyl)amine hydrochloride (23.2 g, 130 mmol) and potassium iodide (50 mg, catalytic) were added. The mixture was heated at reflux for three days, then cooled in a refrigerator overnight. A solid precipitate was collected by filtration, washed with cold n-butanol and dried. The crude product was distributed between methylene chloride and 2N ammonium hydroxide. The organic layer was separated, dried (Na₂SO₄) and concentrated to yield a light yellow solid (9.1 g, 59%) which gave a single peak by GC and TLC analysis.

REFERENCE EXAMPLE 10

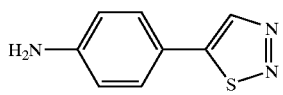

Preparation of 4-[1,2,3]-thiadiazol-5-yl-phenylamine

SnCl₂.H₂O (3.21 g, 5 eq) was added to a slurry of (5-(4-Nitrophenyl)-1,2,3-thiadiazole (Lancaster Synthesis) (0.59 g, 2.8 mmol) in absolute EtOH (50 mL) and the reaction heated to 70° C. for 2 h. The reaction was allowed to cool to room temperature and pour into saturated NaHCO₃ and ice. The product was extracted with EtOAc (2×) the solution dried (MgSO₄) and evaporated to dryness in vacuo to yield 0.47 g of a light yellow solid mp 126–128° C.

REFERENCE EXAMPLE 11

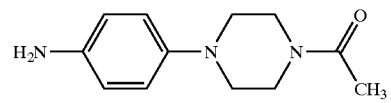

Preparation of 1-[4-(4-Amino-phenyl)-piperazin-1-yl]-ethanone

Reference Example 11a 4-(4-Nitrophenyl)-1-acetylpiperazine 1-(4-Nitrophenyl)piperazine (2.5 g, 12.1 mmol) was dissolved in dichloromethane (100 ml). Triethylamine (2.0 ml, 14.5 mmol) was added and the reaction was cooled to 0° C. Atetic anhydride (1.25 ml, 13.3 mmol) was added dropwise and the reaction was stirred at 0° C. for 1 h. Saturated sodium bicarbonate was added and the reaction was extracted (×3) with dichloromethane, dried (MgSO₄), filtered and concentrated in vacuo to give 4-(4-nitrophenyl)-1-acetylpiperazine as a yellow solid (3.01 g). GC/MS (EI, M+) m/z=249.

Reference Example 11b

1-[4-(4-Amino-phenyl)-piperazin-1-yl]-ethanone 4-(4-Nitrophenyl)-1-acetylpiperazine (3.0 g, 12.0 mmol), as prepared in Reference Example 11a above, was mixed in methanol (100 ml) and 2 M ammonia in methanol (50 ml) and 10% palladium on carbon (300 mg) was added. The mixture was hydrogenated on a Paar apparatus (50 psi) for 1.5 h.

The reaction was allowed to cool, the catalyst was filtered and the solution was concentrated in vacuo. The crude solid was recrystallized from ethyl acetate to give 4-(4-acetyl-1-piperazinyl)benzenamine as a light purple solid (1.86 g, 70% yield, mp 149.5–150.5° C.). GC/MS (EI, M+) m/z=219.

REFERENCE EXAMPLE 12

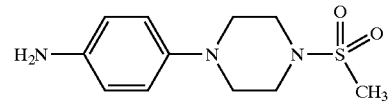

Preparation of 4-(4-methanesulfonyl-piperazin-1-yl)-phenylamine

Reference Example 12a 4-(4-Nitrophenyl)-1-methylsulfonylpiperazine 1-(4-Nitrophenyl)piperazine (2.79 g, 13.5 mmol) was dissolved in dichloromethane (100 ml). Triethylamine (2.25 ml, 16.2 mmol) was added and the reaction was cooled to 0° C. Methanesulfonyl chloride (1.15 ml, 14.9 mmol) was added dropwise and the reaction was stirred at 0° C. for 1 h. Saturated sodium bicarbonate was added and the reaction was extracted (×3) with dichloromethane, dried (MgSO₄), filtered and concentrated in vacuo to give 4-(4 nitrophenyl)-1-methylsulfonylpiperazine as a yellow solid (3.83 g, quantitative yield). GC/MS (EI, M+) m/z=285.

Reference Example 12b 4-(4-methanesulfonyl-piperazin-1-yl)-phenylamine 4-(4-Nitrophenyl)-1-methylsulfonylpiperazine (3.83 g, 13.4 mmol), as prepared in Reference Example 12a above, was mixed in methanol (100 ml) and 2 M ammonia in methanol (50 ml) and 10% palladium on carbon (400 mg) was added. The mixture was hydrogenated on a Paar apparatus (50 psi) for 3 h.

The reaction was allowed to cool, the catalyst was filtered, washed with methanol then washed with chloroform. The chloroform portion contained a minor amount of the desired but looked purer. The chloroform portion was concentrated in vacuo and was recrystallized ethyl acetate to give 4-[4-(methylsulfonyl)-1-piperazinyl]benzenamine as a shiny brown solid (0.94 g, 27% yield, mp 192–193° C.). GC/MS (EI, M+) m/z=255.

REFERENCE EXAMPLE 13

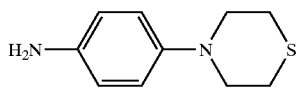

Preparation of 4-Thiomorpholin-4-yl-phenylamine

Reference Example 13a 4-(4-Nitro-phenyl)thiomorpholine

4-Fluoronitrobenzene (3.0 g, 21.3 mmol) was dissolved in toluene (25 mL). Thiomorpholine (2.4 mL, 23.4 mmol) was added and the mixture stirred overnight at 100° C. At 17 h, the mixture was distributed between ethyl acetate (100 mL) and saturated sodium bicarbonate (50 mL). The organic layer was separated, dried ($Na_2SO_4$), filtered and concentrated under vacuum. The residue was triturated with hexane to yield a bright yellow solid.

Reference Example 13b

4-Thiomorpholin-4-yl-phenylamine 4-(4-Nitro-phenyl)-thiomorpholine (3.0 g, 13.4 mmol), as prepared in Reference Example 13a above, was dissolved in ethanol (250 mL) and 10% palladium on carbon (250 mg) was added. This mixture was shaken on a Parr hydrogenator for 3 h. The reaction mixture was then filtered through diatomaceous earth and concentrated under vacuum. The residue was triturated with hexane to yield an gray solid (2.1 g).

REFERENCE EXAMPLE 14

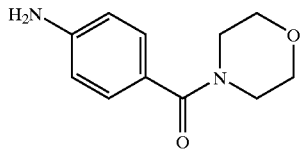

Preparation of 1-(4-Amino-phenyl)-1-morpholinyl-methanone

Reference Example 14a

1-Morpholin-4-yl-1-(4-nitro-phenyl)-methanone

4-Nitrobenzoyl chloride (5 g, 27 mmol) in tetrahydrofuran (10 mL) was added slowly to a solution of morpholine (5 g, 88 mmol) and triethylamine (2.7 g, 27 mmol) in tetrahydrofuran (50 mL), and stirred at room temperature for four hours. Ethyl acetate (200 mL) was added to the mixture and the combined mixture was washed with water (25 mL), 1N HCl (25 mL), water (25 mL), saturated sodium bicarbonate (25 mL), water (25 mL) and brine (25 mL). The mixture was dried (Na2SO4), filtered and concentrated under vacuum and the residue used without further purification.

Reference Example 14b 1-(4-Amino-phenyl)-1-morpholin-4-yl-methanone

This compound was prepared from 1-morpholin-4-yl-1-(4-nitro-phenyl)-methanone as prepared in Reference Example 13b.

REFERENCE EXAMPLE 15

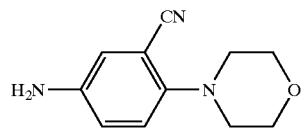

Preparation of 5-Amino-2-morpholin-4-yl-benzonitrile

Reference Example 15a

2-Morpholin-4-yl-5-nitro-benzonitrile

3-Cyano-4-fluoronitrobenzene (3.3 g, 19.9 mmol) was dissolved in ethyl acetate (10 mL). Morpholine (2.2 mL, 25 mmol), and N,N-diisopropylethylamine (3.5 mL, 20 mmol) were added and the mixture stirred overnight at room temperature. At 17 h, additional ethyl acetate (150 mL) was added and the combined mixture was washed with water (50 mL) and brine (50 mL), dried ($Na_2SO_4$), filtered and concentrated under vacuum. The residue was used without further purification.

Reference Example 15b

5-Amino-2-morpholin-4-yl-benzonitrile

This compound was prepared from 2-Morpholin-4-yl-5-nitro-benzonitrile (as prepared in Reference Example 15a above), as prepared in Reference Example 13b.

REFERENCE EXAMPLE 16

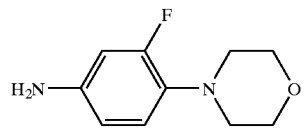

Preparation of 3-Fluoro-4-morpholin-4-yl-phenylamine

Reference Example 16a 4-(2-Fluoro-4-nitro-phenyl)-morpholine 3,4-Difluoronitrobenzene (3.7 g, 23.2 mmol) was dissolved in ethyl acetate (10 mL). Morpholine (2.2 mL, 25 mmol), and N,N-diisopropylethylamine (4 mL, 23 mmol) were added and the mixture stirred overnight at room temperature. At 17 h, additional ethyl acetate (150 mL) was added and the combined mixture was washed with water (50 mL) and brine (50 mL), dried (Na₂SO₄), filtered and concentrated under vacuum. The residue was used without further purification.

Reference Example 16b

3-Fluoro-4-morpholin-4-yl-phenylamine

This compound was prepared from 4-(2-Fluoro-4-nitro-phenyl)-morpholine, (as prepared in Reference Example 16a above) as prepared in Reference Example 13b.

REFERENCE EXAMPLE 17

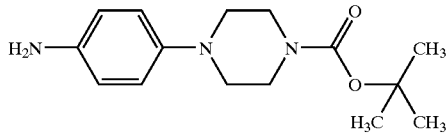

Preparation of 4-(4-Amino-phenyl)-piperazine-1-carboxylic acid tert-butyl ester

Reference Example 17a 4-(4-Nitro-phenyl)-piperazine-1-carboxylic acid tert-butyl ester 4-Fluoronitrobenzene (4.8 g, 34 mmol) was dissolved in ethyl acetate (25 mL). Piperazine-1-carboxylic acid tert-butyl ester (6.7 g, 36 mmol) and N,N-diisopropylethylamine (6.3 mL, 36 mmol) were added and the mixture was stirred at 65° C. for five days and cooled to room temperature. Ether (100 mL) was added and the combined mixture was washed with water (25 mL) and brine (25 mL), dried (Na2SO4), filtered and concentrated under vacuum. The residue was triturated with hexane to yield a bright yellow solid (8 g, 77%).

Reference Example 17b 4-(4-Aminophenyl)-piperazine-1-carboxylic acid tert-butyl ester 4-(4Amino-phenyl)-piperazine-1-carboxylic acid tert-butyl ester was prepared from 4-(4-Nitro-phenyl)piperazine-1-carboxylic acid tert-butyl ester, (as prepared in Reference Example 17a) as prepared in Reference Example 13b.

REFERENCE EXAMPLE 18

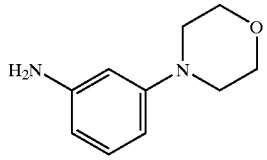

Preparation of 3-Morpholin-4-yl-phenylamine

Reference Example 18a 4-(3-Nitro-phenyl)-morpholine

3-Fluoronitrobenzene (10 g, 71 mmol) was dissolved in acetonitrile (100 mL). Morpholine (30 mL, 350 mmol) was added and the mixture was reacted 18 h at 150° C./80 psi in a pressure reactor. The reaction was cooled to room temperature, concentrated under vacuum and 5 g of the total mixture was purified by column chromatography on silica eluted with CH₂Cl₂. The product (3.6 g) was isolated as a bright yellow oil.

Reference Example 18b

3-Morpholin-4-yl-phenylamine

3-Morpholin-4-yl-phenylamine was prepared from 4-(3-Nitro-phenyl)-morpholine, (as in prepared in Reference Example 18a), as prepared in Reference Example 13b.

REFERENCE EXAMPLE 19

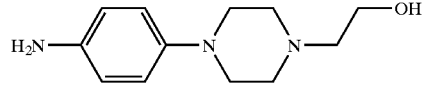

Preparation of 2-[1-(4-amino-phenyl)-piperazin-1-yl]-ethanol

Reference Example 19a

2-[4-(4-nitrophenyl)piperazine-1-yl]-ethanol

2-[4-(4-nitrophenyl)piperazine-1-yl]-ethanol is prepared from commercially available 4-fluoronitrobenzene (Aldrich) and commercially available N-(2-hydroxyethyl)piperazine (Aldrich) via the same procedure as described in Reference Example 13a above.

Reference Example 19b

2-[4-(4-amino-phenyl)-piperazin-1-yl]-ethanol

2-[4-(4-amino-phenyl)-piperazin-1-yl]-ethanol is prepared by catalytic hydrogenation of 2-[4-(4-nitrophenyl)piperazine-1-yl]-ethanol (prepared as in Reference Example 19a) as described in Reference Example 13b.

REFERENCE EXAMPLE 20

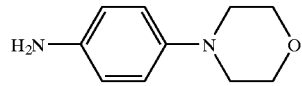

Preparation of 4-Morpholin-4-yl-phenylamine 4-(4-Nitrophenyl)morpholine (10.3 g, 49.5 mmol) (Lancaster Synthesis) was suspended in methanol (130 ml) and 2 M ammonia in methanol (70 mL) and 5% palladium on carbon (100 mg) was added. The mixture was hydrogenated on a Paar apparatus (50 psi) for 1 h. The reaction was allowed to cool, the catalyst was filtered and the solution was concentrated in vacuo. The crude solid was recrystallized from ethyl acetate/hexane to give 4-(4-morpholinyl) aniline as a light purple solid (6.2 g, 70%-yield, mp 132–133° C.).

GC/MS (EI, M+) m/z=178.

REFERENCE EXAMPLE 21

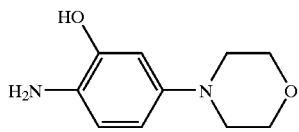

Preparation of 4-Amino-3-hydroxyphenylmorpholine

4-Nitro-3-hydroxyphenylmorpholine (Maybridge Chemical) (3.34 g, 14.9 mmol) was dissolved in 59 ml of ethanol at 30° C. The mixture was stirred at 25° C. and treated with tin(II) chloride dihydrate (16.8 grams, 74.5 mmol) with stirring. The yellow suspension was heated to reflux over a 30 minute period. TLC showed reaction progress over several hours. The mixture was refluxed for 18 hours, cooled to room temperature, and concentrated to remove most of the ethanol to give a yellow slurry. The mixture was treated with saturated aqueous sodium bicarbonate until it was basic. The mixture was extracted with ethyl acetate, filtered, and the organic layer was separated. The aqueous layer was extracted twice more with ethyl acetate. The extracts were combined, dried over magnesium sulfate, filtered, and concentrated to give 1.02 grams of a purple solid. Proton NMR and CI mass spectral analyses were consistent for the desired product (m/z=195 base peak by positive ion CI and m/z=193 base peak by negative ion CI).

REFERENCE EXAMPLE 22

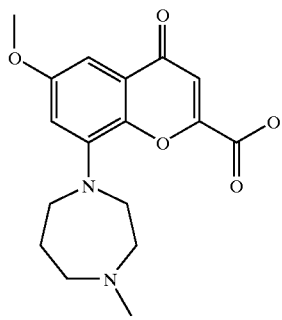

Preparation of 6-Methoxy-8-(4-methyl-[1,4]diazepan-1-yl)-4-oxo-4H-chromene-2-carboxylic acid

Reference Example 22a

6-Methoxy-8-(4-methyl-[1,4]diazepan-1-yl)-4-oxo-4H-chromene-2-carboxylic acid ethyl ester Into a 250 mL 3 neck round bottom flask equipped with a reflux condenser, nitrogen inlet and magnetic stirrer is placed 1.5 g (4.59 mmol, 1.0 equiv.) of 8-Bromo-6-methoxy-4-oxo-4H-chromene-2-carboxylic acid ethyl ester (Reference Example 2c), 84 mg (0.092 mmol, 0.02 equiv.) of tris dibenzylidineacetone dipalladium, 342 mg (0.55 mmol, 0.12 equiv.) of racemic 2,2'-bis(diphenylphosphino)-1,1'-binapthyl and 2 g of 4 A molecular sieves. To this in suspension is added 150 mL of dry toluene. To the stirred suspension is then added 628 mg, 684 μL, (5.50 mmol, 1.2 equiv.) of 1-methylhomopiperazine, followed by 2.05 g (6.3 mmol, 1.4 equiv.) of cesium carbonate. The mixture is then heated to 80° C. for 3 days. At the end of this time completion was monitored by LC/MS analysis of an aliquot. When the reaction was determined to be complete it was cooled to room temperature then filtered through a plug of diatomaceous earth with toluene washing to remove solid by products. Purification by flash chromatography, using a gradient of 5 to 20% methanol in methylene chloride as eluent, yielded 1.0 g, (60%) of the desired product.

Mass Spec.: calc. for $[C_{19}H_{24}N_2O_5+H]^+$ Theor. m/z=361; Obs.=361.

Reference Example 22b

6-Methoxy-8-(4-methyl-[1,4]diazepan-1-yl)-4-oxo-4H-chromene-2-carboxylic acid

Into a 125 mL erlenmeyer equipped with a magnetic stirrer is placed 319 mg (0.89 mmol, 1.0 equiv.) of 6-Methoxy-8-(4-methyl-[1,4]diazepan-1-yl)-4-oxo-4H-chromene-2-carboxylic acid ethyl ester. This material is dissolved in 30 mL of THF, then 30 mL of methanol are added. To this stirring solution is added 30 mL of a water containing 41 mg (0.97 mmol, 1.1 equiv.) of lithium hydroxide. This mixture is stirred at room temperature for 2 hr. Completion of the reaction is monitored by LC/MS, then 10 mL of 2N HCl is added. This mixture is then concentrated, dried and triturated with ether to give the product as the hydrochloride salt in quantitative yield.

Mass Spec.: calc. for $[C_{17}H_{20}N_2O_5+H]^+$ Theor. m/z=333; Obs.=333.

REFERENCE EXAMPLE 23

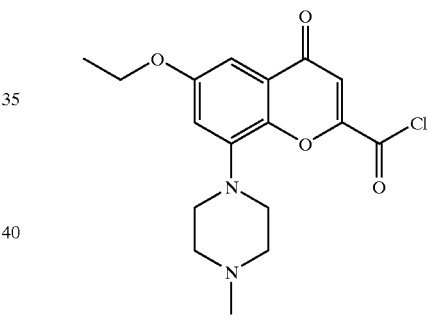

Preparation of 6-Ethoxy-8-(4-methyl-piperazin-1-yl)-4-oxo-4H-chromene-2-carbonyl chloride

Reference Example 23a

8-Bromo-6-hydroxy-4-oxo-4H-chromene-2-carboxylic acid ethyl ester

The hydroxy compound, 8-Bromo-6-hydroxy-4-oxo-4H-chromene-2-carboxylic acid ethyl ester, is formed as a side product during the synthesis of 8-Bromo-6-methoxy-4-oxo-4H-chromene-2-carboxylic acid ethyl ester. It can be separated from the crude methoxy compound by flash chromatography using a step gradient of 20% ethyl acetate in methylene chloride to the same solvent containing 2% methanol. The hydroxy compound, which elutes last, is concentrated to give the pure compound. Mass Spec.: calc. for $[C_{12}H_9BrO_5+H]^+$ Theor. m/z=313, 315; Obs.=313, 315.

Reference Example 23b

8-Bromo-6-ethoxy-4-oxo-4H-chromene-2-carboxylic acid ethyl ester

Into a 100 mL 3 neck round bottom flask equipped with a reflux condenser, nitrogen inlet and magnetic stirrer is added 700 mg (2.24 mg, 1.0 equiv.) of 8-Bromo-6-hydroxy-4-oxo-4H-chromene-2-carboxylic acid ethyl ester (Reference Example 23a). This material is dissolved in 50 mL of toluene, then 689 mg, 586 µL (4.47 mmol, 2.0 equiv.) of diethyl sulfate and 309 mg (2.24 mmol, 1.0 equiv.) of $K_2CO_3$ were added. The reaction was then heated to reflux for 24 hr. At the end of this time, monitoring by LC/MS reveals that the reaction is >than 95% complete. The reaction is then cooled, 100 mL of ethyl acetate is added and the organic layer is washed with 0.5N HCl solution, dried over $Na_2SO_4$, filtered and concentrated. The residues were subjected to flash chromatography, using 40% ethyl acetate in hexane as eluent. The purified fractions were concentrated to yield 500 mg (65%) of a colorless solid.

Mass Spec.: calc. for $[C_{14}H_{13}BrO_5+H]^+$ Theor. m/z=341, 343; Obs.=341, 343.

Reference Example 23c

6-Ethoxy-8-(4-methyl-piperazin-1-yl)-4-oxo-4H-chromene-2-carboxylic acid ethyl ester Into a 100 mL, 3 neck round bottom flask equipped with a reflux condenser, magnetic stirrer and nitrogen inlet is added 350 mg (1.03 mmol, 1.0 equiv.) of 8-Bromo-6-ethoxy-4-oxo-4H-chromene-2-carboxylic acid ethyl ester (Reference Example 23b), 18.9 mg (0.02 mmol, 0.02 equiv.) of tris dibenzylidineacetone dipalladium, 77 mg (0.123 mmol, 0.12 equiv.) of racemic 2,2'-bis(diphenylphosphino)-1,1'-binapthyl and 1 g of 4 A molecular sieves and 60 mL of dry toluene. To the stirred suspension is then added 113 mg, 1255 µL, (1.13 mmol, 1.1 equiv.) of 1-methylpiperazine, followed by 470 mg (1.44 mmol, 1.4 equiv.) of cesium carbonate. The mixture is then heated to 80° C. for 3 days. At the end of this time completion was monitored by LC/MS analysis of an aliquot. When the reaction was determined to be complete it was cooled to room temperature then filtered through a plug of diatomaceous earth, with toluene washing to remove solid by products. Purification by flash chromatography, using a gradient of 5 to 40% methanol in methylene chloride as eluent, yielded 350 mg (75%) of the desired product as a yellow solid. Mass Spec.: calc. for $[C_{19}H_{24}N_2O_5+H]^+$ Theor. m/z=361; Obs.=361.

Reference Example 23d

6-Ethoxy-8-(4-methyl-piperazin-1-yl)-4-oxo-4H-chromene-2-carboxylic acid

Into a 125 mL Erlenmeyer equipped with a magnetic stirrer is placed 500 mg (1.39 mmol, 1.0 equiv.) of 6-Ethoxy-8-(4-methyl-piperazin-1-yl)-4-oxo-4H-chromene-2-carboxylic acid ethyl ester (Reference Example 23c). This material is dissolved in 30 mL of THF, then 30 mL of methanol are added. To this stirring solution is added 30 mL of a water containing 64.2 mg (1.53 mmol, 1.1 equiv.) of lithium hydroxide. This mixture is stirred at room temperature for 2 hr. Completion of the reaction is monitored by LC/MS, then 10 mL of 2N HCl is added. This mixture is then concentrated, dried and triturated with ether to give the product as the hydrochloride salt in quantitative yield.

Mass Spec.: calc. for $[C_{17}H_{20}N_2O_5+H]^+$ Theor. m/z=333; Obs.=333.

Reference Example 23e

6-Ethoxy-8-(4-methyl-piperazin-1-yl)-4-oxo-4H-chromene-2-carbonyl chloride

Into a 100 mL round bottom flask equipped with a reflux condenser, nitrogen inlet and magnetic stirrer is placed 250 mg (0.68 mmol, 1.0 equiv.) of 6-Ethoxy-8-(4-methyl-piperazin-1-yl)-4-oxo-4H-chromene-2-carboxylic acid hydrochloride salt (Reference Example 23d) and 20 mL of methylene chloride. To the stirring suspension is then added 129.5 mg, 164 L (1.02 mmol, 1.5 equiv.) of oxalyl chloride followed by addition of one drop of DMF from a 50 microliter syringe to act as catalyst. The mixture is stirred for 2 hours, then concentrated to dryness on a rotary evaporator under a nitrogen atmosphere, followed by drying under high vacuum. The completeness of the reaction was ascertained by analysis of an aliquot, which was quenched with a THF solution of methylamine, by LC/MS. The crude material was used as obtained in the subsequent amidation reaction.

REFERENCE EXAMPLE 24

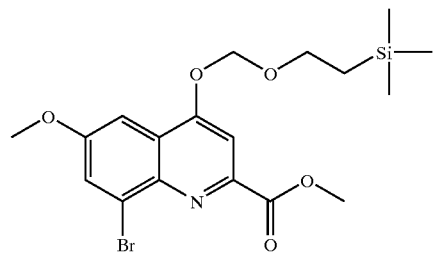

Preparation of 8-Bromo-6-methoxy-4-(2-trimethylsilanyl-ethoxymethoxy)-quinoline-2-carboxylic acid methyl ester Reference Example 24a 2-(2-Bromo-4-methoxy-phenylamino)-but-2-enedioic acid dimethyl ester A solution of 2-bromo-4-methoxy aniline (6.02 g, 29.8 mmol) in 125 mL anhydrous methanol was treated with dimethyl acetylenedicarboxylate (3.70 mL, 30.2 mmol) and the solution was heated at reflux under nitrogen for 8 hours. The reaction mixture was cooled, concentrated, and redissolved in hot methanol. Yellow crystals were obtained by filtration (6.93 g, 68%). A second crop of crystals was obtained from ethanol (0.942 g, 9%). The filtrates were combined and purified by flash chromatography on silica gel using 4:1 hexanes:ethyl acetate to afford an additional 1.63 g (16%) for a total yield of 93%. $^1$H NMR (300 MHz, DMSO, $d_6$) δ 9.60 (s, 1H, N$\underline{H}$), 7.26 (d, 1H, $J_m$=2.7 Hz, Ar $\underline{H}_3$), 6.93 (dd, 1H, $J_o$=8.7, $J_m$=2.7 Hz, Ar$\underline{H}_5$), 6.87 (d, 1H, $J_o$=8.7 Hz, Ar$\underline{H}_6$), 5.34 (s, 1H, C=C$\underline{H}$), 3.76 (s, 3H, OC$\underline{H}_3$), 3.68 (s, 3H, CHCO$_2$C$\underline{H}_3$), 3.66 (s, 3H, CNCO$_2$C$\underline{H}_3$); Mass Spec.: calc. for $[C_{13}H_{14}BrNO_5+H]^+$ Theor. m/z=344, 346; Obs. 344, 346.

Reference Example 24b

8-Bromo-6-methoxy-4-oxo-1,4-dihydro-quinoline-2-carboxylic acid methyl ester

Dow-Therm (175 mL) was heated to 244° C. and the 2-(2-bromo-4-methoxy-phenylamino)-but-2-enedioic acid dimethyl ester (9.50 g, 27.6 mmol) was added as a solid in portions over 7 minutes while maintaining a temperature of 230–240° C. The brown reaction mixture was heated at 240–245° C. for 45 minutes and then cooled to room temperature. A yellow precipitate formed upon cooling. Approximately 100 mL of hexanes were added to the mixture and the solids were isolated by filtration, washed with additional hexanes, and dried under high vacuum to afford the product as a yellow solid (6.73 g, 78%). $^1$H NMR (300 MHz, DMSO, d$_6$) δ 12.01 (s, 1H, N$\underline{H}$), 7.86 (d, 1H, J$_m$=2.7 Hz, Ar$\underline{H}_5$), 7.52 (s, 1H, C=C$\underline{H}$), 7.48 (d, 1H, J$_m$=2.7 Hz, Ar$\underline{H}_7$), 3.93 (s, 6H, OC$\underline{H}_3$ and CO$_2$C$\underline{H}_3$); Mass Spec.: calc. for [C$_{12}$H$_{10}$BrNO$_4$+H]$^+$ Theor. m/z=312, 314; Obs. 312, 314.

Reference Example 24c

8-Bromo-6-methoxy-4-(2-trimethylsilanyl-ethoxymethoxy)-quinoline-2-carboxylic acid methyl ester A brown solution of 8-bromo-6-methoxy-4-oxo-1,4-dihydro-quinoline-2-carboxylic acid methyl ester (6.73 g, 21.6 mmol) in 100 mL N-methyl pyrolidinone was treated with sodium hydride (60% dispersion in oil, 1.028 g, 25.7 mmol). Gas evolution and warming were observed. The reaction was stirred for 10 minutes at room temperature under nitrogen. Addition of 2-(trimethylsilyl)ethoxymethyl chloride (5.00 mL, 28.3 mmol) resulted in a slightly cloudy, light brown solution. After 2.5 hours at room temperature, the reaction mixture was poured into 800 mL water and stirred for 15 minutes. The resulting cream colored precipitate was isolated by filtration, washed with water, and dried under high vacuum to afford the product as a cream colored solid (9.70 g, quantitative yield). $^1$H NMR (300 MHz, DMSO, d$_6$) δ 7.976 (d, 1H, J$_m$=2.7 Hz, Ar$\underline{H}_7$), 7.79 (s, 1H, C=C$\underline{H}$), 7.53 (d, 1H, J$_m$=2.7 Hz, Ar$\underline{H}_5$), 5.70 (s, 2H, OC$\underline{H}_2$O), 3.99 (s, 6H, OC$\underline{H}_3$ and CO$_2$C$\underline{H}$), 3.88 (t, 2H, J=8.0 Hz, OC$\underline{H}_2$CH$_2$Si), 0.97 (t, 2H, J=8.0 Hz, OCH$_2$C$\underline{H}_2$Si), −0.04 (s, 9H, Si(C$\underline{H}_3$)$_3$; Mass Spec.: calc. for [C$_{18}$H$_{24}$BrNO$_5$Si+H]$^+$ Theor. m/z=442, 444; Obs. 442, 444.

REFERENCE EXAMPLE 25

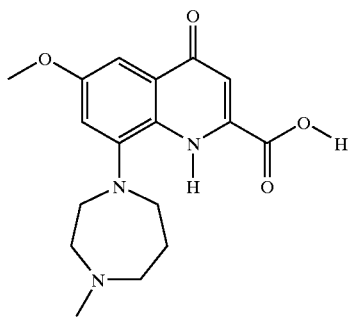

Preparation of 6-Methoxy-8-(4-methyl-[1,4]diazepan-1-yl)-4-oxo-1,4-dihydro-quinoline-2-carboxylic acid Reference Example 25a 6-Methoxy-8-(4-methyl-[1,4]diazepan-1-yl)-4-(2-trimethylsilanyl-ethoxymethoxy)-quinoline-2-carboxylic acid methyl ester To a clear, light brown solution of 2-bromo-6-methoxy-4-(2-trimethylsilanyl-ethoxymethoxy)-quinoline-2-carboxylic acid methyl ester (1.01 g, 2.28 mmol), N-methylhomopiperazine (0.32 mL, 2.57 mmol), and 4 Å sieves in 30 mL anhydrous toluene was added Pd$_2$(dba)$_2$ (43.8 mg, 0.048 mmol) and BINAP (169.8 mg, 0.27 mmol). The resulting wine colored solution was treated with cesium carbonate (1.124 g, 3.45 mmol). The reaction mixture was heated at reflux under nitrogen for 21 hours. The pea green reaction mixture was cooled to room temperature and concentrated. The crude mixture was purified by flash chromatography on silica gel using a gradient of 95:5 to 40:60 methylene chloride:methanol to afford the desired product as a yellow foam (1.004 g, 92%). $^1$H NMR (300 MHz, DMSO, d$_6$) δ 7.67 (s, 1H, Ar$\underline{H}_3$), 6.94 (d, 1H, J$_m$=2.4 Hz, Ar$\underline{H}_5$), 6.66 (d, 1H, J$_m$=2.4 Hz, Ar$\underline{H}_7$), 5.60 (s, 2H, OC$\underline{H}_2$O), 3.94 (s, 3H, CO$_2$C$\underline{H}_3$), 3.88 (s, 3H, OC$\underline{H}_3$), 3.82 (t, 2H, J=8.0 Hz, OC$\underline{H}_2$CH$_2$Si), 3.75 (bs, 4H, ArNC$\underline{H}_2$CH$_2$CH$_2$NCH$_3$ & ArNC$\underline{H}_2$CH$_2$N—CH$_3$), 3.45 (bs, 2H, ArNCH$_2$C$\underline{H}_2$NCH$_3$), 3.31 (bs, 2H, ArNCH$_2$CH$_2$C$\underline{H}_2$NCH$_3$), 2.83 (s, 3H, NC$\underline{H}_3$), 2.28 (bs, 2H, ArNCH$_2$C$\underline{H}_2$CH$_2$NCH$_3$), 0.92 (t, 2H, J=8.0 Hz, OCH$_2$C$\underline{H}_2$Si), 0.04 (s, 9H, Si(C$\underline{H}_3$)$_3$; Mass Spec.: calc. for [C$_{24}$H$_{37}$N$_3$O$_5$Si+H]$^+$ Theor. m/z=476; Obs. 476.

Reference Example 25b

6-Methoxy-8-(4-methyl-[1,4]diazepan-1-yl)-4-oxo-1,4-dihydro-quinoline-2-carboxylic acid To a light brown solution of 6-methoxy-8-(4-methyl-[1,4]diazepan-1-yl)-4-(2-trimethylsilanyl-ethoxymethoxy)-quinoline-2-carboxylic acid methyl ester (1.00 g, 2.10 mmol) in 18 mL 3:1:1 tetrahydrofuran:methanol:water was added lithium hydroxide monohydrate (0.267 g, 6.35 mmol). The reaction mixture was stirred at room temperature for 5 hours, acidified to pH 4 with 1 N HCl, and stirred an additional 20 minutes. The reaction mixture was concentrated and dried under high vacuum to afford an orange foam. $^1$H NMR (300 MHz, DMSO, d$_6$) δ 11.06 (s, 1H, N$\underline{H}$), 7.53 (s, 1H, C=C$\underline{H}$), 7.00 (d, 1H, J$_m$=2.4 Hz, Ar$\underline{H}_5$), 6.70 (d, 1H, J$_m$=2.4 Hz, Ar$\underline{H}_7$), 4.05–3.99 (m, 2H, ArNC$\underline{H}_2$CH$_2$CH$_2$NCH$_3$), 3.87 (s, 3H, OC$\underline{H}_3$), 3.68–3.60 (m, 2H, ArNC$\underline{H}_2$CH$_2$NCH$_3$), 3.54–3.47 (m, 2H, ArNCH$_2$C$\underline{H}_2$NCH$_3$), 3.41–3.26 (m, 2H, ArNCH$_2$CH$_2$C$\underline{H}_2$NCH$_3$), 2.82 (d, 3H, J=4.8 Hz, NC$\underline{H}_3$), 2.46–2.41 (m, 1H, ArNCH$_2$C$\underline{H}_2$CH$_2$NCH$_3$), 2.30–2.25 (m, 1H, ArNCH$_2$C$\underline{H}_2$CH$_2$NCH$_3$); Mass Spec.: calc. for [C$_{17}$H$_{21}$N$_3$O$_4$+H]$^+$ Theor. m/z 332; Obs. 332.

REFERENCE EXAMPLE 26

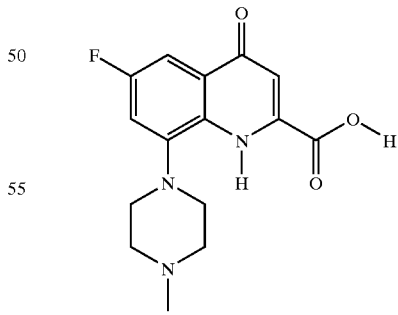

Preparation of 6-Fluoro-8-(4-methylpiperazin-1-yl)-4-oxo-1,4-dihydroquinoline-2-carboxylic acid This compound was prepared via the same procedure described for preparation of Reference Example 25.

REFERENCE EXAMPLE 27

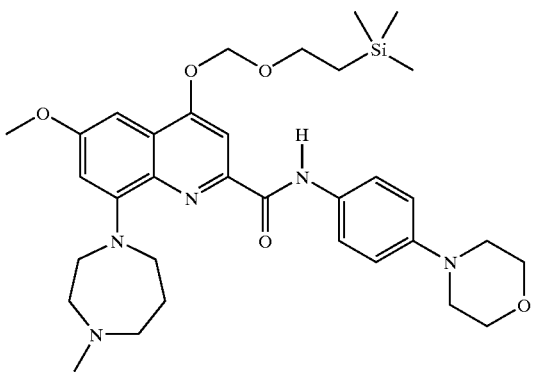

Preparation of 6-Methoxy-8-(4-methyl-[1,4]
diazepan-1-yl)-4-(2-trimethylsilanyl-
ethoxymethoxy)-quinoline-2-carboxylic acid (4-
morpholin-4-yl-phenyl)-amide

Reference Example 27a

8-Bromo-6-methoxy-4-oxo-1,4-dihydro-quinoline-2-
carboxylic acid

To a light brown solution of 8-bromo-6-methoxy-4-(2-trimethylsilanyl-ethoxymethoxy)-quinoline-2-carboxylic acid methyl ester (Reference Example 24c) (4.98 g, 11.3 mmol) in 75 mL 3:1:1 tetrahydrofuran:methanol:water was added lithium hydroxide monohydrate (1.367 g, 32.6 mmol). The reaction was stirred at room temperature for 5 hours. The reaction mixture was concentrated and then poured into water. The solution was acidified to pH 2 with 1 N HCl and the resulting solids were isolated by filtration. The solids were then suspended in methanol and filtered to afford the desired product (2.6732 g, 80%). An additional 0.5768 g (17%) of product was obtained from the methanol filtrates. $^1$H NMR (300 MHz, DMSO, d$_6$, TFA Shake) δ 7.86 (d, 1H, J$_m$=2.7 Hz, ArH$_5$), 7.55 (d, 1H, J$_m$=2.7 Hz, ArH$_7$), 7.32 (s, 1H, C=CH), 3.94 (s, 3H, OCH$_3$); Mass Spec.: calc. for [C$_{11}$H$_8$BrNO$_4$+H]$^+$ Theor. m/z=298, 300; Obs.=298, 300.

Reference Example 27b

8-Bromo-6-methoxy-4-oxo-1,4-dihydro-quinoline-2-
carboxylic acid (4-morpholin-4-yl-phenyl)-amide To a yellow suspension of 8-bromo-6-methoxy-4-oxo-1,4-dihydroquinoline-2-carboxylic acid (Reference Example 27a) (3.446 g, 11.56 mmol), TBTU (9.039 g, 28.15 mmol), and HOBT (3.757 g, 27.8 mmol) in 100 mL dimethylformamide was added 4-morpholinoaniline (2.733 g, 15.3 mmol) and diisopropylethyl amine (8.2 mL, 50.2 mmol). The resulting maroon solution was stirred at room temperature under nitrogen for 16 hours during which time the reaction became greenish brown and formed a large amount of precipitate. The reaction mixture was filtered and the solids washed with dimethylformamide, water, and methanol. Drying under high vacuum afforded the desired product as a yellow solid (3.09 g, 58%). $^1$H NMR (300 MHz, DMSO, d$_6$) δ 12.13 (s, 1H, NH), 10.18 (s, 1H, C(O)NH), 7.90 (d, 1H, J$_m$=2.7 Hz, ArH$_5$), 7.68 (d, 2H, J$_o$=9.0 Hz, ArH$_2$' & H$_6$'), 7.63 (s, 1H, C=CH), 7.51 (d, 1H, J$_m$=2.7 Hz, ArH$_7$), 7.00 (d, 2H, J$_o$=9.0 Hz, ArH$_3$' & H$_5$'), 3.94 (s, 3H, OCH$_3$), 3.75 (t, 4H, J=4.8 Hz, OCH$_2$CH$_2$N), 3.10 (t, 4H, J=4.8 Hz, OCH$_2$CH$_2$N); Mass Spec.: calc. for [C$_{21}$H$_{20}$BrN$_3$O$_4$+H]$^+$ Theor. m/z=458, 460; Obs.=458, 460.

Reference Example 27c

8-Bromo-6-methoxy-4-(2-trimethylsilanyl-
ethoxymethoxy)-quinoline-2-carboxylic acid (4-
morpholin-4-yl-phenyl)-amide.

A yellow suspension of 8-bromo-6-methoxy-4-oxo-1,4-dihydro-quinoline-2-carboxylic acid (4-morpholin-4-yl-phenyl)-amide (Reference Example 27b) (3.092 g, 6.75 mmol) in 40 mL N-methylpyrolidinone was treated with sodium hydride (60% dispersion in oil, 0.410 g, 10.24 mmol). Gas evolution and warming were observed and the suspension became light brown and almost clear. The reaction was stirred for 10 minutes at room temperature under nitrogen. Addition of the 2-(trimethylsilyl)ethoxymethyl chloride (1.6 mL, 9.1 mmol) resulted in a slightly cloudy, lighter brown solution. After 4.5 hours at room temperature, the reaction mixture was poured into 300 mL water, stirred for 15 minutes and then stored at 0° C. overnight. The solids were isolated by filtration, suspended in methanol, filtered again, and dried under high vacuum to afford the product as a yellow solid (3.190 g, 80%). $^1$H NMR (300 MHz, DMSO, d$_6$) δ 10.18 (s, 1H, C(O)NH), 7.95 (d, 1H, J$_m$=2.4 Hz, ArH$_7$), 7.83 (s, 1H, ArH$_3$), 7.69 (d, 2H, J$_o$=9.0 Hz, ArH$_2$' & H$_6$'), 7.51 (d, 1H, J$_m$=2.7 Hz, ArH$_5$), 7.00 (d, 2H, J$_o$=9.0 Hz, ArH$_3$' & H$_5$'), 5.69 (s, 2H, OCH$_2$O), 3.95 (s, 3H, OCH$_3$), 3.85 (t, 2H, J=8.0 Hz, OCH$_2$CH$_2$Si), 3.75 (t, 4H, J=4.7 Hz, OCH$_2$CH$_2$N), 3.10 (t, 4H, J=4.7 Hz, OCH$_2$CH$_2$N), 0.94 (t, 2H, J=8.0 Hz, OCH$_2$CH$_2$Si), −0.04 (s, 9H, Si(CH$_3$)$_3$; Mass Spec.: calc. for [C$_{27}$H$_{34}$BrN$_3$O$_5$Si+H]$^+$ Theor. m/z=588, 590; Obs.=588, 590.

Reference Example 27d

6-Methoxy-8-(4-methyl-[1,4]diazepan-1-yl)-4-(2-
trimethylsilanyl-ethoxymethoxy)-quinoline-2-
carboxylic acid (4-morpholin-4-yl-phenyl)-amide To a yellow-green suspension of 8-bromo-6-methoxy-4-(2-trimethylsilanyl-ethoxymethoxy)-quinoline-2-carboxylic acid (Reference Example 27c) (4-morpholin-4-yl-phenyl)-amide (1.155 g, 1.96 mmol), N-methyl homopiperazine (0.39 mL, 3.14 mmol), and 4 Å sieves in 30 mL anhydrous toluene was added Pd$_2$(dba)$_2$ (90.0 mg, 0.098 mmol) and BINAP (0.358 g, 0.58 mmol). The resulting reddish brown mixture became lighter in color upon treatment with cesium carbonate (2.544 g, 7.81 mmol). The reaction mixture was heated at reflux under nitrogen for 17 hours. The clear brown solution was cooled to room temperature, concentrated, and then purified by flash chromatography on silica gel using a slow gradient of 95:5 to 50:50 methylene chloride:methanol to afford the desired product (0.989 g, 81%). $^1$H NMR (300 MHz, DMSO, d$_6$) δ 9.88 (s, 1H, NH), 7.73 (s, 1H, ArH$_3$), 7.68 (d, 2H, J$_o$=8.9 Hz, ArH$_2$' & H$_6$'), 7.00 (d, 2H, J$_o$=8.9 Hz, ArH$_3$' & H$_5$'), 6.94 (d, 1H, J$_m$=2.7 Hz, ArH$_5$), 6.66 (d, 1H, J$_m$=2.7 Hz, ArH$_7$), 5.62 (s, 2H, OCH$_2$O), 3.87 (s, 3H, OCH$_3$), 3.80 (t, 2H, J=8.0 Hz, OCH$_2$CH$_2$Si), 3.73 (t, 4H, J=4.7 Hz, OCH$_2$CH$_2$N), 3.63 (t, 2H, J=5.9 Hz, ArNCH$_2$CH$_2$CH$_2$NCH$_3$), 3.33 (bs, 2H, ArNCH$_2$CH$_2$NCH$_3$), 3.09 (t, 4H, J=4.7 Hz, OCH$_2$CH$_2$N), 2.97 (bs, 2H, ArNCH$_2$CH$_2$NCH$_3$), 2.69 (bs, 2H, ArNCH$_2$CH$_2$CH$_2$CH$_3$), 2.35 (s, 3H, NCH$_3$), 2.09 (bs, 2H, ArNCH$_2$CH$_2$CH$_2$NCH$_3$), 0.94 (t, 2H, J=8.0 Hz, OCH$_2$CH$_2$Si), −0.03 (s, 9H, Si(CH$_3$)$_3$; Mass Spec.: calc. for [C$_{33}$H$_{47}$N$_5$O$_5$Si+H]$^+$ Theor. m/z=622; Obs.=622.

REFERENCE EXAMPLE 28

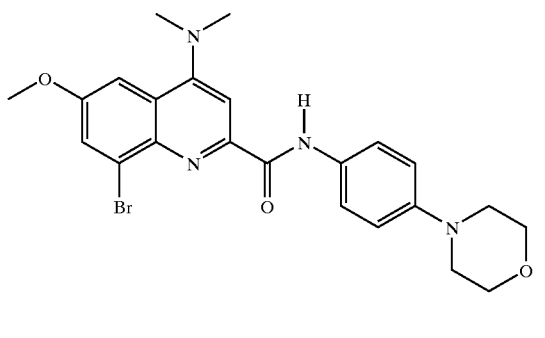

Preparation of 8-Bromo-4-dimethylamino-6-methoxy-quinoline-2-carboxylic acid (4-morpholin-4-yl-phenyl)-amide

Reference Example 28a

8-Bromo-4-chloro-6-methoxy-quinoline-2-carboxylic acid (4-morpholin-4-yl-phenyl)-amide A suspension of 8-bromo-6-methoxy-4-oxo-1,4-dihydro-quinoline-2-carboxylic acid (Reference Example 27b) (1.75 mmol) in 20 mL methylene chloride was treated with oxalyl chloride (1.5 mL, 17.2 mmol) and catalytic dimethylformamide (3 drops). The reaction mixture bubbled vigorously and became clearer. The reaction was heated at reflux for 2 hours, cooled to room temperature, and concentrated to a pale yellow solid (kept under nitrogen).

To a yellow solution of the acid chloride in 20 mL methylene chloride was added 4-morpholinoaniline (0.347 g, 1.94 mmol) and diisopropylethyl amine (1.0 mL, 6.1 mmol). The solution became orange and gas evolution was observed. Within 30 minutes, solids began to precipitate from the solution. The reaction was stirred at room temperature for 1 hour. The solids were isolated by filtration and dried under high vacuum to afford the desired product (0.406 g, 49%). $^1$H NMR (300 MHz, DMSO, $d_6$) δ 10.15 (s, 1H, C(O)N$\underline{H}$), 8.33 (s, 1H, Ar$\underline{H}_3$), 8.10 (d, 1H, $J_m$=2.7 Hz, Ar$\underline{H}_7$), 7.70 (d, 2H, $J_o$=9.0 Hz, Ar$\underline{H}_{2'}$ & $\underline{H}_{6'}$), 7.56 (d, 1H, $J_m$=2.7 Hz, Ar$\underline{H}_5$), 7.01 (d, 2H, $J_o$=9.0 Hz, Ar$\underline{H}_{3'}$ & $\underline{H}_{5'}$), 4.06 (s, 3H, OC$\underline{H}_3$), 3.75 (t, 4H, J=4.8 Hz, OC$\underline{H}_2$CH$_2$N), 3.11 (t, 4H, J=4.8 Hz, OCH$_2$C$\underline{H}_2$N); Mass Spec.: calc. for [C$_{21}$H$_{19}$BrClN$_3$O$_3$+H]$^+$ Theor. m/z=476, 478; Obs.=476, 478.

Reference Example 28b

8-Bromo-4-dimethylamino-6-methoxy-quinoline-2-carboxylic acid (4-morpholin-4-yl-phenyl)-amide A solution of 8-bromo-4-chloro-6-methoxy-quinoline-2-carboxylic acid (4-morpholin-4-yl-phenyl)-amide (Reference Example 28a) (0.1512 g, 0.317 mmol) in 100 mL 2.0 M dimethyl amine in tetrahydrofuran was heated at 100° C. in a Parr bomb. The initial pressure was 75–80 psi and then remained at approximately 60 psi. After 18 hours, the reaction was cooled to room temperature, concentrated and dried to afford the crude product as a brown solid. Purification on silica gel using a gradient of 100:0 to 95:5 methylene chloride:methanol afforded the clean product (0.142 g, 92%); $^1$H NMR (300 MHz, DMSO, $d_6$) δ 10.20 (s, 1H, C(O)N$\underline{H}$), 7.90 (d, 1H, $J_m$=2.7 Hz, Ar$\underline{H}_5$), 7.69 (d, 2H, $J_o$=9.0 Hz, Ar$\underline{H}_{2'}$ & $\underline{H}_{6'}$), 7.60 (s, 1H, Ar$\underline{H}_3$), 7.41 (d, 1H, $J_m$=2.7 Hz, Ar$\underline{H}_7$), 7.01 (d, 2H, J=9.0 Hz, Ar$\underline{H}_{3'}$ & $\underline{H}_{5'}$), 3.96 (s, 3H, OC$\underline{H}_3$), 3.75 (t, 4H, J=4.8 Hz, OC$\underline{H}_2$CH$_2$N), 3.10 (t, 4H, J=4.8 Hz, OCH$_2$C$\underline{H}_2$N), 3.08 (s, 6H, N(C$\underline{H}_3$)$_2$); Mass Spec.: calc. for [C$_{21}$H$_{19}$BrClN$_3$O$_3$+H]$^+$ Theor. m/z=485, 487; Obs.=485, 487.

REFERENCE EXAMPLE 29

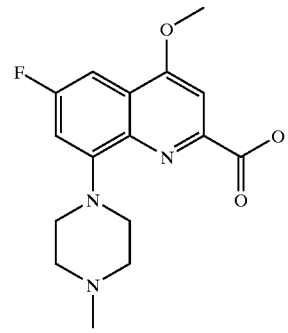

Preparation of 6-Fluoro-4-methoxy-8-(4-methyl-piperazin-1-yl)-quinoline-2-carboxylic acid

Reference Example 29a

8-Bromo-6-fluoro-4-methoxy-quinoline-2-carboxylic acid methyl ester

Into a 150 mL 3 neck round bottom flask equipped with a reflux condenser, magnetic stirrer and nitrogen inlet is placed 2.0 g (6.76 mmol, 1.0 equiv.) of 8-Bromo-6-fluoro-4-oxo-1,4-dihydro-quinoline-2-carboxylic acid methyl ester. This material is then dissolved in 50 mL of NMP. Then 300 mg (7.44 mmol, 1.1 equiv.) of a 60% dispersion of sodium hydride in oil is cautiously added portion-wise to the solution at room temperature. A yellow color then develops, indicating that formation of the anion has occurred, with hydrogen evolution. Stirring of the anion solution is continued for one hour, then 1.14 g, 500 μL (8.04 mmol, 1.2 equiv.) of iodomethane is added via syringe. The mixture is allowed to react for two hours additional, then is cautiously quenched with 20 mL of water. The solids, which precipitate upon dilution in 1 L of water, are collected by filtration, then washed with water to give the pure O methylated material as 2.1 g (98%) of a colorless solid.

Mass Spec.: calc. for [C$_{12}$H$_9$BrFNO$_3$+H]$^+$ Theor. m/z= 314, 316; Obs.=314, 316.

Alternatively, into a 100 mL 3 neck round bottom flask equipped with a reflux condenser, nitrogen inlet and magnetic stirrer is placed 350 mg (1.17 mmol, 1.0 equiv.) of 8-Bromo-6-fluoro-4-oxo-1,4-dihydro-quinoline-2-carboxylic acid methyl ester and 242 mg (1.75 mmol, 1.5 equiv.) of K$_2$CO$_3$. This material is suspended in 20 mL of DMSO then heated to 70° C. for 1 hr. The anion formation of the anion is apparent when the mixture becomes cloudy. The mixture is allowed to cool to 35° C. then 331 mg, 145 μL (2.33 mmol, 2.0 equiv.) of methyl iodide are added and stirring is continued for 2 hr. At the end of this time it is determined if the reaction is complete by LC/MS. Upon completion the mixture is poured into 200 mL of water and the solids which form are collected by filtration and washed with water to give 340 mg (93%) of the O-methylated product after drying.

Reference Example 29b

6-Fluoro-4-methoxy-8-(4-methyl-piperazin-1-yl)-quinoline-2-carboxylic acid methyl ester Into a 250 mL, 3 neck round bottom flask equipped with a reflux condenser, magnetic stirrer and nitrogen inlet is added 2.1 g (6.68 mmol, 1.0 equiv.) of 8-Bromo-6-fluoro-4-methoxy-quinoline-2-carboxylic acid methyl ester (Reference Example 29a) (122 mg, 0.134 mmol, 0.02 equiv.) of tris dibenzylidineacetone dipalladium, 499 mg (0.802 mmol, 0.12 equiv.) of racemic 2,2'-bis(diphenylphosphino)-1,1'-binapthyl and 1 g of 4 A molecular sieves and 80 mL of dry toluene. To the stirred suspension is then added 736 mg, 815 μL, (7.35 mmol, 1.1 equiv.) of 1-methylpiperazine, followed by 3.05 g (9.35 mmol, 1.4 equiv.) of cesium carbonate. The mixture is then heated to 80° C. for 36 hr. At the end of this time completion was monitored by LC/MS analysis of an aliquot. When the reaction was determined to be complete it was cooled to room temperature then filtered through a plug of celite, with toluene washing to remove solid by products. Purification by flash chromatography using a gradient of 5 to 20% methanol in methylene chloride as eluent yielded 2.0 g, (90%) of the desired product. Mass Spec.: calc. for $[C_{17}H_{20}FN_3O_3+H]^+$ Theor. m/z=334; Obs.=334.

Reference Example 29c

6-Fluoro-4-methoxy-8-(4-methyl-piperazin-1-yl)-quinoline-2-carboxylic acid

Into a 125 mL erlenmeyer flask containing 30 mL of THF and 30 mL of methanol is placed 2.1 g (6.3 mmol) of 6-Fluoro-4-methoxy-8-(4-methyl-piperazin-1-yl)-quinoline-2-carboxylic acid methyl ester (Reference Example 29b). To this solution is added with stirring 30 mL of water in which is dissolved 291 mg (6.9 mmol, 1.1 equiv.) of lithium hydroxide monohydrate. This solution is allowed to react for 1 hr then is quenched with 10 mL of 2N HCl solution. The solution is then filtered and the solids washed with 10 mL of 0.5 N HCl solution. The combined filtrates are then concentrated to give 2.15 g, (95%) of the solid yellow product as the hydrochloride salt. Mass Spec.: calc. for $[C_{16}H_{18}FN_3O_3+H]^+$ Theor. m/z=320; Obs.=320.

EXAMPLE 1

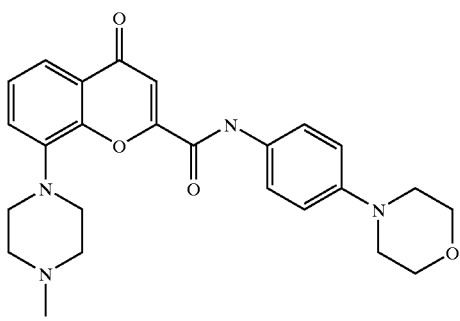

8-(4-methyl-1-piperazinyl)-N-[4-(4-morpholinyl) phenyl]-4-oxo-4H-chromene-2-carboxamide 8-(4-methyl-1-piperazinyl)-4-oxo-4H-chromene-2-carboxylic acid hydrochloride (Reference Example 1) (400 mg, 1.23 mmol) was suspended in anhydrous N,N-dimethylformamide (20 ml) and triethylamine (0.69 ml, 4.92 mmol) was added to give a clear solution. The following were added in order: 1-hydroxybenzotriazole (HOBt (205 mg, mol)), O-(1H-Benzotriazol-1-yl-N,N,N',N'-pentamethylene-uronium tetrafluoroborate (TBTU (435 mg, 3.1 mmol)) then 4-(dimethylamino)pyridine (25 mg). After stirring for 5 min at room temperature, 4-(4-morpholinyl) aniline (Reference Example 21) (220 mg, mmol). The reaction stirred overnight at room temperature. The solution was concentrated in vacuo, the remains were partitioned between chloroform/saturated sodium bicarbonate, extracted (×3) with chloroform, dried (MgSO$_4$) and concentrated in vacuo to give the crude product.

Chromatography on silica (230–400 mesh ASTM) and eluting ethyl acetate followed by 2.5–5% methanol/chloroform gave 190 mg (% yield) of 8-(4-methyl-1-piperazinyl)-N-[4-(4-morpholinyl)phenyl]-4-oxo-4H-benzochromene-2-carboxamide as a yellow solid (mp 217–218° decomposition and melt 244–247 C). LC/MS (M+1) m/z 449.

EXAMPLE 2

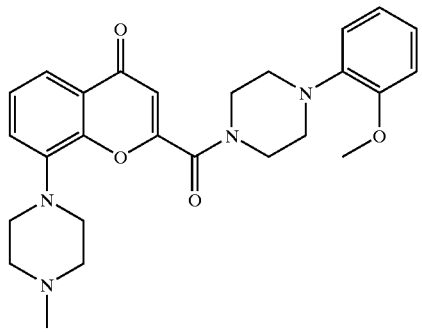

2-{1-[4-(2-Methoxy-phenyl)-piperazin-1-yl]-methanoyl}-8-(4-methyl-piperazin-1-yl)-1-chromen-4-one This compound was prepared from 8-(4-Methyl-piperazin-1-yl)-4-oxo-4H-chromene-2-carboxylic acid hydrochloride (Reference Example 1) and commercially available 1-(2-Methoxy-phenyl)-piperazine (Aldrich) via the same procedure used in example 1, yielding a yellow solid. MS (M+H) m/z=463.

EXAMPLE 3

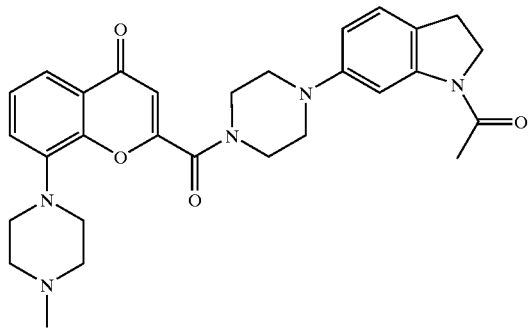

2-{1-[4-(1-Acetyl-2,3-dihydro-1H-indol-6-yl)-piperazin-1-yl]-methanoyl}-8-(4-methyl-piperazin-1-yl)-chromen-4-one This compound was prepared from 8-(4-Methyl-piperazin-1-yl)-4-oxo-4H-chromene-2-carboxylic acid hydrochloride (Reference Example 1) and 1-(6-Piperazin-1-yl-2,3-dihydro-indol-1-yl)-ethanone (Reference Example 8) as prepared in Example 1, yielding a yellow solid. MS (M+H) m/z=516.

EXAMPLE 4

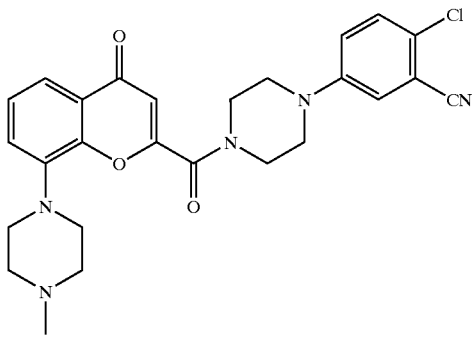

2-Chloro-5-(4-{1-[8-(4-methyl-piperazin-1-yl)-4-oxo-4H-chromen-2-yl]-methanoyl}-piperazin-1-yl) benzonitrile This compound was prepared from 8-(4-Methyl-piperazin-1-yl)-4-oxo-4H-chromene-2-carboxylic acid hydrochloride (Reference Example 1) and 2-chloro-5-piperazin-1-yl benzonitrile (Reference Example 9) as prepared in Example 1, yielding a yellow solid. MS (M+H) m/z=493.

EXAMPLE 5

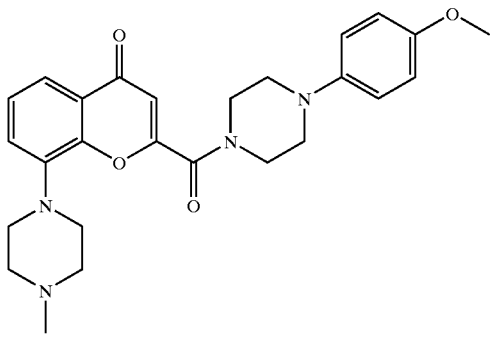

2-{1-[4-(4-Methoxy-phenyl)-piperazin-1-yl]-methanoyl}-8-(4-methyl-piperazin-1-yl)-chromen-4-one This compound was prepared from 8-(4-Methyl-piperazin-1-yl)-4-oxo-4H-chromene-2-carboxylic acid hydrochloride (Reference Example 1) and commercially available (Aldrich) 1-(4-Methoxy-phenyl)-piperazine as prepared in example 1, yielding a yellow solid. MS (M+H) m/z=463.

EXAMPLE 6

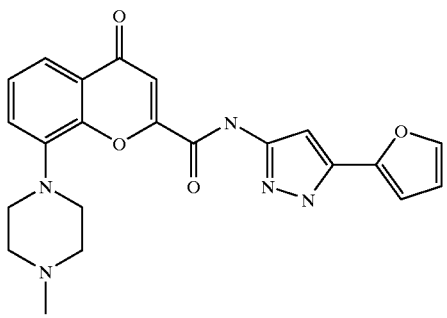

8-(4-Methyl-piperazin-1-yl)-4-oxo-4H-chromene-2-carboxylic acid (5-furan-2-yl-1H-pyrazol-3-yl)-amide This compound was prepared from 8-(4-Methyl-piperazin-1-yl)-4-oxo-4H-chromene-2-carboxylic acid hydrochloride (Reference Example 1) and commercially available 5-furan-2-yl-1H-pyrazol-3-ylamine (Maybridge) as prepared in example 1, yielding a yellow solid. MS (M+H) m/z=420.

EXAMPLE 7

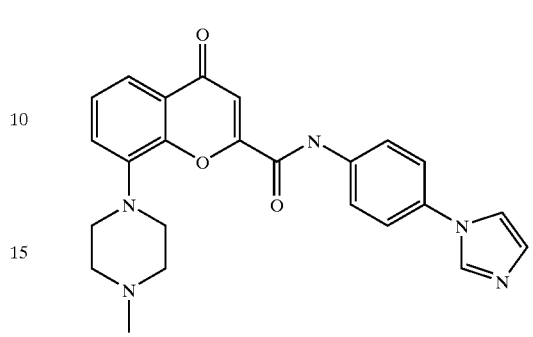

8-(4-Methyl-piperazin-1-yl)-4-oxo-4H-chromene-2-carboxylic acid (4-imidazol-1-yl-phenyl)-amide This compound was prepared from 8-(4-Methyl-piperazin-1-yl)-4-oxo-4H-chromene-2-carboxylic acid hydrochloride (Reference Example 1) and commercially available 4-imidazol-1-yl-phenylamine (Aldrich) as prepared in Example 1, yielding a yellow solid. MS (M+H) m/z=430.

EXAMPLE 8

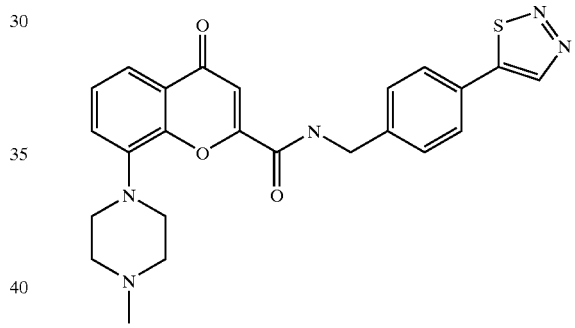

8-(4-Methyl-piperazin-1-yl)-4-oxo-4H-chromene-2-carboxylic acid (4-[1,2,3]thiadiazol-5-yl-phenyl)-amide This compound was prepared from 8-(4-Methyl-piperazin-1-yl)-4-oxo-4H-chromene-2-carboxylic acid hydrochloride (Reference Example 1) and 4-[1,2,3]thiadiazol-5-yl-phenylamine (Reference Example 10) as prepared in Example 1, yielding a yellow solid. MS (M+H) m/z=448.

EXAMPLE 9

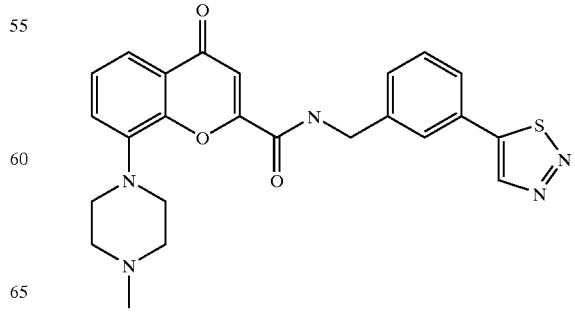

8-(4-Methyl-piperazin-1-yl)-4-oxo-4H-chromene-2-carboxylic acid 4-[1,2,3]thiadiazol-5-yl-benzylamide This compound was prepared from 8-(4-Methyl-piperazin-1-yl)-4-oxo-4H-chromene-2-carboxylic acid hydrochloride (Reference Example 1) and commercially available (Maybridge) 4-[1,2,3]thiadiazol-5-yl-benzylamine as prepared in Example 1, yielding a yellow solid. MS (M+H) m/z=462.

EXAMPLE 10

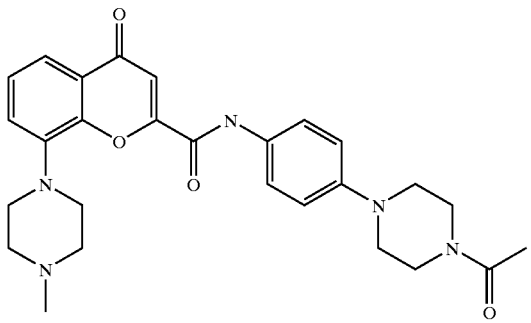

8-(4-Methyl-piperazin-1-yl)-4-oxo-4H-chromene-2-carboxylic acid [4-(4-acetyl-piperazin-1-yl)-phenyl]-amide This compound was prepared from 8-(4-Methyl-piperazin-1-yl)-4-oxo-4H-chromene-2-carboxylic acid hydrochloride (Reference Example 1) and 1-[4-(4amino-phenyl)-piperazin-1-yl]-ethanone (Reference Example 11) as prepared in Example 1, yielding a yellow solid.

MS (M+H) m/z=499.

EXAMPLE 11

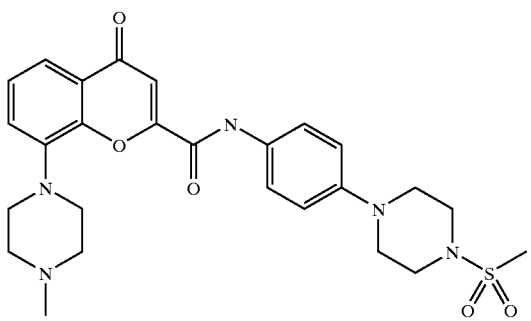

8-(4-Methyl-piperazin-1-yl)-4-oxo-4H-chromene-2-carboxylic acid [4-(4-methanesulfonyl-piperazin-1-yl)-phenyl]-amide This compound was prepared from 8-(4-Methyl-piperazin-1-yl)-4-oxo-4H-chromene-2-carboxylic acid hydrochloride (Reference Example 1) and 4-(4-methanesulfonyl-piperazin-1-yl)-phenylamine (Reference Example 12) as prepared in Example 1, yielding a yellow solid.

MS (M+H) m/z=526.

EXAMPLE 12

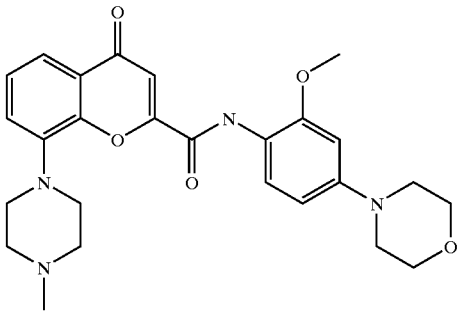

8-(4-Methyl-piperazin-1-yl)-4-oxo-4H-chromene-2-carboxylic acid (2-methoxy-4-morpholin-4-yl-phenyl)-amide 8-(4-Methyl-piperazin-1-yl)-4-oxo-4H-chromene-2-carboxylic acid hydrochloride (Reference Example 1) (9.10 g, 0.35 mmol), HOBt (0.10 g, 0.7 mmol), TBTU (0.225 g, 0.7 mmol), 4-(dimethylamino)pyridine (0.01 g, catalytic amount), triethylamine (0.15 mL, 1.04 mmol), and commercially available 2-methoxy-4-morpholin-4-yl-phenylamine (SALOR) (0.08 g, 0.38 mmol) were dissolved in dimethylformamide (2.5 mL) and stirred at room temperature overnight. Ethyl acetate (150 mL) was added and the resulting mixture was washed with water (3×50 mL), dried ($Na_2SO_4$), filtered, concentrated under vacuum and triturated with ether to yield a yellow solid (85 mg, 54%). LCMS: m/z=480.3.

EXAMPLE 13

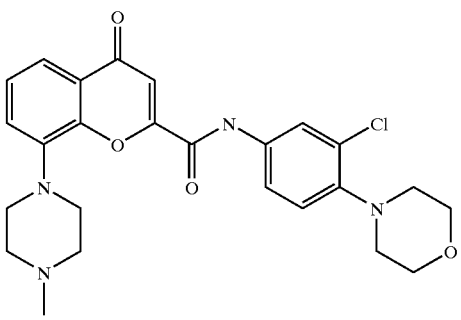

8-(4-Methyl-piperazin-1-yl)-4-oxo-4H-chromene-2-carboxylic acid (3-chloro-4-morpholin-4-yl-phenyl)-amide This compound was prepared from 8-(4-Methyl-piperazin-1-yl)-4-oxo-4H-chromene-2-carboxylic acid hydrochloride (Reference Example 1) and commercially available 3-chloro-4-morpholin-4-yl-phenylamine (Maybridge) as prepared in Example 12, yielding a yellow solid. (110 mg=73%), LCMS-m/z=483.5.

EXAMPLE 14

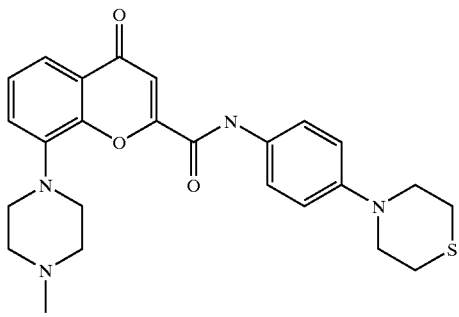

8-(4-Methyl-piperazin-1-yl)-4-oxo-4H-chromene-2-carboxylic acid (4-thiomorpholin-4-yl-phenyl)-amide This compound was prepared from 8-(4-Methyl-piperazin-1-yl)-4-oxo-4H-chromene-2-carboxylic acid hydrochloride (Reference Example 1) and 4-thiomorpholin-4-yl-phenylamine (Reference Example 13) as prepared in Example 12, yielding a yellow solid. (55 g=38%), LCMS-m/z=465.5.

EXAMPLE 15

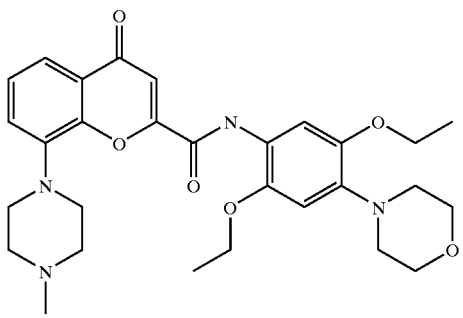

8-(4-Methylpiperazin-1-yl)-4-oxo-4H-chromene-2-carboxylic acid (2,5-diethoxy-4-morpholin-4-yl-phenyl)-amide This compound was prepared from 8-(4-Methyl-piperazin-1-yl)-4-oxo-4H-chromene-2-carboxylic acid hydrochloride (Reference Example 1) and commercially available 2,5-diethoxy-4-morpholin-4-yl-phenylamine (Aldrich) as prepared in Example 12, yielding a yellow solid. (80 mg=50%), LCMS-m/z=537.6.

EXAMPLE 16

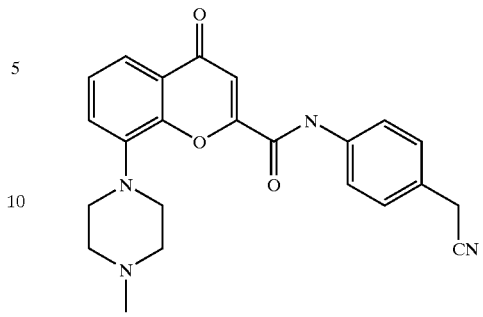

8-(4-Methyl-piperazin-1-yl)-4-oxo-4H-chromene-2-carboxylic acid (4-cyanomethyl-phenyl)-amide This compound was prepared from 8-(4-Methyl-piperazin-1-yl)-4-oxo-4H-chromene-2-carboxylic acid hydrochloride (Reference Example 1) and commercially available (4-amino-phenyl)-acetonitrile (Aldrich) as prepared in Example 12, yielding a yellow solid. (65 mg=54%), LCMS-m/z=403.5.

EXAMPLE 17

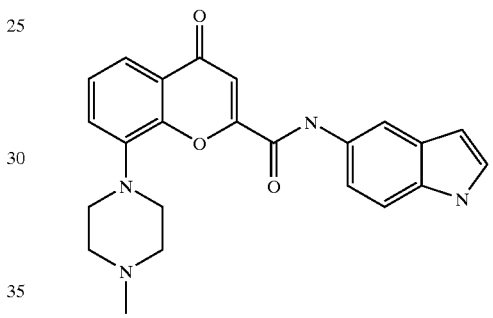

8-(4-Methyl-piperazin-1-yl)-4-oxo-4H-chromene-2-carboxylic acid (1H-indol-5-yl)-amide This compound was prepared from 8-(4-Methyl-piperazin-1-yl)-4-oxo-4H-chromene-2-carboxylic acid hydrochloride (Reference Example 1) and commercially available 1H-indol-5-ylamine (Aldrich) as prepared in Example 12, yielding a yellow solid. (35 mg=29%), LCMS-m/z=401.6.

EXAMPLE 18

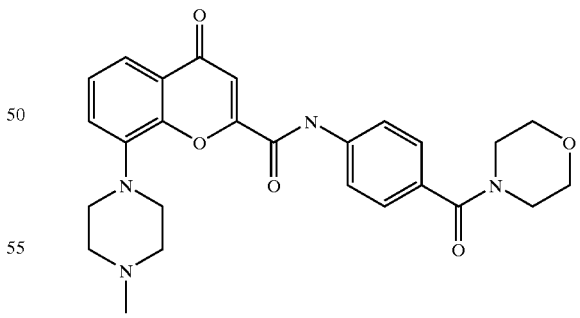

8-(4-Methyl-piperazin-1-yl)-4-oxo-4H-chromene-2-carboxylic acid [4-(1-morpholin-4-yl-methanoyl)-phenyl]-amide This compound was prepared from 8-(4-Methyl-piperazin-1-yl)-4-oxo-4H-chromene-2-carboxylic acid hydrochloride (Reference Example 1) and 1-(4-amino-phenyl)-1-morpholin-4-yl-methanone (Reference Example 14) as prepared in Example 12, yielding a yellow solid. (21 mg=15%), LCMS-m/z=477.6.

EXAMPLE 19

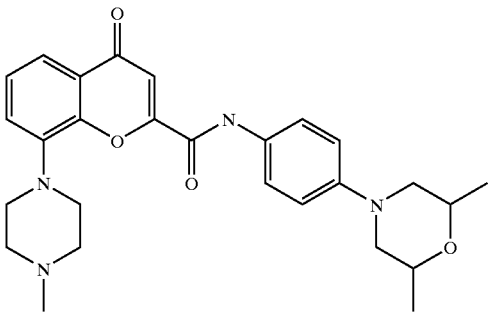

8-(4-Methyl-piperazin-1-yl)-4-oxo-4H-chromene-2-carboxylic acid [4-(2,6-dimethyl-morpholin-4-yl)-phenyl]-amide This compound was prepared from 8-(4-Methyl-piperazin-1-yl)-4-oxo-4H-chromene-2-carboxylic acid hydrochloride (Reference Example 1) and commercially available 4-(2,6-dimethyl-morpholin-4-yl)-phenylamine (Maybridge) as prepared in Example 1.2, yielding a yellow solid. (60 mg=42%), LCMS-m/z=477.6.

EXAMPLE 20

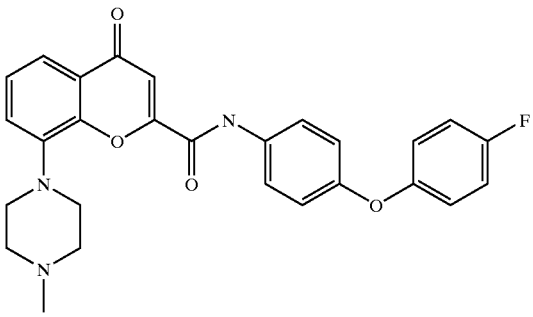

8-(4-Methyl-piperazin-1-yl)-4-oxo-4H-chromene-2-carboxylic acid [4-(4-fluoro-phenoxy)-phenyl]-amide This compound was prepared from 8-(4-Methyl-piperazin-1-yl)-4-oxo-4H-chromene-2-carboxylic acid hydrochloride (Reference Example 1) and commercially available 4-(4-fluoro-phenoxy)-phenylamine (Maybridge) as prepared in Example 12, yielding a yellow solid. (110 mg=77%), LCMS-m/z=475.6.

EXAMPLE 21

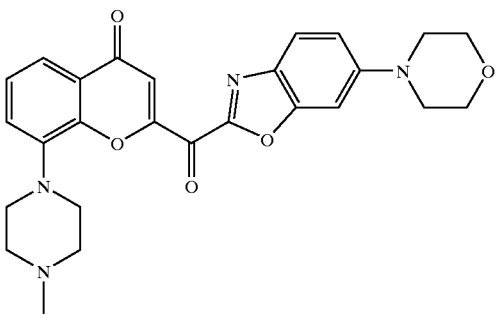

8-(4-Methyl-piperazin-1-yl)-2-(6-morpholin-4-yl-benzooxazol-2-yl)-chromen-4-one 8-(4-Methyl-piperazin-1-yl)-4-oxo-4H-chromene-2-carboxylic acid hydrochloride (Reference Example 1) (0.532 g, 1.85 mmol) was placed in a 25 mL 3-neck flask under nitrogen and treated with PPA (6 g). The mixture was then treated with the prepared intermediate 4-amino-3-hydroxyphenylmorpholine (0.43 g of ~85% pure, ~2 mmol). The mixture was stirred and heated in an oil bath to 205° C. for 3 hours to give a dark liquid. The mixture was cooled to room temperature and treated with 10 mL of water to give a dark solution. The solution was slowly neutralized with 1N aqueous sodium hydroxide to pH~7 as a solid formed. The solid was collected, washed several times with water, air dried, and vacuum dried at room temperature to give 0.65 g of a black solid. TLC (10% MeOH in $CHCl_3$ on $SiO_2$) showed 2 major components at $R_f$~0.5 and several lower $R_f$ minor components. The solid was triturated with saturated aqueous sodium bicarbonate at room temperature. It was filtered off, washed several times with water, and air dried to give 0.65 g of a dark gray solid. TLC showed the same components seen previously. Mass spectral analysis showed m/e=447 by positive ion CI and m/e=446 by negative ion CI. The solid was dissolved in 2% methanol in chloroform and it was chromatographed on a Megabond Elute silica gel column (10 g of $SiO_2$) using 2% methanol in chloroform. The slightly faster $R_f$ yellow component was concentrated to give 0.0188 g of a yellow solid. CI mass spectral analysis showed m/e=447 as the base peak by positive ion CI. The solid was recrystallized in methanol to give 0.0178 g of a yellow solid with a melting point of 158.1–158.8° C. Proton NMR ($CDCl_3$) and CI mass spectral analyses were consistent for the desired product (m/z=447 base peak by positive ion CI and m/z=446 base peak by negative ion CI).

EXAMPLE 22

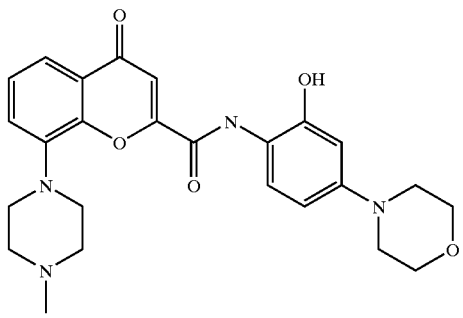

8-(4-Methyl-piperazin-1-yl)-4-oxo-4H-chromene-2-carboxylic acid (2-hydroxy-4-morpholin-4-yl-phenyl)-amide 8-(4-methyl-piperazin-1-yl)-4-oxo-4H-chromene-2-carboxylic acid hydrochloride (Reference Example 1) (0.3768 g, 1.16 mmol) was placed in a 100 mL 3-neck flask under nitrogen and it was dissolved in 20 mL of DMF. The solution was treated with triethylamine (0.49 mL, 3.5 mmol) followed by HOBT hydrate (0.36 g, 2.3 mmol) followed by TBTU (0.74 g, 2.3 mmol) and then followed by DMAP (0.020 g). The mixture was stirred for 10 minutes and then it was treated with 4-amino-3-hydroxyphenylmorpholine (Reference example 21) (0.228 g, 1.17 mmol). The mixture was stirred for 15 minutes and then it was treated with triethylamine (0.17 mL, 1.2 mmol). The mixture was stirred at room temperature for 42 hours and then it was added to a solution of 50 mL of saturated aqueous sodium bicarbonate and 50 mL of water. The mixture was extracted 4 times with ethyl acetate, dried over magnesium sulfate, filtered, and concentrated to give 0.834 gram of a purple oil. The oil was dissolved in 2 percent methanol in chloroform and it was placed on a silica gel column (5.5 cm diameter by 10.5 cm.long),and eluted with 2 percent methanol in chloroform followed by 5 percent methanol in chloroform. The yellow fraction was concentrated to give 0.2031 gram of an orange-yellow solid. The solid was dissolved in methanol, filtered through a medium sintered glass funnel, and concentrated to a few ml volume as a solid formed. The solid was filtered off, washed with methanol, and air dried to give 0.1613 gram of a tan solid with MP of 248.4–249.6° C. Proton COSY NMR and CI mass spectral analyses were consistent for the desired product (m/z=465 by positive ion CI and m/z=463 by negative ion CI).

EXAMPLE 23

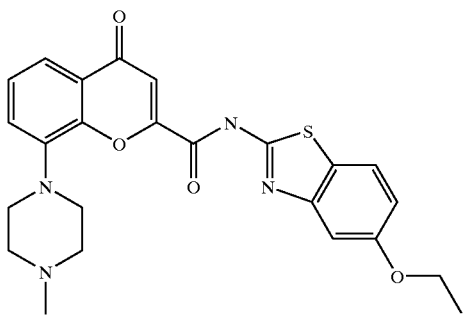

8-(4-Methyl-piperazin-1-yl)-4-oxo-4H-chromene-2-carboxylic acid (5-ethoxy-benzothiazol-2-yl)-amide This compound was prepared from 8-(4-Methyl-piperazin-1-yl)-4-oxo-4H-chromene-2-carboxylic acid hydrochloride (Reference Example 1) and commercially available 5-ethoxy-benzothiazol-2-ylamine (SALOR) as prepared in Example 12, yielding a yellow solid. (55 mg=39%), LCMS-m/z=465.3.

EXAMPLE 24

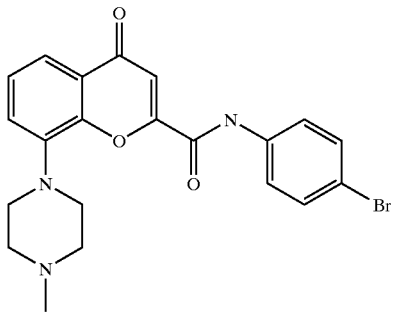

8-(4-Methyl-piperazin-1-yl)-4-oxo-4H-chromene-2-carboxylic acid (4-bromo-phenyl)-amide This compound was prepared from 8-(4-Methyl-piperazin-1-yl)-4-oxo-4H-chromene-2-carboxylic acid hydrochloride (Reference Example 1) and commercially available 4-bromo-phenylamine (Aldrich) as prepared in Example 12, yielding a yellow solid. (1.0 g=75%), LCMS-m/z=442.4.

EXAMPLE 25

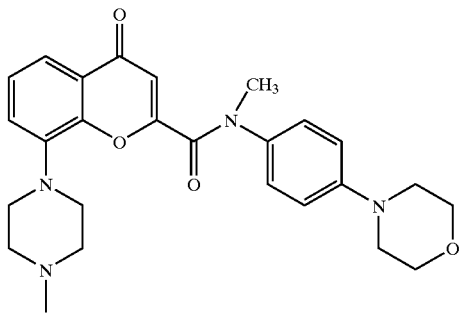

8-(4-Methylpiperazin-1-yl)-4-oxo-4H-chromene-2-carboxylic acid methyl-(4-morpholin-4-yl-phenyl) amide 8-(4-Methyl-piperazin-1-yl)-4-oxo-4H-chromene-2-carboxylic acid (4-morpholin-4-yl-phenyl)-amide (Example 1) (0.1046 g, 0.2332 mmol) was placed in a 10 mL single neck round flask under nitrogen. The solid was dissolved in 2.8 mL of anhydrous DMF. The yellow solution was stirred at room temperature and treated with one portion of sodium hydride (0.011 g of 95%, 0.44 mmol). The mixture evolved gas and became a red solution. It was stirred under nitrogen for 20 minutes and then it was treated with iodomethane (0.015 mL, 0.033 g, 0.233 mmol). The mixture was sealed and stirred at room temperature for 18 hours.

The reaction mixture was concentrated to remove most of the DMF (35 C bath @ 0.5 mm) to give a dark semisolid. It was treated with a few drops of water followed by 10 mL of ethyl acetate. The mixture was dried over magnesium sulfate, filtered, and concentrated to give 0.0564 gram of a yellow glass. The glass was triturated with diethyl ether, filtered off, and dried under high vacuum to give 0.0302 g of a tan solid with MP of 245.0–246.8 C. Proton NMR and CI mass spectral analyses were consistent for the desired product (m/z=463 by positive ion CI).

EXAMPLE 26

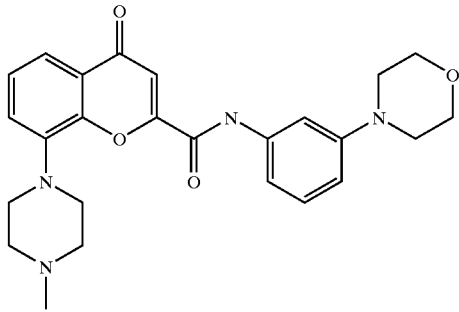

8-(4-Methyl-piperazin-1-yl)-4-oxo-4H-chromene-2-carboxylic acid (3-morpholin-4-yl-phenyl)-amide This compound was prepared from 8-(4-Methyl-piperazin-1-yl)-4-oxo-4H-chromene-2-carboxylic acid hydrochloride (Reference Example 1) and 3-morpholin-4-yl-phenylamine (Reference Example 18) as prepared in Example 12, yielding a yellow solid. (120 mg=86%), LCMS-m/z=449.5.

EXAMPLE 27

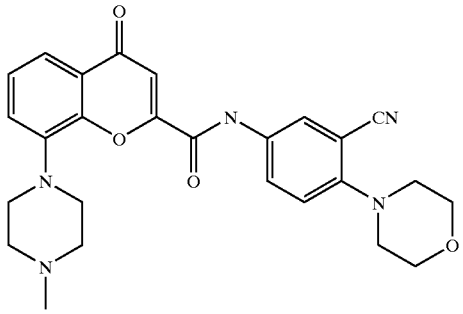

8-(4-Methyl-piperazin-1-yl)-4-oxo-4H-chromene-2-carboxylic acid (3-cyano-4-morpholin-4-yl-phenyl)-amide This compound was prepared from 8-(4-Methyl-piperazin-1-yl)-4-oxo-4H-chromene-2-carboxylic acid hydrochloride (Reference Example 1) and 5-amino-2-morpholin-4-yl-benzonitrile (Reference Example 15) as prepared in Example 12, yielding a yellow solid. (120 mg=82%), LCMS-m/z=474.5.

EXAMPLE 28

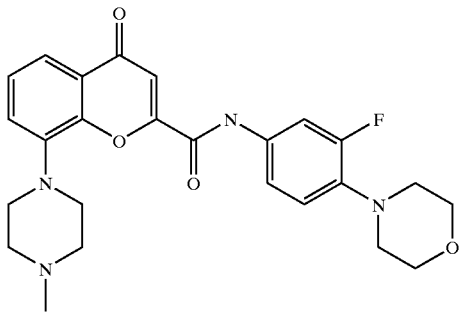

8-(4-Methyl-piperazin-1-yl)-4-oxo-4H-chromene-2-carboxylic acid (3-fluoro-4-morpholin-4-yl-phenyl)-amide This compound was prepared from 8-(4-Methyl-piperazin-1-yl)-4-oxo-4H-chromene-2-carboxylic acid hydrochloride (Reference Example 1) and 3-fluoro-4-morpholin-4-yl-phenylamine (Reference Example 16) as prepared in example 12, yielding a yellow solid. (120 mg=83%), LCMS-m/z=467.6.

EXAMPLE 29

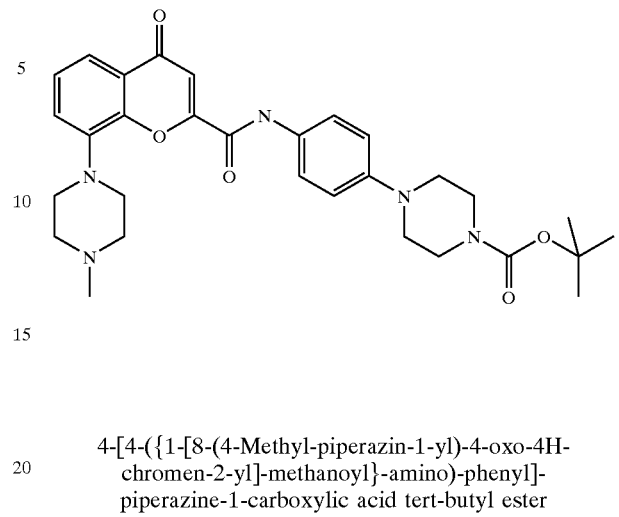

4-[4-({1-[8-(4-Methyl-piperazin-1-yl)-4-oxo-4H-chromen-2-yl]-methanoyl}-amino)-phenyl]-piperazine-1-carboxylic acid tert-butyl ester This compound was prepared from 8-(4-Methyl-piperazin-1-yl)-4-oxo-4H-chromene-2-carboxylic acid hydrochloride (Reference Example 1) and 4-(4-amino-phenyl)-piperazine-1-carboxylic acid tert-butyl ester (Reference Example 17) as prepared in example 12, yielding a yellow solid. (260 mg=53%), LCMS-m/z=548.6.

EXAMPLE 30

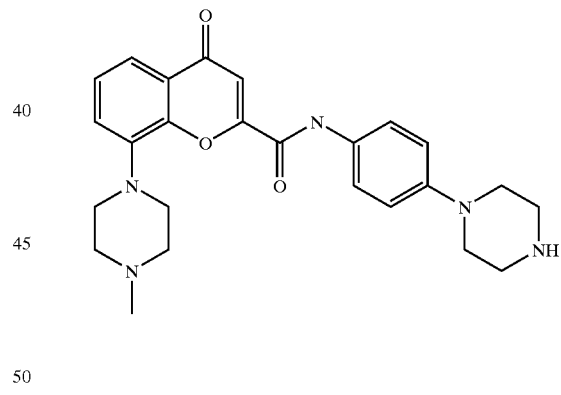

8-(4-Methyl-piperazin-1-yl)-4-oxo-4H-chromene-2-carboxylic acid (4-piperazin-1-yl-phenyl)-amide 4-[4-({1-[8-(4-Methyl-piperazin-1-yl)-4-oxo-4H-chromen-2-yl]-methanoyl}-amino)-phenyl]-piperazine-1-carboxylic acid tert-butyl ester (Example 29) (160 mg, 0.3 mmol) was dissolved ethyl acetate (20 mL) and cooled to 0° C. HCl gas was bubbled in slowly for 2 minutes. A solid began to precipitate. Methanol (3–4 mL) was added to dissolve this solid and HCl gas was bubbled in for another 2 minutes. The mixture was concentrated under reduced pressure and triturated with ether and dried under vacuum to yield a tan solid (100 mg, 76%). LCMS/m/z=448.6.

EXAMPLE 31

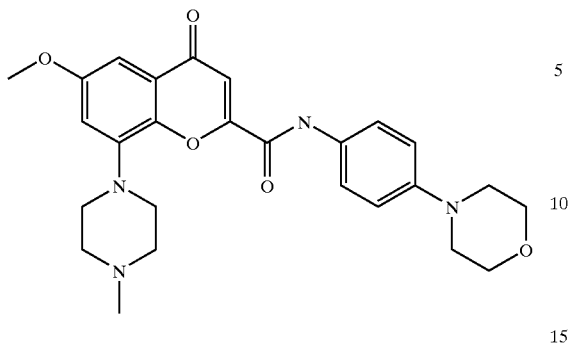

6-Methoxy-8-(4-methyl-piperazin-1-yl)-4-oxo-4H-chromene-2-carboxylic acid (4-morpholin-4-yl-phenyl)-amide 6-Methoxy-8-(4-Methyl-piperazin-1-yl)-4-oxo-4H-chromene-2-carboxylic acid hydrochloride (Reference Example 2) (3.0 g, 8.5 mmol), TBTU (5.5 g, 17 mmol), 1-hydroxybenztriazole (2.6 g, 17 mmol), 4-dimethylaminopyridine (0.05 g, catalytic) and commercially available 4-morpholin-4-yl-aniline (1.66 g, 9.3 mmol) were dissolved in dimethylformamide (100 mL). Triethylamine (3.5 mL, 25 mmol was added and this mixture stirred at room temperature for 17 hours. The reaction mixture was concentrated under vacuum and the residue was partitioned between chloroform (400 mL) and saturated aqueous sodium bicarbonate (50 mL). The organic'layer was separated, dried ($Na_2SO_4$), vacuum-filtered and concentrated under vacuum. The residue was purified by chromatography on silica eluted with 2–5% methanol in chloroform and then triturated with ether to yield a yellow powder. (1.6 g=39%) LCMS-m/z=479.5 mp=234–236° C.

EXAMPLE 32

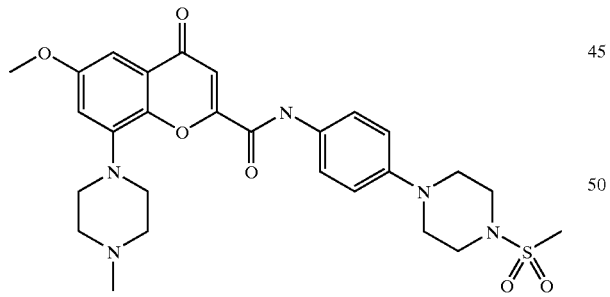

6-Methoxy-8-(4-methyl-piperazin-1-yl)-4-oxo-4H-chromene-2-carboxylic acid [4-(4-methanesulfonyl-piperazin-1-yl)-phenyl]-amide This compound was prepared from 6-Methoxy-8-(4-methyl-piperazin-1-yl)-4-oxo-4H-chromene-2-carboxylic acid hydrochloride (Reference Example 2) and 4-(4-methanesulfonyl-piperazin-1-yl)-phenylamine (Reference Example 12) as prepared in example 1, yielding a yellow solid. GC/MS (EI, M+) m/z=556.

EXAMPLE 33

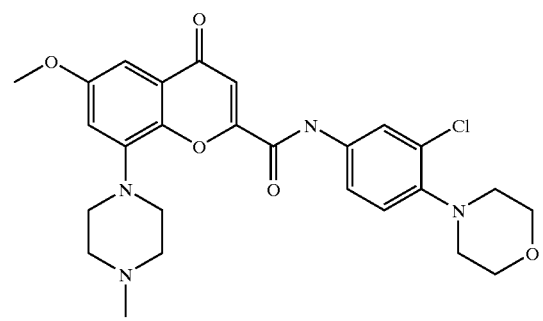

6-Methoxy-8-(4-Methyl-piperazin-1-yl)-4-oxo-4H-chromene-2-carboxylic acid (3-chloro-4-morpholin-4-yl-phenyl)-amide This compound was prepared from 6-Methoxy-8-(4-methyl-piperazin-1-yl)-4-oxo-4H-chromene-2-carboxylic acid hydrochloride (Reference Example 2) and commercially available 3-chloro-4-morpholin-4-yl-phenylamine (Maybridge) as prepared in Example 12, yielding a yellow solid. (45 mg=31%) LCMS-m/z=513.5.

EXAMPLE 34

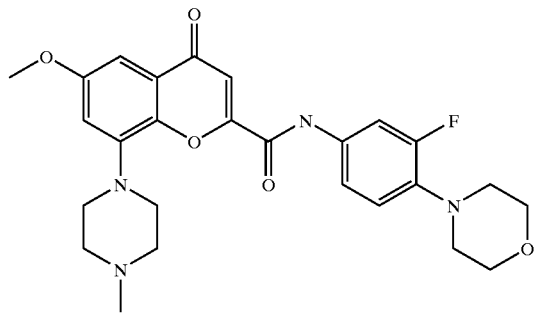

6-Methoxy-8-(4-methyl-piperazin-1-yl)-4-oxo-4H-chromene-2-carboxylic acid (3-fluoro-4-morpholin-4-yl-phenyl)-amide This compound was prepared from 6-methoxy-8-(4-Methyl-piperazin-1-yl)-4-oxo-4H-chromene-2-carboxylic acid hydrochloride (Reference Example 2) and 3-fluoro-4-morpholin-4-yl-phenylamine (Reference Example 16) as prepared in Example 12, yielding a yellow solid. (55 mg=61%), LCMS-m/z=497.5.

EXAMPLE 35

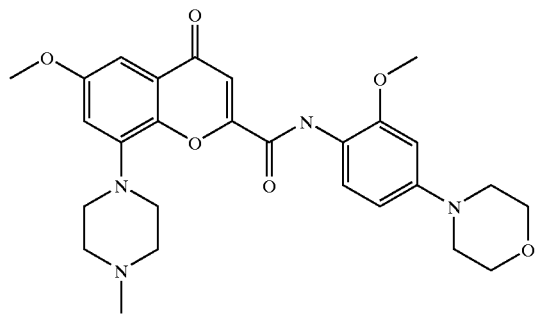

6-Methoxy-8-(4-methyl-piperazin-1-yl)-4-oxo-4H-chromene-2-carboxylic acid (2-methoxy-4-morpholin-4-yl-phenyl)-amide This compound was prepared from 6-methoxy-8-(4-Methyl-piperazin-1-yl)-4-oxo-4H-chromene-2-carboxylic acid hydrochloride (Reference Example 2) and commercially available 2-methoxy-4-morpholin-4-yl-phenylamine (SALOR) as prepared in Example 12, yielding a yellow solid. (55 mg=38%), LCMS-m/z=510.5.

EXAMPLE 36

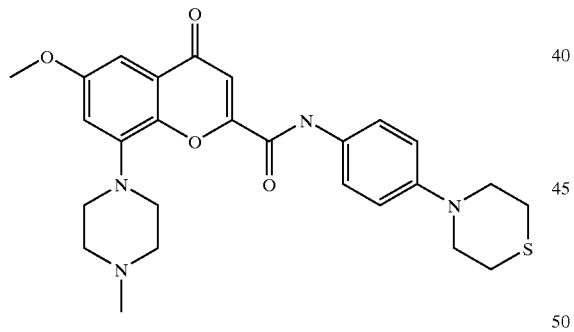

6-Methoxy-8-(4-methyl-piperazin-1-yl)-4-oxo-4H-chromene-2-carboxylic acid (4-thiomorpholin-4-yl-phenyl)-amide This compound was prepared from 6-methoxy-8-(4-Methyl-piperazin-1-yl)-4-oxo-4H-chromene-2-carboxylic acid hydrochloride (Reference Example 2) and 4-thiomorpholin-4-yl-phenylamine (Reference Example 13) as prepared in Example 12, yielding a yellow solid. (99 mg=71%), LCMS-m/z=495.5.

EXAMPLE 37

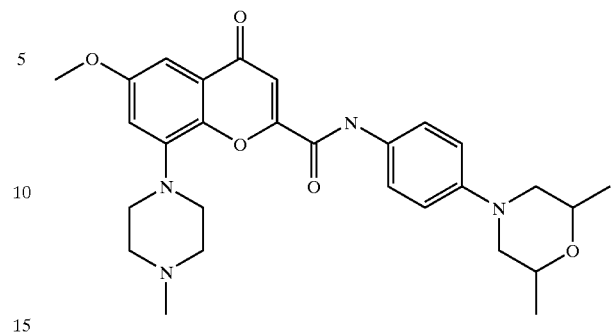

6-Methoxy-8-(4-methyl-piperazin-1-yl)-4-oxo-4H-chromene-2-carboxylic acid [4-(2,6-dimethyl-morpholin-4-yl)-phenyl]-amide This compound was prepared from 6-methoxy-8-(4-Methyl-piperazin-1-yl)-4-oxo-4H-chromene-2-carboxylic acid hydrochloride (Reference Example 2) and commercially available 4-(2,6-dimethyl-morpholin-4-yl)-phenylamine (Maybridge) as prepared in Example 12, yielding a yellow solid. (70 mg=49%), LCMS-m/z=507.5.

EXAMPLE 38

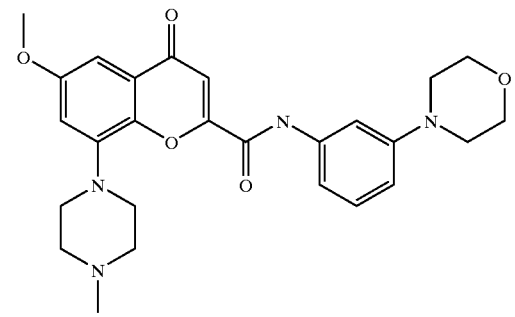

6-Methoxy-8-(4-methyl-piperazin-1-yl)-4-oxo-4H-chromene-2-carboxylic acid (3-morpholin-4-yl-phenyl)-amide This compound was prepared from 6-methoxy-8-(4-Methyl-piperazin-1-yl)-4-oxo-4H-chromene-2-carboxylic acid hydrochloride (Reference Example 2) and 3-morpholin-4-yl-phenylamine (Reference Example 18) as prepared in Example 12, yielding a yellow solid. (80 mg=60%), LCMS-m/z=479.5.

EXAMPLE 39

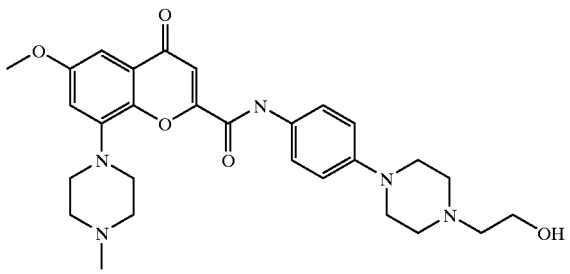

6-Methoxy-8-(4-methyl-piperazin-1-yl)-4-oxo-4H-chromene-2-carboxylic acid {4-[4-(2-hydroxy-ethyl)piperazin-1-yl]-phenyl}-amide This compound was prepared from 6-methoxy-8-(4-Methyl-piperazin-1-yl)-4-oxo-4H-chromene-2-carboxylic acid hydrochloride (Reference Example 2) and 2-[4-(4-amino-phenyl)-piperazin-1-yl]-ethanol (Reference Example 19) as prepared in Example 12, yielding a yellow solid. (80 mg=60%). mp=211.5–212.2 (dec.), MS-base peak at m/z=492 by positive ion and m/z=490 by negative ion CI.

EXAMPLE 40

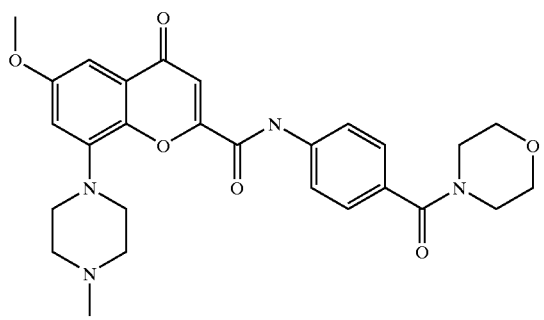

6-Methoxy-8-(4-methyl-piperazin-1-yl)-4-oxo-4H-chromene-2-carboxylic acid [4-(1-morpholinyl-methanoyl)-phenyl]-amide This compound was prepared from 6-methoxy-8-(4-Methyl-piperazin-1-yl)-4-oxo-4H-chromene-2-carboxylic acid hydrochloride (Reference Example 2) and 1-(4-amino-phenyl)-1-morpholin-4-yl-methanone (Reference Example 14) as prepared in Example 12, yielding a yellow solid. (170 mg=80%), LCMS-m/z=507.5.

EXAMPLE 41

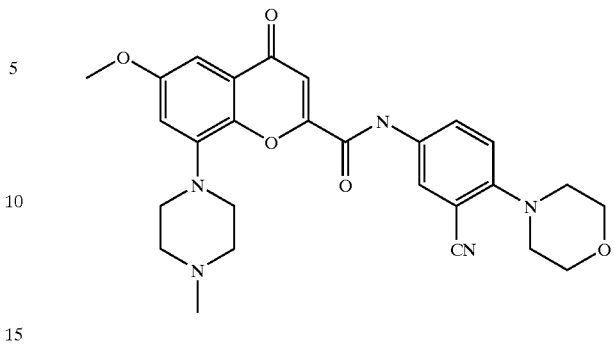

6-Methoxy-8-(4-methyl-piperazin-1-yl)-4-oxo-4H-chromene-2-carboxylic acid (3-cyano-4-morpholin-4-yl-phenyl)-amide This compound was prepared from 6-methoxy-8-(4-Methyl-piperazin-1-yl)-4-oxo-4H-chromene-2-carboxylic acid hydrochloride (Reference Example 2) and 5-amino-2-morpholin-4-yl-benzonitrile (Reference Example 15) as prepared in Example 12, yielding a yellow solid. (120 mg=57%), LCMS-m/z=504.5.

EXAMPLE 42

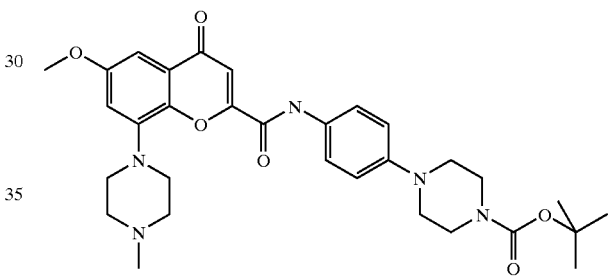

4-[({1-[6-Methoxy-8-(4-methyl-piperazin-1-yl)-4-oxo-4H-chromen-2-yl]-methanoyl}-amino)-phenyl]-piperazine-1-carboxylic acid tert-butyl ester The 6-methoxy-8-(4-methyl-piperazin-1-yl)-4-oxo-4H-chromene-2-carboxylic acid hydrochloride (Reference Example 2) (1.04 g, 2.93 mmol) was placed in a 250 ml 3-neck flask under nitrogen and it was dissolved in 50 ml of DMF. The solution was treated with triethylamine (1.22 mL, 8.79 mmol) followed by HOBT hydrate (0.90 g, 5.9 mmol) followed by TBTU (1.88 g, 5.9 mmol) and then followed by DMAP (0.056 g, 0.46 mmol). The mixture was stirred for 10 minutes and then it was treated with 4-(4-Amino-phenyl)-piperazine-1-carboxylic acid tert-butyl ester (Reference Example 17) (0.81 g, 2.9 mmol). The mixture was stirred for 15 minutes and then it was treated with triethylamine (0.41 mL, 2.9 mmol). The mixture was stirred at room temperature for 18 hours and then it was concentrated (1 mm Hg pressure, 45 C bath) to give a dark liquid. The concentrate was treated with 80 mL of saturated aqueous sodium bicarbonate and extracted with ethyl acetate forming a suspended yellow solid in the organic layer. The solid was filtered off, washed with diethyl ether, washed with water, and vacuum dried (0.1 mm Hg pressure @ 25 C) to give 0.36 gram of a yellow solid, M.P.=232.3–232.8 C.

Proton NMR and CI mass spectral analyses were consistent for the desired product (m/e=578 by positive ion CI and m/e=576 by negative ion CI).

The aqueous layer was extracted twice with ethyl acetate, dried over magnesium sulfate, filtered, and concentrated to give 1.35 gram of a dark semisolid. It was triturated with diethyl ether and allowed to stand at room temperature as a solid formed. The solid was filtered off, washed with diethyl ether, and vacuum dried at room temperature to give 0.4816 gram of a yellow solid. CI mass spectral analyses was consistent for the desired product (M/Z=578 BY positive ion CI AND M/Z=576 by negative ion CI).

EXAMPLE 43

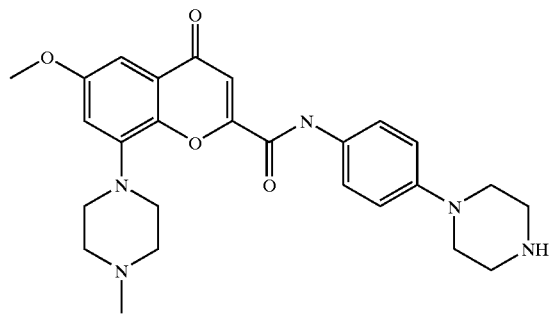

6-Methoxy-8-(4-methyl-piperazin-1-yl)-4-oxo-4H-chromene-2-carboxylic acid (4-piperazin-1-yl-phenyl)-amide The 4-[4-({1-[6-Methoxy-8-(4-methyl-piperazin-1-yl)-4-oxo-4H-chromen-2-yl]-methanoyl}-amino)-phenyl]-piperazine-1-carboxylic acid tert-butyl ester (Example 42) (0.792 gram, 1.37 mmol) was placed in a 50 ml round flask under nitrogen and it was dissolved in 15 ml of methylene chloride. The solution was treated with 15 ml of trifluoroacetic acid (195 mmol) to give a dark solution and it was stirred at room temperature for 18 hours. It was concentrated to give a brown foam. The foam was treated with 30 ml of saturated aqueous sodium bicarbonate and it was stirred at room temperature as a yellow solid formed. The solid was filtered off, washed several times with water, air dried and dried under high vacuum (0.1 mm Hg pressure) to give 0.493 gram of a yellow solid, M.P.=203.6–204.7 C.

Proton NMR and CI mass spectral analyses were consistent for the desired product (m/z=478 by positive ion CI and m/z=476 by negative ion CI).

EXAMPLES 44–54

The following examples were prepared in parallel by acylation of 6-methoxy-8-(4-methyl-piperazin-1-yl)-4-oxo-4H-chromene-2-carboxylic acid (4-piperazin-1-yl-phenyl)-amide (Example 43) in an Argonaut Quest synthesizer.

The piperazine side chain was derivatized in parallel fashion using eleven different commercially available acylating and sulfonating reagents. The resins used were Argonaut Tech polystyrene amine resins. Each 5 ml Quest tube was charged with 0.010 gram (0.021 mmol) of the starting N—H piperazine and 3 ml of methylene chloride followed by 4 equivalents (0.08 mmol) of PS-DIEA resin (diisopropylbenzylamine PS resin) to scavenge HCl. Each tube was then treated with an acyl chloride, sulfonyl chloride, or isocyanate (2 equivalents of each) followed by a little more methylene chloride. The tubes were sealed under nitrogen, and stirred for 3 hours at room temperature. The mixtures were then opened and treated with about 4 equivalents (0.08 mmol) of PS-trisamine resin (primary amine PS resin) to scavenge any excess acylating or sulfonating reagent. The mixtures were sealed and stirred for 1.5 hours and then filtered directly into vials and concentrated to give the products. The products were characterized by HPLC mass spectral analysis and were found to be greater than 90% pure by HPLC. The compounds were submitted to the 5-HT1b binding assay for determination of 5-HT receptor binding affinities and selectivities.

EXAMPLE 44

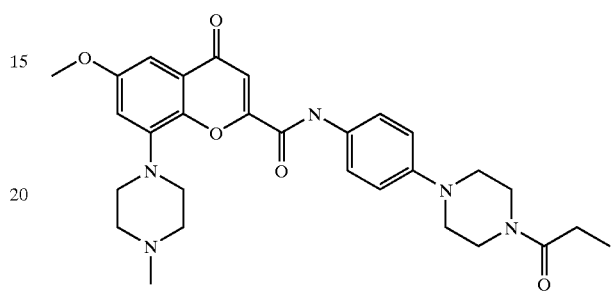

6-Methoxy-8-(4-methyl-piperazin-1-yl)-4-oxo-4H-chromene-2-carboxylic acid [4-(4-propionyl-piperazin-1-yl)-phenyl]-amide This compound was prepared from 6-methoxy-8-(4-methyl-piperazin-1-yl)-4-oxo-4H-chromene-2-carboxylic acid (4-piperazin-1-yl-phenyl)amide (Example 43) and commercially available propionyl chloride (Aldrich) via the parallel synthesis described above. MS-base peak at m/z=534 by positive ion CI.

EXAMPLE 45

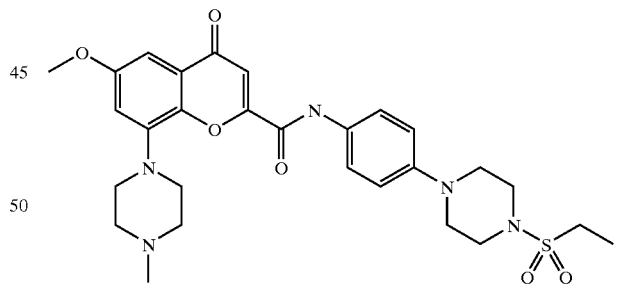

6-Methoxy-8-(4-methyl-piperazin-1-yl)-4-oxo-4H-chromene-2-carboxylic acid [4-(4-ethanesulfonyl-piperazin-1-yl)-phenyl]-amide This compound was prepared from 6-methoxy-8-(4-methyl-piperazin-1-yl)-4-oxo-4H-chromene-2-carboxylic acid (4-piperazin-1-yl-phenyl)-amide (Example 43) and commercially available ethanesulfonyl chloride (Aldrich) via the parallel synthesis described above. MS-base peak at m/z=570 by positive ion Cl, mp=232–234° C.

EXAMPLE 46

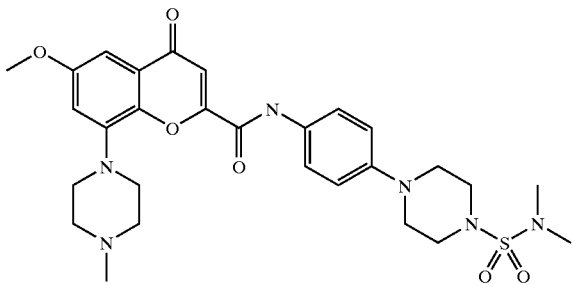

6-Methoxy-8-(4-methyl-piperazin-1-yl)-4-oxo-4H-chromene-2-carboxylic acid [4-(4-dimethyl sulfamoyl-piperazin-1-yl)-phenyl]-amide This compound was prepared from 6-methoxy-8-(4-methyl-piperazin-1-yl)-4-oxo-4H-chromene-2-carboxylic acid (4-piperazin-1-yl-phenyl)-amide (Example 43) and commercially available dimethylsulfamoyl chloride (Aldrich) via the parallel synthesis described above. MS-base peak at m/z=585 by positive ion CI.

EXAMPLE 47

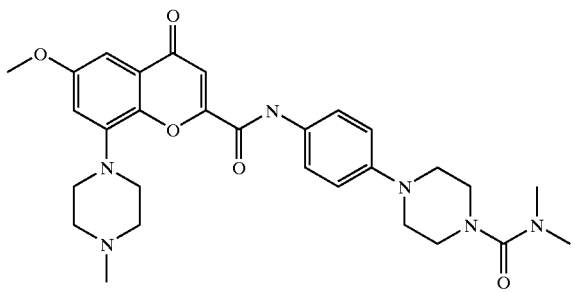

4-[4-({1-[6-Methoxy-8-(4-methyl-piperazin-1-yl)-4-oxo-4H-chromen-2-yl]-methanoyl}-amino)phenyl]-piperazine-1-carboxylic acid dimethylamide This compound was prepared from 6 methoxy-8-(4-methyl-piperazin-1-yl)-4-oxo-4H-chromene-2-carboxylic acid (4-piperazin-1-yl-phenyl)-amide (Example 43) and commercially available dimethylcarbamyl chloride (Aldrich) via the parallel synthesis described above. MS-base peak at m/z=549 by positive ion CI.

EXAMPLE 48

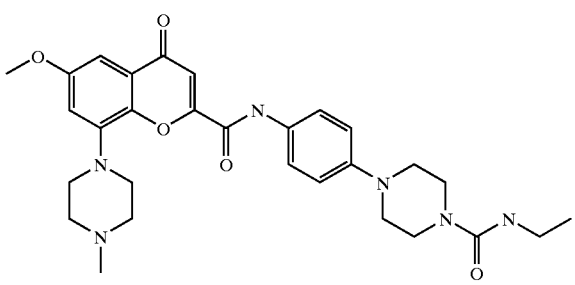

4-[4-({1-[6-Methoxy-8-(4-methyl-piperazin-1-yl)-4-oxo-4H-chromen-2-yl]-methanoyl}-amino)-phenyl]-piperazine-1-carboxylic acid ethylamide This compound was prepared from 6-methoxy-8-(4-methyl-piperazin-1-yl)-4-oxo-4H-chromene-2-carboxylic acid (4-piperazin-1-yl-phenyl)-amide (Example 43) and commercially available ethyl isocyanate (Aldrich) via the parallel synthesis described above.

MS-base peak at m/z=549 by positive ion CI.

EXAMPLE 49

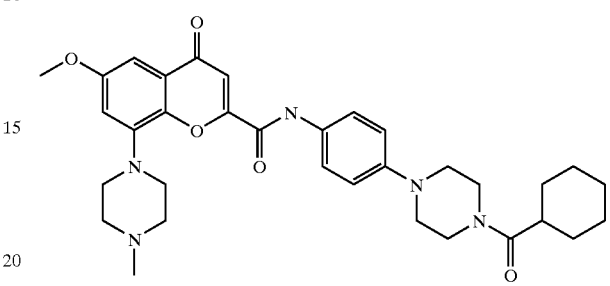

4-[4-({1-[6-Methoxy-8-(4-methyl-piperazin-1-yl)-4-oxo-4H-chromen-2-yl]-methanoyl}-amino)-phenyl]-piperazine-1-carboxylic acid cyclohexylamide This compound was prepared from 6-methoxy-8-(4-methyl-piperazin-1-yl)-4-oxo-4H-chromene-2-carboxylic acid (4-piperazin-1-yl-phenyl)-amide (Example 43) and commercially available cyclohexyl isocyanate (Aldrich) via the parallel synthesis described above. MS-base peak at m/z=603 by positive ion CI.

EXAMPLE 50

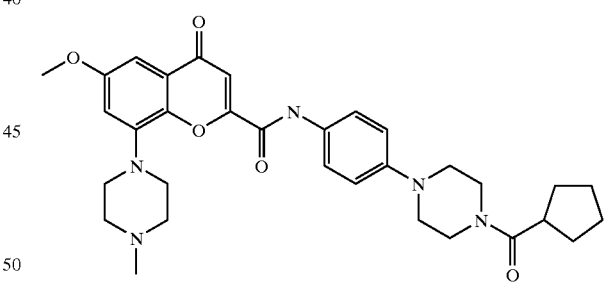

4-[4-({-[6-Methoxy-8-(4-methyl-piperazin-1-yl)-4-oxo-4H-chromen-2-yl]-methanoyl}-amino)-phenyl]-piperazine-1-carboxylic acid cyclopentylamide This compound was prepared from 6 methoxy-8-(4-methyl-piperazin-1-yl)-4-oxo-4H-chromene-2-carboxylic acid (4-piperazin-1-yl-phenyl)-amide (Example 43) and commercially available cyclopentanecarbonyl chloride (Aldrich) via the parallel synthesis described above.

MS-base peak at m/z=574 by positive ion CI.

EXAMPLE 51

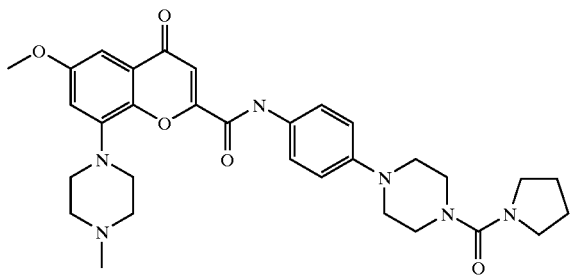

6-Methoxy-8-(4-methyl-piperazin-1-yl)-4-oxo-4H-chromene-2-carboxylic acid {4-[4-(1-pyrrolidin-1-yl-methanoyl)-piperazin-1-yl]-phenyl }-amide This compound was prepared from 6 methoxy-8-(4-methyl-piperazin-1-yl)-4-oxo-4H-chromene-2-carboxylic acid (4-piperazin-1-yl-phenyl)-amide (Example 43) and commercially available 1-pyrrolidinecarbonyl chloride (Aldrich) via the parallel synthesis described above. MS-base peak at m/z=575 by positive ion CI.

EXAMPLE 52

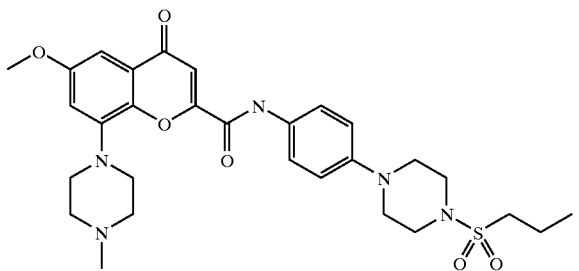

6-Methoxy-8-(4-methyl-piperazin-1-yl)-4-oxo-4H-chromene-2-carboxylic acid {4-[4-(propane-2-sulfonyl)-piperazin-1-yl]-phenyl}-amide This compound was prepared from 6-methoxy-8-(4-methyl-piperazin-1-yl)-4-oxo-4H-chromene-2-carboxylic acid (4-piperazin 1-yl-phenyl)-amide (Example 43) and commercially available isopropylsulfonylonyl chloride (Aldrich) via the parallel synthesis described above. MS-base peak at m/z=584 by positive ion CI.

EXAMPLE 53

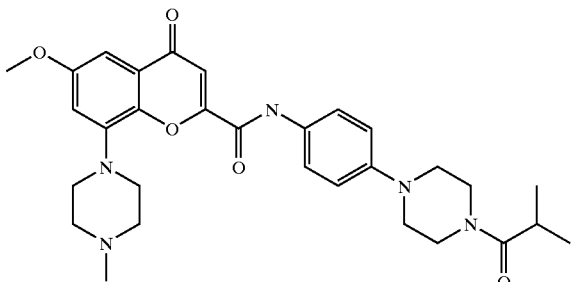

6-Methoxy-8-(4-methyl-piperazin-1-yl)-4-oxo-4H-chromene-2-carboxylic acid {4-[4-(methyl-propanoyl)-piperazin-1-yl]-phenyl }-amide This compound was prepared from 6-methoxy-8-(4-methyl-piperazin-1-yl)-4-oxo-4H-chromene-2-carboxylic acid (4-piperazin-1-yl-phenyl)-amide (Example 43) and commercially available isobutyryl chloride (Aldrich) via the parallel synthesis described above. MS-base peak at m/z= 548 by positive ion CI.

EXAMPLE 54

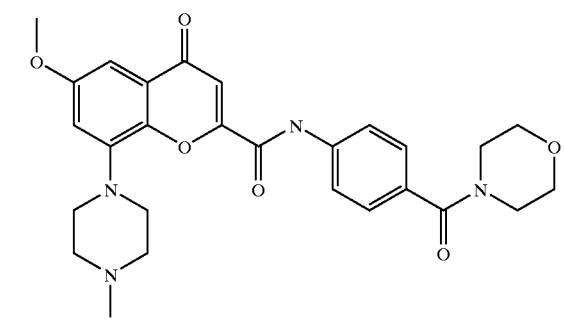

6-Methoxy-8-(4-methyl-piperazin-1-yl)-4-oxo-4H-chromene-2-carboxylic acid {4-[4-(1-morpholin-4-yl-methanoyl)-piperazin-1-yl]-phenyl}-amide This compound was prepared from 6-methoxy-8-(4-methyl-piperazin-1-yl)-4-oxo-4H-chromene-2-carboxylic acid (4-piperazin-1-yl-phenyl)-amide (Example 43) and commercially available morpholine-4-carbonyl chloride (Aldrich) via the parallel synthesis described above.

MS-base peak at m/z=591 by positive ion CI.

EXAMPLE 55

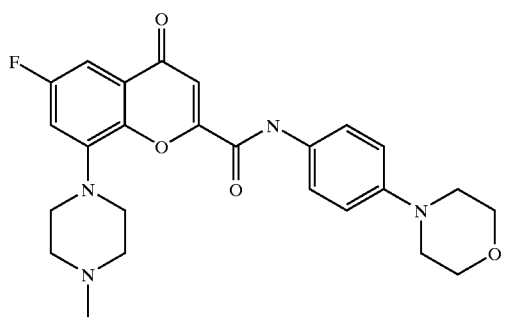

6-Fluoro-8-(4-methyl-piperazin-1-yl)-4-oxo-4H-chromene-2-carboxylic acid (4-morpholin-4-yl-phenyl)-amide This compound was prepared from 6-Fluoro-8-(4-methyl-piperazin-1-yl)-4-oxo-4H-chromene-2-carboxylic acid hydrochloride (Reference Example 3) and 4-morpholin-4-yl-phenylamine (Reference Example 20) as prepared in Example 1, yielding a yellow solid. MS (M+H) m/z=467.

EXAMPLE 56

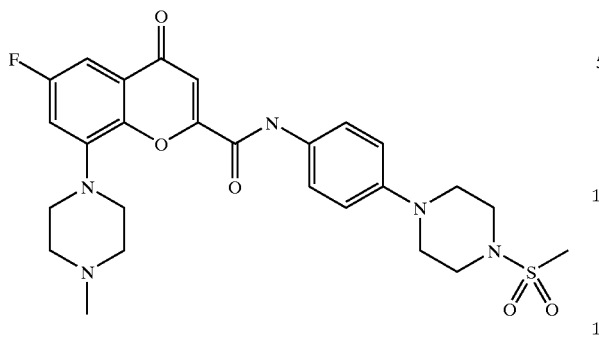

6-Fluoro-8-(4-methyl-piperazin-1-yl)-4-oxo-4H-chromene-2-carboxylic acid [4-(4-ethanesulfonyl-piperazin-1-yl)-phenyl]-amide This compound was prepared from 6-Fluoro-8-(4-methyl-piperazin-1-yl)-4-oxo-4H-chromene-2-carboxylic acid hydrochloride (Reference Example 3) and 4-(4-methanesulfonyl-piperazin-1-yl)-phenylamine (Reference Example 12) as prepared in Example 1, yielding a yellow solid. MS (M+H) m/z=544.

EXAMPLE 57

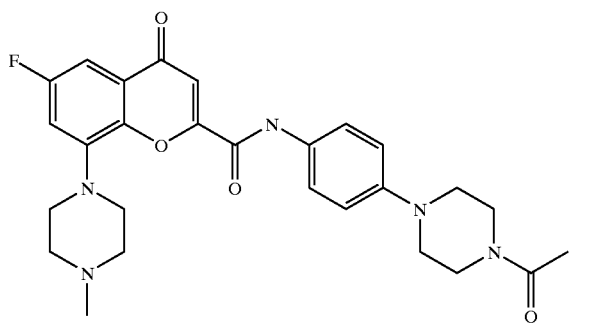

6-Fluoro-8-(4-methyl-piperazin-1-yl)-4-oxo-4H-chromene-2-carboxylic acid [4-(4-acetyl-piperazin-1-yl)-phenyl]-amide This compound was prepared from 6-Fluoro-8-(4-methyl-piperazin-1-yl)-4-oxo-4H-chromene-2-carboxylic acid hydrochloride (Reference Example 3) and 1-[4-(4-amino-phenyl)-piperazin-1-yl]-ethanone (Reference Example 11) as prepared in Example 1, yielding a yellow solid. MS (M+H) m/z=508.

EXAMPLE 58

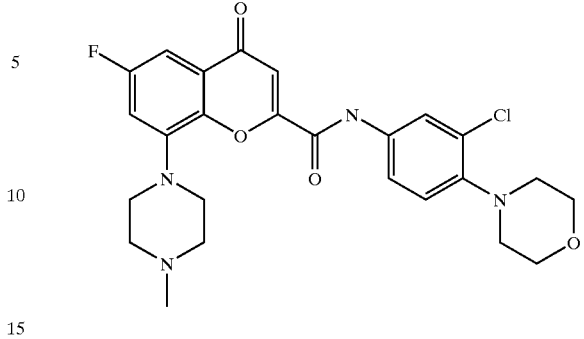

6-Fluoro-8-(4-methyl-piperazin-1-yl)-4-oxo-4H-chromene-2-carboxylic acid (3-chloro-4-morpholin-4-yl-phenyl)-amide 6-Fluoro-8-(4-methyl-piperazin-1-yl)-4-oxo-4H-chromene-2-carboxylic acid hydrochloride (Reference Example 3) (150 mg, 0.43 mmol), 1-hydroxybenzotriazole (140 mg, 0.9 mmol), O-(1H-Benzotriazol-1-yl)-N,N,N',N'-pentamethylene-uronium tetrafluoroborate (290 mg, 0.9 mmol), 4-(dimethylamino)pyridine (10 mg, catalytic), triethylamine (0.2 mL, 1.5 mmol), and commercially available 3-chloro-4-morpholin-4-yl-phenylamine (Maybridge) were dissolved in dimethylformamide (2.5 mL) and stirred at room temperature overnight. At 17 h, water (20 mL) was added and the resulting mixture was stirred for 15–30 min. The mixture was vacuum-filtered and the residue washed with water and air-dried to yield a yellow powder (220 mg=quantitative yield). LC/MS-m/z=501.5.

EXAMPLE 59

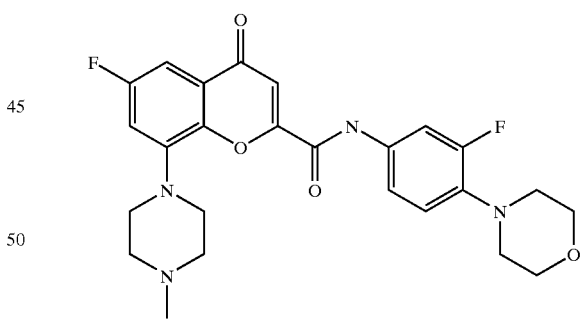

6-Fluoro-8-(4-methyl-piperazin-1-yl)-4-oxo-4H-chromene-2-carboxylic acid (3-fluoro-4-morpholin-4-yl-phenyl)-amide This compound was prepared from 6-Fluoro-8-(4-methyl-piperazin-1-yl)-4-oxo-4H-chromene-2-carboxylic acid hydrochloride (Reference Example 3) and 3-fluoro-4-morpholin-4-yl-phenylamine (Reference Example 16) as prepared in Example 58, yielding a yellow solid (210 mg=99%). LC/MS-m/z=485.5.

EXAMPLE 60

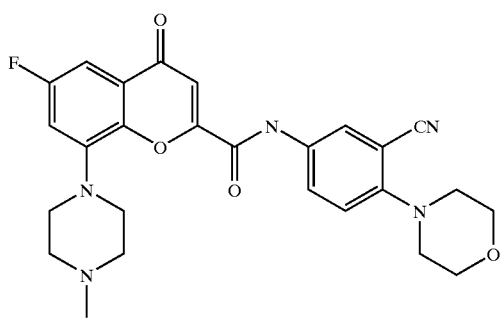

6-Fluoro-8-(4-methyl-piperazin-1-yl)-4-oxo-4H-chromene-2-carboxylic acid (3-cyano-4-morpholin-4-yl-phenyl)-amide This compound was prepared from 6-Fluoro-8-(4-methyl-piperazin-1-yl)-4-oxo-4H-chromene-2-carboxylic acid hydrochloride (Reference Example 3) and 5-amino-2-morpholin-4-yl-benzonitrile (Reference Example 15) as prepared in Example 58, yielding a yellow solid (210 mg=99%). LC/MS-m/z=492.5.

EXAMPLE 61

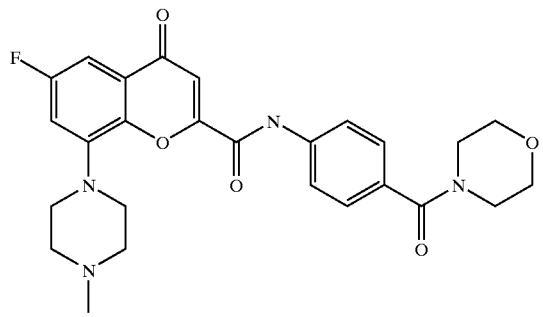

6-Fluoro-8-(4-methyl-piperazin-1-yl)-4-oxo-4H-chromene-2-carboxylic acid [4-(1-morpholin-4-yl-methanoyl)-phenyl]-amide This compound was prepared from 6-Fluoro-8-(4-methyl-piperazin-1-yl)-4-oxo-4H-chromene-2-carboxylic acid hydrochloride (Reference Example 3) and 1-(4-aminophenyl)-1-morpholin-4-yl-methanone (Reference Example 14) as prepared in Example 58, yielding a yellow solid (220 mg=quantitative yield). LC/MS-m/z=495.5.

EXAMPLE 62

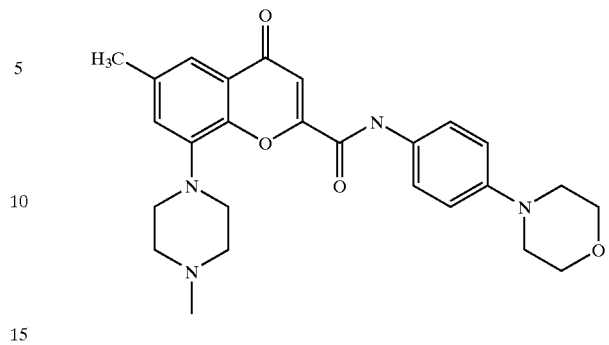

6-Methyl-8-(4-methyl-piperazin-1-yl)-4-oxo-4H-chromene-2-carboxylic acid (4-morpholin-4-yl-phenyl)-amide This compound was prepared from 6-Methyl-8-(4-methyl-piperazin-1-yl)-4-oxo-4H-chromene-2-carboxylic acid hydrochloride (Reference Example 4) and 4-morpholin-4-yl-phenylamine (Reference Example 20) as prepared in Example 1, yielding a yellow solid.

LCMS-m/z=463.6.

EXAMPLE 63

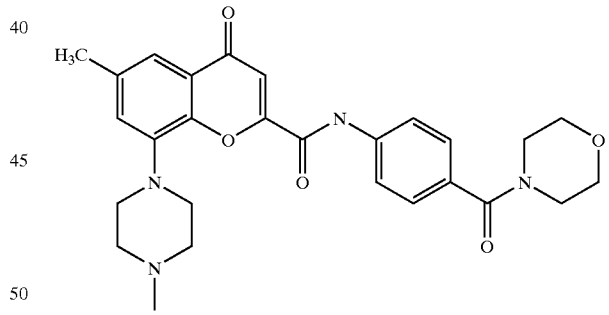

6-Methyl-8-(4-methyl-piperazin-1-yl)-4-oxo-4H-chromene-2-carboxylic acid [4-morpholin-4-yl-methanoyl)-phenyl]-amide This compound was prepared from 6-Methyl-8-(4-methyl-piperazin-1-yl)-4-oxo-4H-chromene-2-carboxylic acid hydrochloride (Reference Example 4) and 1-(4-aminophenyl)-1-morpholin-4-yl-methanone (Reference Example 14) as prepared in Example 1, yielding a yellow solid. LCMS-m/z=491.6.

EXAMPLE 64

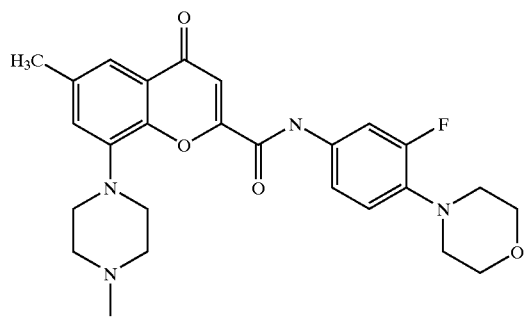

6-Methyl-8-(4-methyl-piperazin-1-yl)-4-oxo-4H-chromene-2-carboxylic acid (3-fluoro-4-morpholin-4-yl-phenyl)-amide This compound was prepared from 6-Methyl-8-(4-methyl-piperazin-1-yl)-4-oxo-4H-chromene-2-carboxylic acid hydrochloride (Reference Example 4) and 3-fluoro-4-morpholin-4-yl-phenylamine (Reference Example 16) as prepared in Example 1, yielding a yellow solid.

LCMS-m/z=504.5.

EXAMPLE 65

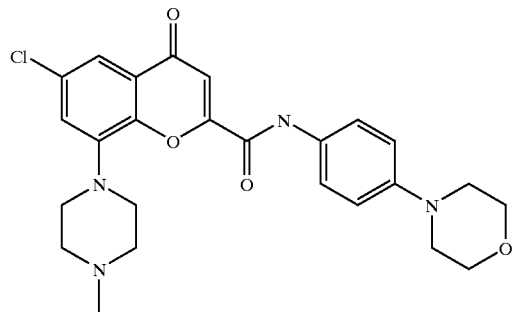

6-Chloro-8-(4-methyl-piperazin-1-yl)-4-oxo-4H-chromene-2-carboxylic acid (4-morpholin-4-yl-phenyl)-amide This compound was prepared from 6-chloro-8-(4-methyl-piperazin-1-yl)-4-oxo-4H-chromene-2-carboxylic acid hydrochloride (Reference Example 5) and 4-morpholin-4-yl-phenylamine (Reference Example 20) as prepared in Example 1, yielding a yellow solid.

LCMS-m/z=483.3.

EXAMPLE 66

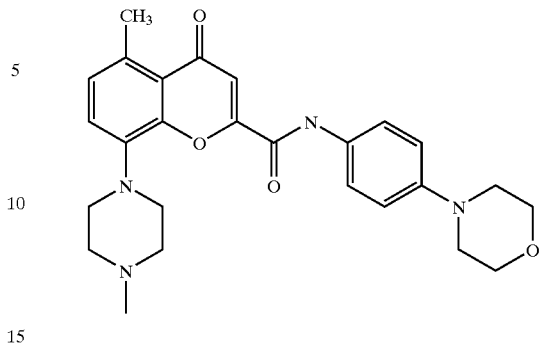

5-Methyl-8-(4-methyl-piperazin-1-yl)-4-oxo-4H-chromene-2-carboxylic acid (4-morpholin-4-yl-phenyl)-amide This compound was prepared from 5-methyl-8-(4-methyl-piperazin-1-yl-4-oxo-4H-chromene-2-carboxylic acid hydrochloride (Reference Example 6) and 4-morpholin-4-yl-phenylamine (Reference Example 20) as prepared in Example 1, yielding a yellow solid (116 mg=84%) LCMS-m/z=463.5.

EXAMPLE 67

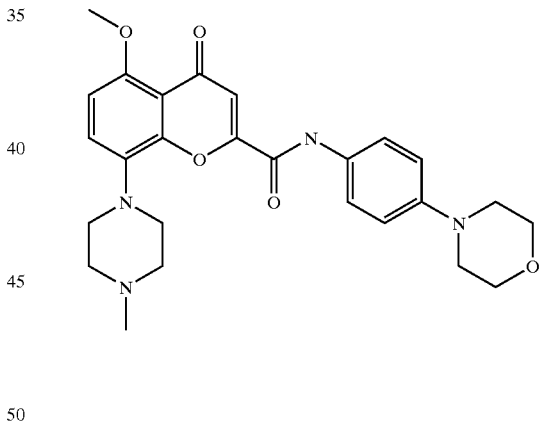

5-Methoxy-8-(4-methyl-piperazin-1-yl)-4-oxo-4H-chromene-2-carboxylic acid (4-morpholin-4-yl-phenyl)-amide This compound was prepared from 5-methoxy-8-(4-methyl-piperazin-1-yl)-4-oxo-4H-chromene-2-carboxylic acid hydrochloride (Reference Example 7) and 4-morpholin-4-yl-phenylamine (Reference example 20) as prepared in Example 1, yielding a yellow solid (149 mg=50%) LCMS-m/z=479.4.

The following additional examples incorporate 4-substituted piperazine-1-yl-phenyl amides similar in structure to Examples 44–54.

EXAMPLE 68

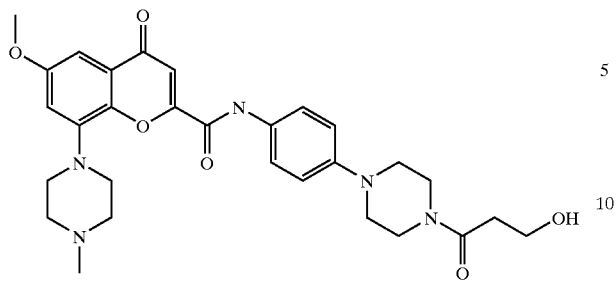

6-Methoxy-8-(4-methyl-piperazin-1-yl)-4-oxo-4H-chromene-2-carboxylic acid {4-[4-(3-hydroxy-propanoyl)-piperazin-1-yl]-phenyl}-amide 6-Methoxy-8-(4-methyl-piperazin-1-yl)-4-oxo-4H-chromene-2-carboxylic acid (4-piperazin-1-yl-phenyl)-amide (Example 43) (1.5 gram, 2.12 mmol) was placed in a 100 mL flask with 50 mL of $CH_2Cl_2$. This suspension was treated with triethylamine (4 equivalents, 1.2 mL, 8.5 mmol) and β-propionylactone (0.2 mL, 3.2 mmol) and the reaction stirred at room temperature for 2 hours, then heated to 50° C. for 2 hours. Then 0.8 mL more of b-propionylactone was added and the reaction heated for 4 hours more. The reaction was allowed to cool to room temperature and then concentrated (1 mm Hg pressure). The concentrate was treated with saturated aqueous sodium bicarbonate and the resulting solid collected by vacuum filtration. The residue was purified by chromatography on silica eluting with 2% methanol in chloroform, then concentrated (1 mm Hg pressure). Then triturated with either to yield a yellow powder with was dried under high vacuum for 48 h at 50° C. (100 mg) LCMS-m/z 550, mp=195–197° C.

EXAMPLE 69

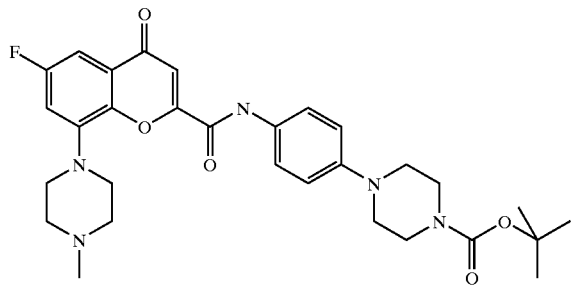

4-[({1-[6-Fluoro-8-(4-methyl-piperazin-1-yl)-4-oxo-4H-chromen-2-yl]-methanoyl}-amino)-phenyl]-piperazine-1-carboxylic acid tert-butyl ester This compound was prepared from 6-Fluoro-8-(4-methyl-piperazin-1-yl)-4-oxo-4H-chromene-2-carboxylic acid hydrochloride (Reference Example 3) and 4-(4-Amino-phenyl)-piperazine-1-carboxylic acid tert-butyl ester (Reference Example 17) according to the method of Example 42 to yield (1.65 grams, 64%) of a yellow powder LCMS-m/z=556; mp=219–220° C.

EXAMPLE 70

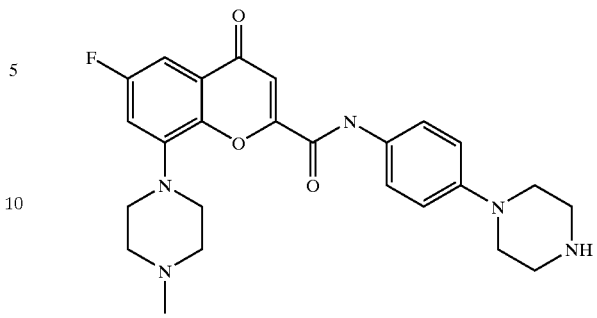

4-[4-({1-[6-Fluoro-8-(4-methyl-piperazin-1-yl)-4-oxo-4H-chromene-2-carboxylic acid (4-piperazin-1-yl-phenyl)-amide This compound was prepared from 4-[4-({1-[6-Fluoro-8-(4-methyl-piperazin-1-yl)-4-oxo-4H-chromen-2-yl]-methanoyl}-amino)-phenyl]-piperazine-1-carboxylic acid tert-butyl ester, as prepared in Example 69, using the method of Example 43 to yield a yellow solid.

LCMS-m/z=466.

EXAMPLE 71

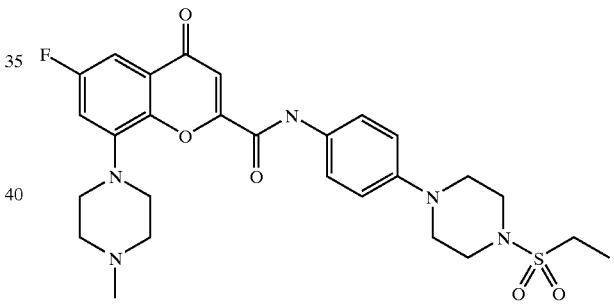

6-Fluoro-8-(4-methyl-piperazin-1-yl)-4-oxo-4H-chromene-2-carboxylic acid [4-(4-ethanesulfonyl-piperazin-1-yl)-phenyl]-amide 4-[4-({1-[6-Fluoro-8-(4-methyl-piperazin-1-yl)-4-oxo-4H-chromene-2carboxylic acid (4-piperazin-1-yl-phenyl)-amide ditrifluoroacetate (the free acid of which was prepared as in Example 70) (4.0 grams, 5.77 mmol) was placed in a flask with 50 mL of $CH_2Cl_2$ and triethylamine (3.2 mL and 23 mmol) and ethylsulfonyl chloride was added (0.6 mL, 6.35 mmol) portionwise (0.1 mL at a time) over 15 minutes and allowed to stir at room temperature for 20 hours. The reaction was concentrated (1 mm Hg pressure) and then saturated aqueous sodium bicarbonate was added and extracted with $CHCl_3$. The organic fractions were combined, washed with saturated sodium chloride, dried ($MgSO_4$) concentrated (1 mm Hg pressure) to give a yellow solid which was recrystallized from methanol to give 1.33 grams of product LCMS-m/z=558, mp=233–234° C.

EXAMPLE 72

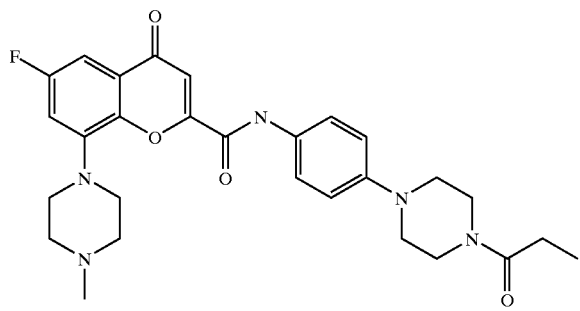

6-Fluoro-8-(4-methyl-piperazin-1-yl)-4-oxo-4H-chromene-2-carboxylic acid [4-(4-propionyl-piperazin-1-yl)phenyl]-amide 4-[4-({1-[6-Fluoro-8-(4-methyl-piperazin-1-yl)-4-oxo-4H-chromene-2-carboxylic acid (4-piperazin-1-yl-phenyl)-amide ditrifluoroacetate (the free acid of which was prepared as in Example 70) (0.69 grams, 1,00 mmol) was placed in a flask with 25 mL of $CH_2Cl_2$ and triethylamine (0.56 mL and 4 mmol) and propionyl chloride was added (0.95 mL, 1.1 mmol) and the reaction allowed to stir at room temperature for 20 hours. The residue was purified by chromatography on silica eluting with 2% methanol in chloroform, then concentrated (1 mm Hg pressure). The residue was triturated with either then digested with $CHCl_3$ and the $CHCl_3$ concentrated to yield a yellow powder which was dried under high vacuum for 48 h at 45° C. (260 mg) LCMS-m/z=522, mp=244–245° C.

EXAMPLE 73

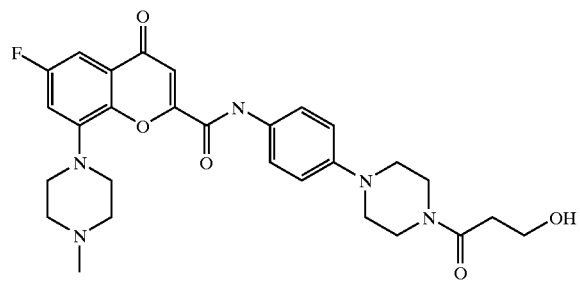

6-Fluoro-8-(4-methyl-piperazin-1-yl)-4-oxo-4H-chromene-2-carboxylic acid {4-[4-(3-hydroxy-propanoyl)-piperazin-1-yl]-phenyl}-amide This compound was prepared from 6-Fluoro-8-(4-methyl-piperazin-1-yl)-4-oxo-4H-chromene-2-carboxylic acid (4-piperazin-1-yl-phenyl)-amide and β-propionylactone using the method described above in Example 68 to yield 65 mg of a yellow powder LCMS-m/z=538, mp=195–199° C.

The following exemplifies a substituted chromene-2-"reverse amide" (or substituted chromene-2-yl-benzamide).

EXAMPLE 74

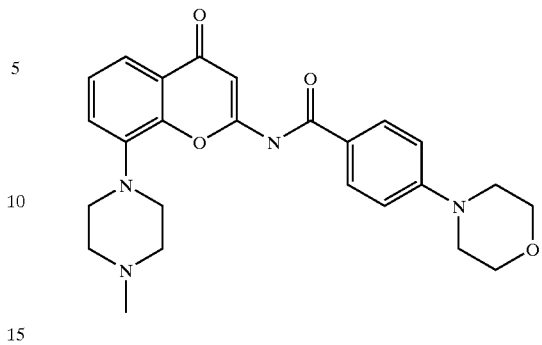

N-8-(4-Methyl-piperazin-1-yl)-4-oxo-4H-chromen-2-yl]-4-morpholin-4-yl-benzamide 8-(4-Methyl-piperazin-1-yl)-4-oxo-4H-chromene-2-carboxylic acid hydrochloride Reference Example 1 (227 mg, 0.69 mmol), triethylamine (2 equivalents, 1.389 mmol, 0.193 mL) and diphenylphosphoryl azide (0.69 mmol, 0.15 mL) were stirred in toluene (10 mL) at 65° C. for 30 minutes. The reaction was allowed to cool to 22° C. and 4-morpholinobenzonoic acid (0.7 mmol, 145 mg), more triethylamine (0.051 mL, 0.7 mmol), and $CH_3CN$ (5 mL) were added and the reaction heated to reflux for 1 hour. The reaction was concentrated (1 mm Hg pressure) the residue was partitioned between 1N methanesufonic acid and ether. The acid layer was then basified with solid $K_2CO_3$ and the product extracted in to $CHCl_3$. The organic layer was dried ($MgSO_4$) and concentrated under reduced pressure to leave a yellow solid which was further purified with silica chromatography using $CHCl_3$ to 4% $CH_3OH$ in $CHCl_3$. Concentration of the fractions containing product yielded 13 mg of product LC/MS-m/z=449.

Enantiomers of 8-(4-Methyl-piperazin-1-yl)-chroman-2-carboxylic acid (4-morpholin-4-yl-phenyl)-amide.

EXAMPLE 75

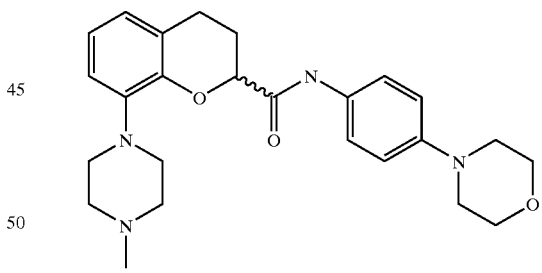

racemic-8-(4-Methyl-piperazin-1-yl)-chroman-2-carboxylic acid (4-morpholin-4-yl-phenyl)-amide racemic-8-(4-Methyl-1-piperazin-1-yl)-chroman-2-carboxylic acid hydrochloride (Example 75a) (1.04 mmol) was dissolved in anhydrous N,N-dimethylformamide (40 ml) and in the following were added in order: HOBt (0.17 g, 1.14 mmol), TBTU (0.37 g, 1.14 mmol) then triethylamine (0.6 ml, 4.2 mmol). After stirring for 5 min at room temperature, 4-(4-morpholinyl)aniline (reference example 20) (0.185 g, 1.14 mmol) was added and the reaction stirred overnight at room temperature.

The solution was concentrated in vacuo, the remains were partitioned between chloroform/saturated sodium bicarbonate, extracted (×3) with chloroform, dried (MgSO₄) and in concentrated in vacuo to give the crude product.

The crude product was chromatographed on a Waters Delta Prep 4000 using 1 PrepPak cartridge (Porasil 37–55 μm 125 Å) eluting with 2.5% methanol/chloroform. The product was collected to give a yellow oil. Ethyl acetate was added to the oil. The solution was refluxed then cooled the yellow solid was filtered to give 55 mg (12% yield) of racemic-8-(4-methyl-piperazin-1-yl)chroman-2-carboxylic acid (4-morpholin-4-yl-phenyl)-amide (mp 215–216° C.). The mother liquor contained 76 mg that was used in the chiral separation described below. LC/MS (M+1) m/z=437.

Example 75a racemic-8-(4-Methyl-1-piperazin-1-yl)-chroman-2-carboxylic acid hydrochloride Ethyl 8-(4-methyl-1-piperazin-1-yl)-4-oxo-4H-chromen-2-carboxylate (Reference Example 1) (0.74 g, 2.3 mmol) was dissolved in glacial acetic acid (50 ml) and 10% palladium on carbon (80 mg) was added. The mixture was hydrogenated on a Paar apparatus (50 psi) at 70° C. for 3 h. Then, concentrated HCl and 10%palladium on carbon (100 mg) were added and the mixture was again subjected to hydrogenation (50 psi) at 70° C. for 1 h. The reaction was allowed to cool, the catalyst was filtered and the solution was concentrated in vacuo. Toluene was repeatedly added and the solution concentrated to give racemic-8-(4-Methyl-1-piperazin-1-yl)-chroman-2-carboxylic acid hydrochloride as a foam that was used without further purification in the next reaction. LC/MS (M+1) m/z=277.

EXAMPLE 76

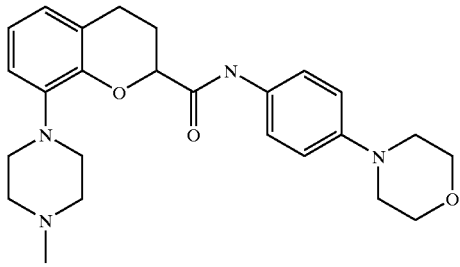

(+)-8-(41-Methyl-piperazin-1-yl)-chroman-2-carboxylic acid (4-morpholin-4-yl-phenyl)-amide The enantiomers of racemic-8-(4-Methyl-piperazin-1-yl)-chroman-2-carboxylic acid (4-morpholin-4-yl-phenyl)-amide (Example 75) (0.52 g, 1.19 mmol) were separated by the is use of a chiral column (ChiralPak AD, 5 cm×50 cm, 20μ). The faster (+)isomer (example 76) was eluted with 45% isopropanol/hexane and the slower (−)isomer (example 77) was eluted with 75% isopropanol/hexane.

The faster (+)isomer (example 76) was obtained as a white solid (250 mg, mp 206–207° C., α_D+92.66 in dichloromethane). LC/MS (M+1) m/z=437.

EXAMPLE 77

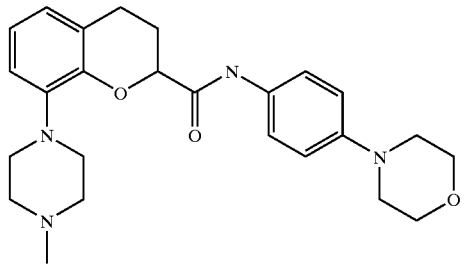

(−)-8-(4-Methyl-piperazin-1-yl)-chroman-2-carboxylic acid (4-morpholin-4-yl-phenyl)-amide The enantiomers of racemic-8-(4-Methyl-piperazin-1-yl)-chroman-2-carboxylic acid (4-morpholin-4-yl-phenyl)-amide (Example 75) (0.52 g, 1.19 mmol) were separated by the use of a chiral column (ChiralPak AD, 5 cm×50 cm, 20μ). The faster (+)isomer (example 76) was eluted with 45% isopropanol/hexane and the slower (−)isomer (example 77) was eluted with 75% isopropanol/hexane.

The slower (−)isomer (example 77) was obtained as obtained as a light purple solid (260 mg, mp 205.5–207° C., α_D−91.08 in dichloromethane). LC/MS (M+1) m/z=437.

Enantiomers of 8-(4-methyl-piperazin-1-yl)-4-oxo-chroman-2-carboxylic acid 4-morpholin-4-yl-phenyl)-amide.

EXAMPLE 78

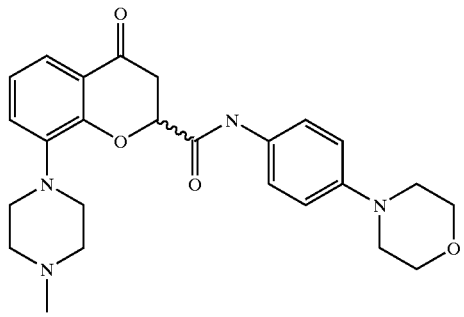

racemic-8-(4-methyl-piperazin-1-yl)-4-oxo-chroman-2-carboxylic acid (4-morpholin-4-yl-phenyl)-amide Racemic-8-(4-methyl-1-piperazin-1-yl)-4-oxo-chroman-2-carboxylic acid hydrochloride (Example 78a) (1.04 mmol) was dissolved in anhydrous N,N-dimethylformamide (40 ml) and the following were added in order: HOBt (0.17 g, 1.114 mmol), TBTU (0.37 g, 1.14 mmol) then triethylamine (0.6 ml, 4.2 mmol). After stirring for 5 min at room temperature, 4-(4-morpholinyl)aniline (reference example 20) (0.185 g, 1.14 mmol) was added and the reaction stirred overnight at room temperature.

The solution was concentrated in vacuo, the remains were partitioned between chloroform/saturated sodium bicarbonate, extracted (×3) with chloroform, dried (MgSO₄) and concentrated in vacuo to give the crude product.

The crude product was chromatographed on a Waters Delta Prep 4000 using 1 PrepPak cartridge (Porasil 37–55 μm 125 Å) eluting with 2.5% methanol/chloroform. The product was collected to give a yellow oil. Ethyl acetate was added to the oil. The solution was refluxed then cooled the yellow solid was filtered to give 55 mg (12% yield) of racemic-8-(4-methyl-piperazin-1-yl)-4-oxo-chroman-2-carboxylic acid (4-morpholin-4-yl-phenyl)-amide (mp 215–216° C.). The mother liquor contained 76 mg that was used in the chiral separation described below. LC/MS (M+) m/z=451.

Example 78a racemic-8-(4-Methyl-1-piperazin-1-yl)-4-oxo-chroman-2-carboxylic acid hydrochloride racemic-Ethyl-8-(4-methyl-1-piperazinyl) 4-oxo-chroman-2-carboxylate (Example 78b) (0.33 g, 1.04 mmol) was dissolved in 6 M HCl (20 ml) and heated to 100° C. for 1.5 h. The reaction was allowed to cool. The solution was concentrated in vacuo and anhydrous toluene was added (×3) and the solution was again concentrated in vacuo to give racemic-8-(4-Methyl-1-piperazin-1-yl)-4-oxo-chroman-2-carboxylic acid hydrochloride as a yellow foam (0.44 g, quantitative yield) that was used as is in the next reaction. LC/MS (M+1) m/z=291.

Example 78b racemic-Ethyl-8-(4-methyl-1-piperazin-1-yl)-4-oxo-chroman-2-carboxylate Racemic-Ethyl-8-(4-methyl-1-piperazin-1-yl)-4-hydroxy-chroman-2-carboxylate (Example 78c) (0.43 g, 1.3 mmol) was dissolve in anhydrous dichloromethane (35 ml) and manganese dioxide (1.2 g, 13 mmol) was added. The reaction stirred at room temperature overnight.

The reaction was filtered through diatomaceous earth and the solvent was removed in vacuo to give racemic-Ethyl-8-(4-methyl-1-piperazin-1-yl)-4-oxo-chroman-2-carboxylate as a white solid (0.37 g, 86% yield) that was used as is in the next reaction. GC/MS (EI, M+) m/z=318.

Example 78c racemic-Ethyl-8-(4-methyl-1-piperazin-1-yl)-4-hydroxy-chroman-2-carboxylate Ethyl 8-(4-methyl-1-piperazin-1-yl)-4-oxo-4H-chroman-2-carboxylate (reference example 1) (0.48 g, 1.5 mmol) was dissolved in glacial acetic acid (50 ml) and 10% palladium on carbon (100 mg) was added. The mixture was hydrogenated on a Paar apparatus (50 psi) at 70° C. for 3 h.

The reaction was allowed to cool, the catalyst was filtered and the solution was concentrated in vacuo. Ethyl acetate/saturated sodium bicarbonate was added to the remains and the mixture was extracted (×3) with ethyl acetate, dried (MgSO$_4$) and stripped to give racemic-Ethyl-8-(4-methyl-1-piperazin-1-yl)-4-hydroxy-chroman-2-carboxylate (0.43 g, 90% yield) as a yellow oil. GC/MS (EI, M+) m/z 320.

EXAMPLE 79

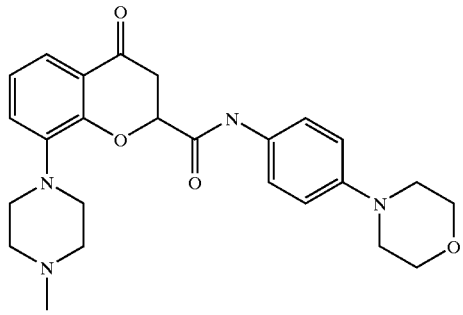

8-(4-Methyl-piperazin-1-yl)-4-oxo-chroman-2-carboxylic acid (4-morpholin-4-yl-phenyl)-amide (faster running isomer)

The enantiomers of the racemic-8-(4-methyl-piperazin-1-yl)-4-oxo-chroman-2-carboxylic acid (4-morpholin-4-yl-phenyl)-amide (Example 78) (100 mg, 0.22 mmol) were separated by the use of a chiral column (ChiralPak AD, 5 cm×50 cm, 20μ). The isomers were eluted with a gradient of 35–55% isopropanol/hexane. The faster isomer was obtained as a light yellow solid (40 mg, mp 216° C. dec.) LC/MS (M+) m/z=451.

EXAMPLE 80

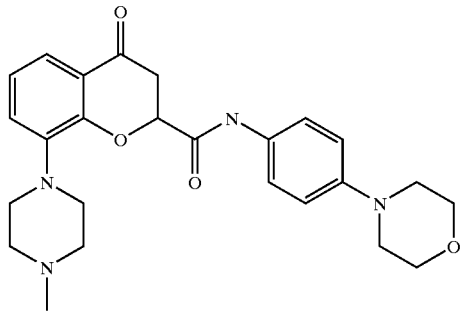

8-(4-Methyl-piperazin-1-yl)-4-oxo-chroman-2-carboxylic acid (4-morpholin-4-yl-phenyl)-amide (slower running isomer)

The enantiomers of the racemic-8-(4-methyl-piperazin-1-yl)-4-oxo-chroman-2-carboxylic acid (4-morpholin-4-yl-phenyl)-amide (100 mg, 0.22 mmol) were separated by the use of a chiral column (ChiralPak AD, 5 cm×50 cm, 20μ). The isomers were eluted with a gradient of 35–55% isopropanol/hexane. The slower isomer was obtained as an off white solid (32 mg, mp 215° C. dec.) LC/MS (M+1) m/z=451.

EXAMPLE 81

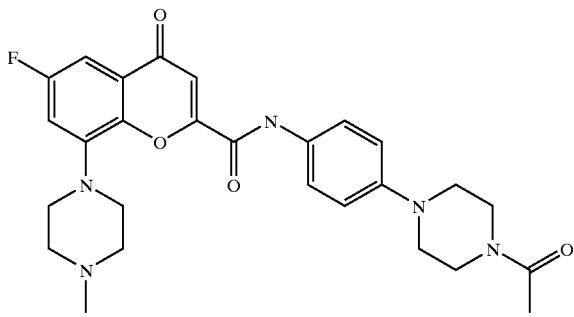

4-[4-({1-[6-Fluoro-8-(4-methyl-piperazin-1-yl)-4-oxo-4H-chromen-2-yl]-methanoyl}-amino)-phenyl]-piperazine-1-carboxylic acid ethylamide 6-Fluoro-8-(4-methyl-piperazin-1-yl)-4-oxo-4H-chromene-2-carboxylic acid (4-piperazin-1-yl-phenyl)-amide (Example 71) (150 mg, 0.216 mmol) was placed in a 50 mL flask with 10 of CH$_2$Cl$_2$. This suspension was treated with triethylamine (0.1 mL, 0.67 mmol) and ethylisocyanate (0.21 mL, 18.7 mg, 0.26 mmol) and the reaction stirred at room temperature for 18 hours. The reaction was concentrated (1 mm Hg pressure) and the concentrate purified by chromatography on silica eluting with 1% methanol in chloroform, then concentrated (1 mm Hg pressure). Then triturated with either to yield a yellow powder with was dried under high vacuum for 48 h at 50° C. (79 mg) LCMS-AP+ 537.4, mp=236–238° C.

EXAMPLE 82

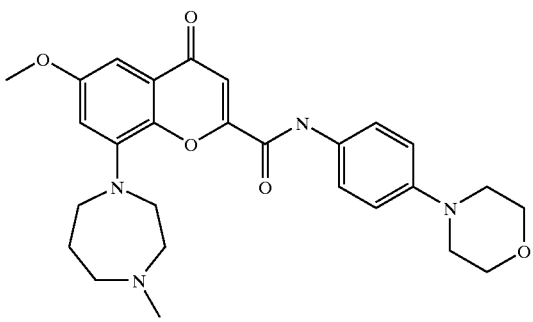

6-Methoxy-8-(4-methyl-[1,4]diazepan-1-yl)-4-oxo-4H-chromene-2-carboxylic acid (4-morpholin-4-yl-phenyl)amide Into a 100 mL round bottom flask equipped with a nitrogen inlet and magnetic stirrer is added 327 mg (0.89 mmol, 1.0 equiv.) of 6-Methoxy-8-(4-methyl-[1,4]diazepan-1-yl)-4-oxo-4H-chromene-2-carboxylic acid hydrochloride salt (Reference Example 23). This material is dissolved in 20 mL of DMF and then 189 mg (1.06 mmol, 1.2 equiv.) of 4-morpholinoaniline is added. To the stirred solution is quickly added simultaneously added 568 mg (1.77 mmol, 2.0 equiv.) of TBTU and 239 mg (1.77 mmol, 2.0 equiv.) of HOBT. At this point 457 mg, 577 µL (25.2 mmol, 4.0 equiv.) is added via syringe over 5 minutes. The reaction is allowed to stir at room temperature for 18 hrs, then is concentrated on a rotary evaporator under high vacuum in order to remove the DMF. The residue is triturated with methanol and the crude solids are recovered by filtration. These residues are then purified by flash chromatography using a gradient of 5–10% methanol in methylene chloride as eluent. The eluted material, which is obtained from chromatography, is concentrated, dried under high vacuum, suspended in methylene chloride, dried over K$_2$CO$_3$, concentrated, then crystallized from methanol to give the free base of the pure product as 345 mg (79%) of a yellow solid. Mass Spec.: calc. for [C$_{27}$H$_{32}$FN$_4$O$_5$+H]$^+$ Theor. m/z=393; Obs.=393.

EXAMPLE 83

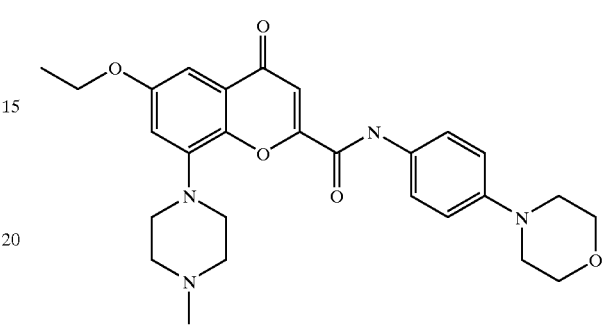

6-Ethoxy-8-(4-methyl-piperazin-1-yl)-4-oxo-4H-chromene-2-carboxylic acid (4-morpholin-4-yl-phenyl)-amide Into a 100 mL flask equipped with a nitrogen inlet and magnetic stirrer is placed 133 mg (0.748 mmol, 1.1 equiv.) of 4-morpholinoaniline, which is then dissolved in 20 mL of methylene chloride. To this mixture is then added 290 mg, 367 µL (2.24 mmol, 3.3 equiv.) of ethylduisopropyl amine, followed by addition of a solution of 250 mg (0.68 mmol, 1.0 equiv.) of 6-ethoxy-8-(4-methyl-piperazin-1-yl)-4-oxo-4H-chromene-2-carbonyl chloride (Reference Example 23) which has been dissolved in 10 ml of methylene chloride. The reaction is allowed to stir for 4 hr, after which no further formation of product was seen by LC/MS. The crude reaction was concentrated on a rotary evaporator, then triturated with 10 mL of methanol. The crude solids were collected by filtration, then subjected to flash chromatography using a gradient of from 2 to 20% methanol in methylene chloride. Recrystallization from methylene chloride and hexanes afforded 55 mg (16%) of the pure product as a yellow solid.

Mass Spec.: calc. for [C$_{27}$H$_{32}$N$_4$O$_5$+H]$^+$ Theor. m/z=493; Obs.=493.

EXAMPLE 84

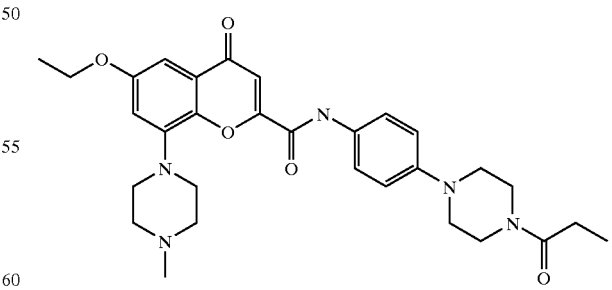

6-Ethoxy-8-(4-methyl-piperazin-1-yl)-4-oxo-4H-chromene-2-carboxylic acid [4-(4-propionyl-piperazin-1-yl)-phenyl]-amide This compound was prepared from 250 mg (0.68 mmol, 11.0 equiv.) of 6-Ethoxy-8-(4-methyl-piperazin-1-yl)-4- oxo-4H-chromene-2-carbonyl chloride (Reference Example 23) and 175 mg (0.748 mmol, 1.1 equiv.) of 1-[4-(4-Aminophenyl)-piperazin-1-yl]-propan-1-one by an analogous procedure to that used to prepare the 4-morpholino aniline derivative, to give 45 mg (12%) of the desired product as a yellow solid.

Mass Spec.: calc. for $[C_{30}H_{37}N_5O_5+H]^+$ Theor. m/z=548; Obs.=548.

EXAMPLE 85

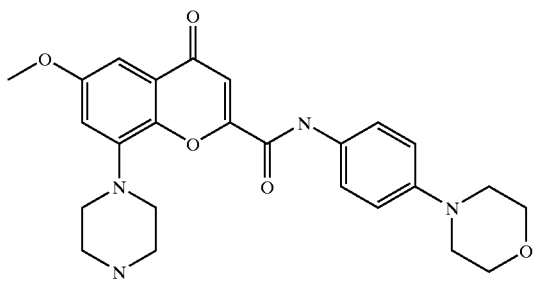

6-Methoxy-4-oxo-8-piperazin-1-yl-4H-chromene-2-carboxylic acid (4-morpholin-4-yl-phenyl)-amide Into a 50 mL round bottom flask equipped with a reflux condenser, nitrogen inlet and magnetic stirrer is placed 50 mg (0.115 mmol, 1.0 equiv.) of 6-Methoxy-8-(4-methyl-piperazin-1-yl)-4-oxo-4H-chromene-2-carboxylic acid (4-morpholin-4-yl-phenyl)-amide (Example 31) and 10 mL of 1,2 dichloroethane. To this solution is then added via syringe 49 mg, 37 µL (0.348 mmol, 3.0 equiv.) of 1-chloroethyl chloroformate. A precipitate forms, indicating formation of an intermediate. The reaction is heated to reflux for 3 days, whereupon an analysis of an aliquot by LC/MS indicates only a trace of product has formed. At this time 52 mg (0.345 mmol, 3.0 equiv.) of sodium iodide are added to the refluxing reaction. LC/MS analyses then progressively show formation of demethylated product over 5 additional days. The reaction is then cooled, concentrated on a rotary evaporator, then dried over $K_2CO_3$ as a suspension in methylene chloride containing methanol, removal of solids by filtration, followed by flash chromatography of the solution, using a gradient of 5 to 20% methanol in methylene chloride, gives 34 mg (64%) of the pure product as a reddish solid.

Mass Spec.: calc. for $[C_{25}H_{28}N_4O_5+H]^+$ Theor. m/z 465; Obs.=465.

EXAMPLE 86

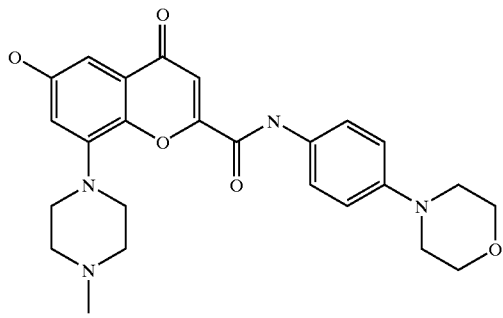

6-Hydroxy-8-(4-methyl-piperazin-1-yl)-4-oxo-4H-chromene-2-carboxylic acid (4-morpholin-4-yl-phenyl)-amide Into a 50 mL round bottom flask equipped with a reflux condenser, nitrogen inlet and magnetic stirrer is placed 50 mg (0.115 mmol, 1.0 equiv.) of 6-Methoxy-8-(4-methyl-piperazin-1-yl)-4-oxo-4H-chromene-2-carboxylic acid (4-morpholin-4-yl-phenyl)-amide (Example 31) and 20 mL of methylene chloride. To this solution is added 1 mL of a 1N solution of boron tribromide in methylene chloride. The reaction is stirred at room temperature for 2.5 days at which time it is complete by LC/MS. The reaction is concentrated on a rotary evaporator, then methanol is added. The methanol is concentrated and readied 5 times, until the $BBr_3$ is removed as HBr and trimethyl borate. The solid hydrobromide salt residue, which is obtained, is >85% pure product by LC/MS. Mass Spec.: calc. for $[C_{25}H_{28}N_4O_5+H]^+$ Theor. m/z=465; obs.=465.

EXAMPLE 87

(Method 1)

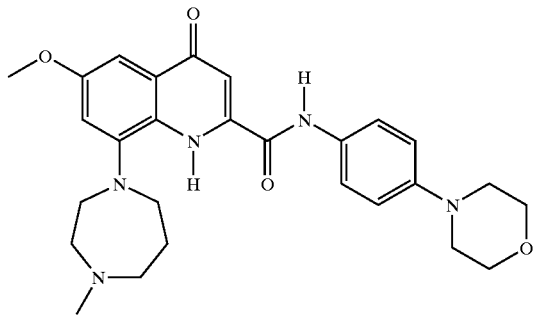

6-Methoxy-8-(4-methyl-[1,4]diazepan-1-yl)-4-oxo-1,4-dihydro-quinoline-2-carboxylic acid (4-morpholin-4-yl-phenyl)-amide To a solution of 6-methoxy-8-(4-methyl-[1,4]diazepan-1-yl)-4-oxo-1,4-dihydro-quinoline-2-carboxylic acid (2.10 mmol) (Reference Example 25b) and diisopropylethyl amine (1.4 mL, 8.6 mmol) in 34 mL dimethylformamide was added TBTU (1.40 g, 4.36 mmol) and HOBt (0.588 g, 4.35 mmol) followed by the addition of 4-morpholinoaniline (0.463 g, 2.60 mmol). The resulting dark brown solution was stirred at room temperature under nitrogen for 19 hours. The reaction was concentrated in vacuo and the resulting crude product was taken up in methylene chloride/methanol. Filtration of the resulting mixture afforded some product as a yellow solid. The filtrates were concentrated and partitioned between methylene chloride and saturated aqueous sodium bicarbonate. The organic layer was washed with saturated sodium bicarbonate, dried ($MgSO_4$), and concentrated under vacuum to afford a brown solid. This was suspended in methanol and filtered to afford the desired product as a yellow solid (0.714 g, 69%). $^1$H NMR (300 MHz, DMSO, $d_6$) δ 9.97 (bs, 1H, N$\underline{H}$), 7.67 (d, 2H, $J_o$=8.8 Hz, Ar$\underline{H}_2$, & $\underline{H}_6$), 7.47 (bs, 1H, Ar$\underline{H}_5$), 7.00 (s, 1H, C=C$\underline{H}$), 6.99 (d, 2H, $J_o$=8.8 Hz, Ar$\underline{H}_3$, & $\underline{H}_5$), 6.71 (bs, 1H, Ar$\underline{H}_7$), 3.85 (s, 3H, OC$\underline{H}_3$), 3.75 (t, 4H, J=4.6 Hz, OC$\underline{H}_2$CH$_2$N), 3.70 (bs, 2H, ArNC$\underline{H}_2$CH$_2$CH$_2$NCH$_3$), 3.55 (bs, 2H, ArNC$\underline{H}_2$CH$_2$NCH$_3$), 3.09 (t, 4H, J=4.6 Hz, OCH$_2$C$\underline{H}_2$N), 2.95 (bs, 2H, ArNCH$_2$C$\underline{H}_2$NCH$_3$), 2.73 (bs, 2H, ArNCH$_2$CH$_2$C$\underline{H}_2$NCH$_3$), 2.36 (s, 3H, NC$\underline{H}_3$), 2.07 (bs, 2H, ArNCH$_2$C$\underline{H}_2$CH$_2$NCH$_3$); Mass Spec.: calc. for $[C_{27}H_{33}N_5O_4+H]^+$ Theor. m/z=492; Obs. 492.

EXAMPLE 87

(Method 2)

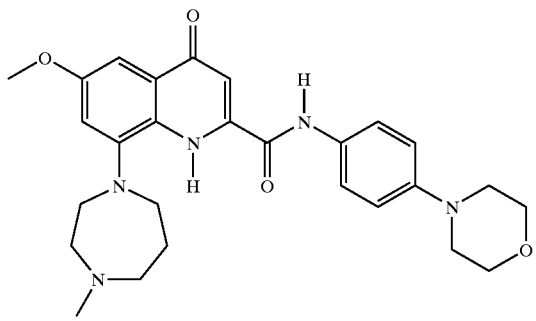

6-Methoxy-8-(4-methyl-[1,4]diazepan-1-yl)-4-oxo-1,4-dihydro-quinoline-2-carboxylic acid (4-morpholin-4-yl-phenyl)-amide A solution of 6-methoxy-8-(4-methyl-[1,4-]diazepan-1-yl)-4-(2-trimethylsilanyl-ethoxymethoxy)-quinoline-2-carboxylic acid (4-morpholin-4-yl-phenyl)-amide (Reference Example 27d) (0.989 g, 1.59 mmol) in 20 mL methanol was poured into 300 mL 0.05 N hydrochloric acid. The clear dark yellow solution became cloudy within 5 minutes. The mixture was stirred at room temperature for 45 minutes and then adjusted to pH 7 with 10% sodium hydroxide. The resulting yellow precipitate was isolated by filtration, washed with water, and dried under high vacuum to afford the desired product as a yellow solid (0.629 g, 80%). $^1$H NMR (300 MHz, DMSO, d$_6$) δ 9.97 (s, 1H,C(O)N H), 7.67 (d, 2H, J$_o$=8.8 Hz, ArH$_2$, & H$_{6'}$), 7.47 (bs, 1H, Ar H$_5$), 7.00 (s, 1H, C=CH), 6.99 (d, 2H, J$_o$=8.8 Hz, ArH$_{3'}$ & H$_{5'}$), 6.71 (bs, 1H, ArH$_7$), 3.85 (s, 3H, OCH$_3$), 3.75 (t, 4H, J=4.6 Hz, OCH$_2$CH$_2$N), 3.70 (bs, 2H, ArNC H$_2$CH$_2$CH$_2$NCH$_3$), 3.55 (bs, 2H, ArNCH$_2$CH$_2$NCH$_3$), 3.09 (t, 4H, J=4.6Hz, OCH$_2$CH$_2$N), 2.95 (bs, 2H, ArNCH$_2$C H$_2$NCH$_3$), 2.73 (bs, 2H, ArNCH$_2$CH$_2$CH$_2$NCH$_3$), 2.36 (s, 3H, NCH$_3$), 2.07 (bs, 2H, ArNCH$_2$CH$_2$CH$_2$NCH$_3$); Mass Spec.: calc. for [C$_{27}$H$_{33}$N$_5$O$_4$+H]$^+$ Theor. m/z=492; Obs.=492. Analysis for C$_{27}$H$_{33}$N$_5$O$_4$·1.0eqHCl·0.3eqH$_2$O: Calculated C, 60.79; H, 6.54; N, 13.13. Found C, 60.82; H, 6.53; N, 13.17.

EXAMPLE 88

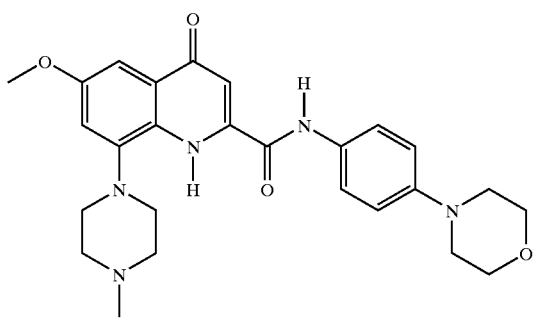

6-Methoxy-8-(4-methyl-piperazin-1-yl)-4-oxo-1,4-dihydro-quinoline-2-carboxylic acid (4-morpholin-4-yl-phenyl)-amide The title compound was prepared from 8-bromo-6-methoxy-4-(2-trimethylsilanyl-ethoxymethoxy)-quinoline-2-carboxylic acid methyl ester (Reference Example 24c) according to the procedures described in Reference Example 25a and in Example 87 (Method 1). A yellow solid was obtained. Mass Spec.: calc. for [C$_{26}$H$_{31}$N$_5$O$_4$+H]$^+$ Theor. m/z=478; Obs. 478.

EXAMPLE 89

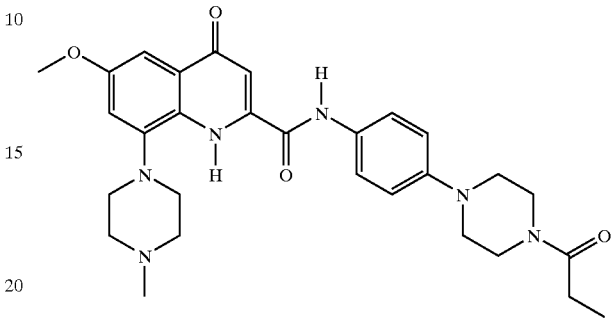

6-Methoxy-8-(4-methyl-piperazin-1-yl)-4-oxo-1,4-dihydro-quinoline-2-carboxylic acid [4-(4-propionyl-piperazin-1-yl)-phenyl]-amide The title compound was prepared from 8-bromo-6-methoxy-4-(2-trimethylsilanyl-ethoxymethoxy)-quinoline-2-carboxylic acid methyl ester (Reference Example 24c) according to the procedures described in Reference Example 25a and in Example 87 (Method 1), except that the amide was formed from 1-[4-(4-amino-phenyl)-piperazin-1-yl]-propan-1-one. A yellow solid was obtained. Mass Spec.: calc. for [C$_{29}$H$_{36}$N$_6$O$_4$+H]$^+$ Theor. m/z 533; Obs. 533.

EXAMPLE 90

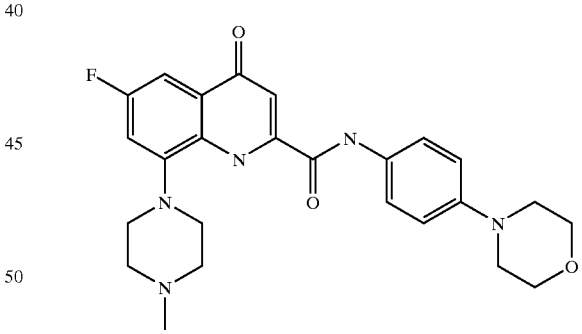

6-Fluoro-8-(4-methyl-piperazin-1-yl)-4-oxo-1,4-dihydro-quinoline-2-carboxylic acid (4-morpholin-4-yl-phenyl)-amide The title compound was prepared from 6-Fluoro-8-(4-methyl-piperazin-1-yl)-4-oxo-1,4-dihydro-quinoline-2-carboxylic acid hydrochloride salt (Reference Example 26) using the procedure described in Example 87 (Method 1). After chromatography, it is then crystallized from methanol to give the pure product as 150 mg (55%) of a yellow solid. Mass Spec.: calc. for [C$_{25}$H$_{28}$FN$_5$O$_3$+H]$^+$ Theor. m/z=466; Obs.=466.

EXAMPLE 91

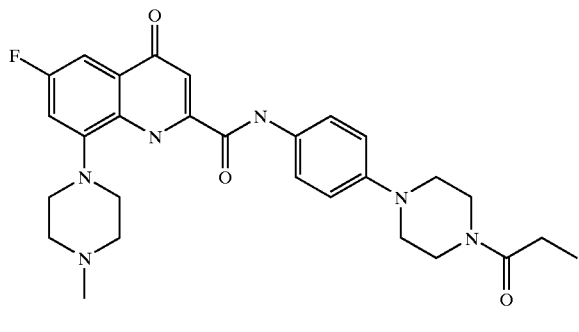

6-Fluoro-8-(4-methyl-piperazin-1-yl)-4-oxo-1,4-dihydro-quinoline-2-carboxylic acid [4-(4-propionyl-piperazin-1-yl)-phenyl]-amide The title compound was prepared from 6-Fluoro-8-(4-methyl-piperazin-1-yl)-4-oxo-1,4-dihydro-quinoline-2-carboxylic acid hydrochloride salt (200 mg, 0.59 mmol) Reference Example 26) using the procedure described in Example 87 (Method 1), 31% yield. Mass Spec.: calc. for $[C_{28}H_{33}FN_6O_3+H]^+$ Theor. m/z=521; Obs.=521.

EXAMPLE 92

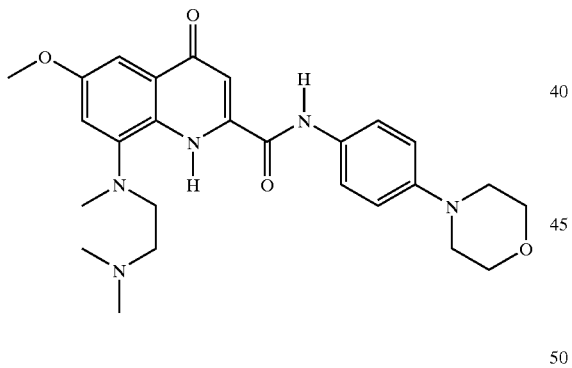

8-[(2-Dimethylamino-ethyl)-methyl-amino]-6-methoxy-4-oxo-4-dihydro-quinoline-2-carboxylic acid (4-morpholin-4-yl-phenyl)-amide The title compound was prepared from 8-bromo-6-methoxy-4-(2-trimethylsilanyl-ethoxymethoxy)-quinoline-2-carboxylic acid methyl ester (Reference Example 24c) according to the procedures described in Reference Example 25a and in Example 87 (Method 2), using N,N,N'-trimethyl ethylenediamine for the Pd catalysed coupling. A yellow solid was obtained. Mass Spec.: calc. for $[C_{26}H_{33}N_5O_4+H]^+$ Theor. m/z=480; Obs.=480.

EXAMPLE 93

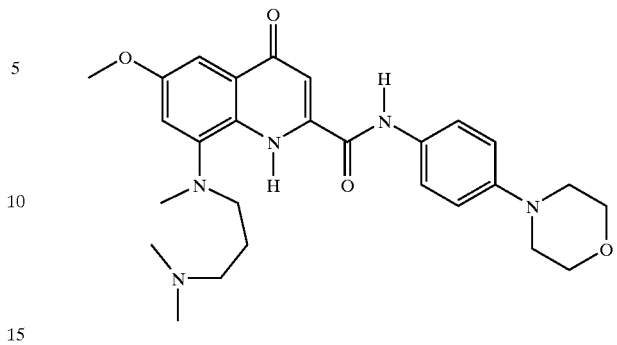

8-[(3-Dimethylamino-propyl)-methyl-amino]-6-methoxy-4-oxo-1,4-dihydro-quinoline-2-carboxylic acid (4-morpholin-4-yl-phenyl)-amide The title compound was prepared from 8-bromo-6-methoxy-4-(2-trimethylsilanyl-ethoxymethoxy)-quinoline-2-carboxylic acid methyl ester (Reference Example 24c) according to the procedures described in Reference Example 25a and in Example 87 (Method 2), using N,N,N'-trimethyl-1,3-propanediamine for the Pd catalysed coupling. A yellow solid was obtained. Mass Spec.: calc. for $[C_{27}H_{35}N_5O_4+H]^+$ Theor. m/z=494; Obs.=494.

EXAMPLE 94

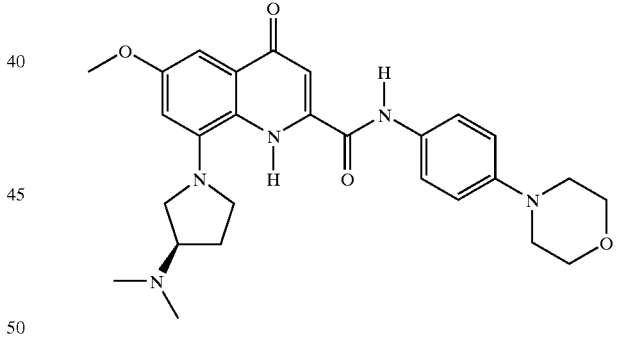

8-((3R)-(+)-3-Dimethylamino-pyrrolidin-1-yl)-6-methoxy-4-oxo-1,4-dihydro-quinoline-2-carboxylic acid (4-morpholin-4-yl-phenyl)-amide The title compound was prepared from 8-bromo-6-methoxy-4-(2-trimethylsilanyl-ethoxymethoxy)-quinoline-2-carboxylic acid methyl (Reference Example 24c) according to the procedures described in Reference Example 25a and in Example 87 (Method 2), using (3R)-(+)-3-(dimethylamino)pyrrolidine for the Pd catalysed coupling. A yellow solid was obtained. Mass Spec.: calc. for $[C_{27}H_{33}N_5O_4+H]^+$ Theor. m/z=492; Obs.=492.

EXAMPLE 95

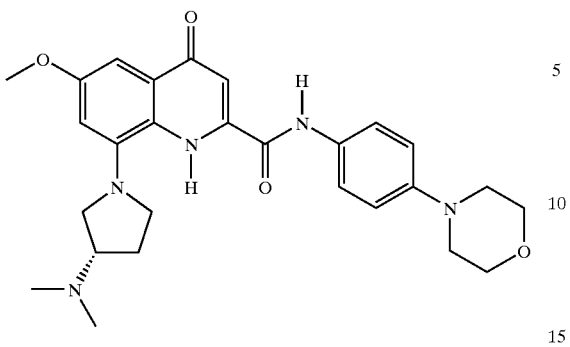

8-((3S)-(−)-3-Dimethylamino-pyrrolidin-1-yl)-6-methoxy-4-oxo-1,4-dihydro-quinoline-2-carboxylic acid (4-morpholin-4-yl-phenyl)-amide The title compound was prepared from 8-bromo-6-methoxy-4-(2-trimethylsilanyl-ethoxymethoxy)-quinoline-2-carboxylic acid methyl ester (Reference Example 24c) according to the procedures described in Reference Example 25a and in Example 87 (Method 2), using (3S)-(−)-3-(dimethylamino)pyrrolidine for the Pd catalysed coupling. A yellow solid was obtained. Mass Spec.: calc. for $[C_{27}H_{33}N_5O_4+H]^+$ Theor. m/z=492; Obs.=492.

EXAMPLE 96

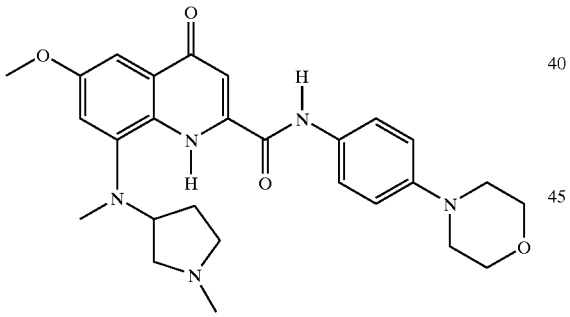

6-Methoxy-8-[methyl-(1-methyl-pyrrolidin-3-yl)-amino]-4-oxo-1,4-dihydro-quinoline-2-carboxylic acid (4-morpholin-4-yl-phenyl)-amide The title compound was prepared from 8-bromo-6-methoxy-4-(2-trimethylsilanyl-ethoxymethoxy)-quinoline-2-carboxylic acid methyl ester (Reference Example 24c) according to the procedures described in Reference Example 25a and in Example 87 (Method 2), using N,N'-dimethyl-3-aminopyrrolidine for the Pd catalysed coupling. A yellow solid was obtained. Mass Spec.: calc. for $[C_{27}H_{33}N_5O_4+H]^+$ Theor. m/z=492; Obs.=492.

EXAMPLE 97

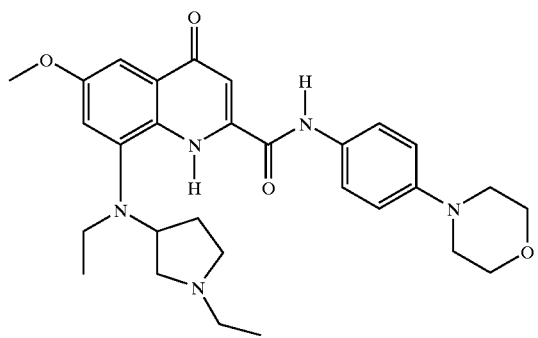

8-[Ethyl-(1-ethyl-pyrrolidin-3-yl)-amino]-6-methoxy-4-oxo-1,4-dihydro-quinoline-2-carboxylic acid (4-morpholin-4-yl-phenyl)-amide The title compound was prepared from 8-bromo-6-methoxy-4-(2-trimethylsilanyl-ethoxymethoxy)-quinoline-2-carboxylic acid methyl ester (Reference Example 24c) according to the procedures described in Reference Example 25a and in Example 87 (Method 2), using 3-diethylaminopyrrolidine for the Pd catalyzed coupling. A yellow solid was obtained. Mass Spec.: calc. for $[C_{29}H_{37}N_5O_4+H]^+$ Theor. m/z=520; Obs.=520.

EXAMPLE 98

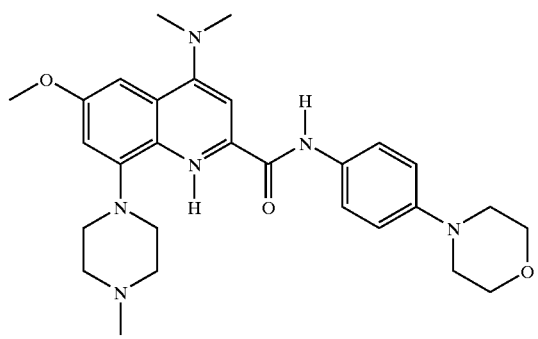

4-Dimethylamino-6-methoxy-8-(4-methyl-piperazin-1-yl)-quinoline-2-carboxylic acid (4-morpholin-4-yl-phenyl)-amide To a suspension of 8-bromo-4-dimethylamino-6-methoxy-quinoline-2-carboxylic acid (4-morpholin-4-yl-phenyl)-amide (Reference Example 28b) (139.9 mg, 0.288 mmol), N-methylpiperazine (48 µL, 0.43 mmol), and 4 Å sieves in 15 mL anhydrous toluene was added $Pd_2(dba)_2$ (15.3 mg, 16.7 µmol), BINAP (63.0 mg, 0.101 mmol) and cesium carbonate (0.436 g, 1.345 mmol). The resulting wine colored mixture was heated at reflux under nitrogen for 20 hours. The reaction mixture was cooled to room temperature and concentrated. The crude mixture was purified by flash chromatography on silica gel using a gradient of 100:0 to 95:5 methylene chloride:methanol to afford the desired product as a yellow solid (96.9 mg, 67%). $^1$H NMR (300 MHz, DMSO, $d_6$) δ 10.06 (s, 1H, C(O)NH), 7.69 (d, 2H, $J_o$=9.0 Hz, ArH$_2$, & H$_6$,), 7.58 (s, 1H, ArH$_3$), 7.58 (d, 2H, $J_o$=9.0 Hz, ArH$_3$, & H$_5$,), 6.95 (d, 1H, $J_m$=2.7 Hz, ArH$_5$), 6.76 (d, 1H, $J_m$=2.7 Hz, ArH$_7$), 3.90 (s, 3H, OCH$_3$), 3.75 (t, 4H, J=4.8 Hz, OCH$_2$CH$_2$N), 3.37 (bs, 4H, ArNCH$_2$CH$_2$N), 3.10

(t, 4H, J=4.8 Hz, OCH$_2$CH$_2$N), 3.01 (s, 6H, N(CH$_3$)$_2$), 2.71 (bs, 4H, ArNCH$_2$CH$_2$N), 2.35 (s, 3H, R$_2$NCH$_3$); Mass Spec.: calc. for [C$_{28}$H$_{36}$N$_6$O$_3$+H]$^+$ Theor. m/z=505; Obs.=505.5.

EXAMPLE 99

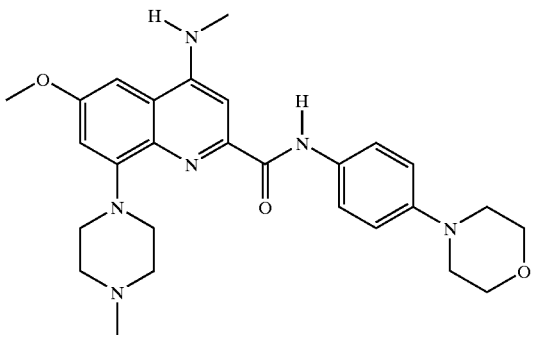

6-Methoxy-4-methylamino-8-(4-methyl-piperazin-1-yl)-quinoline-2-carboxylic acid (4-morpholin-4-yl-phenyl)-amide The title compound was prepared from 8-bromo-6-methoxy-4-oxo-1,4-dihydro-quinoline-2-carboxylic acid (Reference Example 27b) according to the procedure described for Example 98 using N-methyl amine to prepare 8-bromo-4-methylamino-6-methoxy-quinoline-2-carboxylic acid (4-morpholin-4-yl-phenyl)-amide. A glassy orange solid was obtained. Mass Spec.: calc. for [C$_{27}$H$_{34}$N$_6$O$_3$+H]$^+$ Theor. m/z=491; Obs.=491.5.

EXAMPLE 100

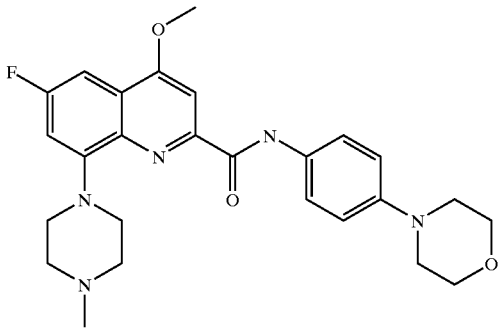

6-Fluoro-4-methoxy-8-(4-methyl-piperazin-1-yl)-quinoline-2-carboxylic acid (4-morpholin-4-yl-phenyl)-amide Into a 250 mL round bottom flask equipped with a nitrogen inlet and magnetic stirrer is added 2.01 g (6.3 mmol, 1.0 equiv.) of 6-Fluoro-4-methoxy-8-(4-methyl-piperazin-1-yl)-quinoline-2-carboxylic acid hydrochloride salt. This material is dissolved in 20 mL of DMF and then 1.35 g (7.56 mmol, 1.2 equiv.) of 4-morpholinoaniline is added. To the stirred solution is quickly added simultaneously added 4.05 g (12.6 mmol, 2.0 equiv.) of TBTU (2-(1H-benzotriazole-1-yl)-1,1,3,3-tetramethyluroniumtetrafluoroborate) and 1.7 g (12.6 mmol, 2.0 equiv.) of HOBT (1-hydroxybenzotriazole hydrate). At this point 3.25 g, 4.11 mL (25.2 mmol, 4.0 equiv.) is added via syringe over 5 minutes. The reaction is allowed to stir at room temperature for 18 hrs, then is concentrated on a rotary evaporator under high vacuum in order to remove the DMF. The residue is triturated with methanol and the crude solids are recovered by filtration. The material is then dissolved in methylene chloride and extracted with 10% sodium bicarbonate solution. The organic layer is dried and then concentrated. These residues are then purified by flash chromatography using a gradient of 5–10% methanol in methylene chloride as eluent. The material which is obtained from chromatography, is then crystallized from methanol to give the pure product as 2.83 g (93%) of a yellow solid.

Mass Spec.: calc. for [C$_{26}$H$_{30}$FN$_5$O$_3$+H]$^+$ Theor. m/z=480; Obs.=480.

EXAMPLE 101

6-Fluoro-4-oxo-8-piperazin-1-yl-4H-chromene-2-carboxylic acid (4-morpholin-4-yl-phenyl)-amide Made according to the general method of Howarth et. al. Tetrahedron, 1998, 54, 10899–10914.

Dry 6-flouro-8-(4-methyl-piperazin-1-yl)-4-oxo-4H-chromene-2-carboxylic acid [4-(4-propionyl-piperazin-1-yl)-phenyl]-amide (Example 72)(1 g, 1.9 mmol) was added to 100 mL of rigorously dried 1,2-dichloroethane in a flask under N$_2$ atmosphere and magnetic stirring. The mixture was cooled to 0° C. and freshly distilled 1-chloroethyl chloroformate (650 ul, 858 mg, 6 mmol, 3 eq) was added drop wise. The reaction was then heated under reflux for 5 hours at which time LC/MS revealed complete consumption of starting material. NaI (1 g, 1 eq) was added and heating continued for 2 days more. The reaction was then allowed to cool and filtered and evaporated to dryness under reduced pressure. MeOH (100 mL) was added and heated to reflux for 4 h, filtered hot and evaporated to dryness. The product was isolated by chromatography using silica gel and CHCl3/5% MeOH as an eluent. This gave 700 mg of the product HCl salt as a yellow solid. LCMS-m/z=508.

We claim:
1. A compound selected from: 8-(4-methyl-1-piperazinyl)-N-[4-(4-morpholinyl)phenyl]-4-oxo-4H-chromene-2-carboxamide;
2-{1-[4-(2-Methoxy-phenyl)-piperazin-1-yl]-methanoyl}-8-(4-methyl-piperazin-1-yl)-chromen-4-one;
2-{1-[4-(1-Acetyl-2,3-dihydro-1H-indol-6-yl)-piperazin-1-yl]-methanoyl}-8-(4-methyl-piperazin-1-yl)-chromen-4-one;
2-Chloro-5-(4-{1-[8-(4-methyl-piperazin-1-yl)-4-oxo-4H-chromen-2-yl]-methanoyl}-piperazin-1-yl)-benzonitrile;
2-{1-[4-(4-Methoxy-phenyl)-piperazin-1-yl]-methanoyl}-8-(4-methyl-piperazin-1-yl)-chromen-4-one;
8-(4-Methyl-piperazin-1-yl)-4-oxo-4H-chromene-2-carboxylic acid (5-furan-2-yl-1H-pyrrazol-3-yl)-amide;
8-(4-Methyl-piperazin-1-yl)-4-oxo-4H-chromene-2-carboxylic acid (4-imidazol-1-yl-phenyl)-amide;
8-(4-Methyl-piperazin-1-yl)-4-oxo-4H-chromene-2-carboxylic acid (4-[1,2,3]thiadiazol-5-yl-phenyl)-amide;
8-(4-Methyl-piperazin-1-yl)-4-oxo-4H-chromene-2-carboxylic acid 4-[1,2,3]thiadiazol-5-yl-benzylamide;
8-(4-Methyl-piperazin-1-yl)-4-oxo-4H-chromene-2-carboxylic acid [4-(4-acetyl-piperazin-1-yl)-phenyl]-amide;

8-(4-Methyl-piperazin-1-yl)-4-oxo-4H-chromene-2-carboxylic acid [4-(4-methanesulfonyl-piperazin-1-yl)-phenyl]-amide;

8-(4-Methyl-piperazin-1-yl)-4-oxo-4H-chromene-2-carboxylic acid (2-methoxy-4-morpholin-4-yl-phenyl)-amide;

8-(4-Methyl-piperazin-1-yl)-4-oxo-4H-chromene-2-carboxylic acid (3-chloro-4-morpholin-4-yl-phenyl)-amide;

8-(4-Methyl-piperazin-1-yl)-4-oxo-4H-chromene-2-carboxylic acid (4-thiomorpholin-4-yl-phenyl)-amide;

8-(4-Methyl-piperazin-1-yl)-4-oxo-4H-chromene-2-carboxylic acid (2,5-diethoxy-4-morpholin-4-yl-phenyl)-amide;

8-(4-Methyl-piperazin-1-yl)-4-oxo-4H-chromene-2-carboxylic acid (4-cyanomethyl-phenyl)-amide;

8-(4-Methyl-piperazin-1-yl)-4-oxo-4H-chromene-2-carboxylic acid (1H-indol-5-yl)-amide;

8-(4-Methyl-piperazin-1-yl)-4-oxo-4H-chromene-2-carboxylic acid [4-(1-morpholin-4-yl-methanoyl)-phenyl]-amide;

8-(4-Methyl-piperazin-1-yl)-4-oxo-4H-chromene-2-carboxylic acid [4-(2,6-dimethyl-morpholin-4-yl)-phenyl]-amide;

8-(4-Methyl-piperazin-1-yl)-4-oxo-4H-chromene-2-carboxylic acid [4-(4-fluoro-phenoxy)-phenyl]-amide;

8-(4-Methyl-piperazin-1-yl)-2-(6-morpholin-4-yl-benzooxazol-2-yl)-chromen-4-one;

8-(4-Methyl-piperazin-1-yl)-4-oxo-4H-chromene-2-carboxylic acid (2-hydroxy-4-morpholin-4-yl-phenyl)-amide;

8-(4-Methyl-piperazin-1-yl)-4-oxo-4H-chromene-2-carboxylic acid (5-ethoxy-benzothiazol-2-yl)-amide;

8-(4-Methyl-piperazin-1-yl)-4-oxo-4H-chromene-2-carboxylic acid (4-bromo-phenyl)-amide;

8-(4-Methylpiperazin-1-yl)-4-oxo-4H-chromene-2-carboxylic acid methyl-(4-morpholin-4-yl-phenyl)-amide;

8-(4-Methyl-piperazin-1-yl)-4-oxo-4H-chromene-2-carboxylic acid (3-morpholin-4-yl-phenyl)-amide;

8-(4-Methyl-piperazin-1-yl)-4-oxo-4H-chromene-2-carboxylic acid (3-cyano-4-morpholin-4-yl-phenyl)-amide;

8-(4-Methyl-piperazin-1-yl)-4-oxo-4H-chromene-2-carboxylic acid (3-fluoro-4-morpholin-4-yl-phenyl)-amide;

4-[4-({1-[8-(4-Methyl-piperazin-1-yl)-4-oxo-4H-chromen-2-yl]-methanoyl}-amino)-phenyl]-piperazine-1-carboxylic acid tert-butyl ester;

8-(4-Methyl-piperazin-1-yl)-4-oxo-4H-chromene-2-carboxylic acid (4-piperazin-1-yl-phenyl)-amide;

6-Methoxy-8-(4-methyl-piperazin-1-yl)-4-oxo-4H-chromene-2-carboxylic acid (4-morpholin-4-yl-phenyl)-amide;

6-Methoxy-8-(4-methyl-piperazin-1-yl)-4-oxo-4H-chromene-2-carboxylic acid [4-(4-methanesulfonyl-piperazin-1-yl)-phenyl]-amide;

6-Methoxy-8-(4-Methyl-piperazin-1-yl)-4-oxo-4H-chromene-2-carboxylic acid (3-chloro-4-morpholin-4-yl-phenyl)-amide;

6-Methoxy-8-(4-methyl-piperazin-1-yl)-4-oxo-4H-chromene-2-carboxylic acid (3-fluoro-4-morpholin-4-yl-phenyl)-amide;

6-Methoxy-8-(4-methyl-piperazin-1-yl)-4-oxo-4H-chromene-2-carboxylic acid (2-methoxy-4-morpholin-4-yl-phenyl)-amide;

6-Methoxy-8-(4-methyl-piperazin-1-yl)-4-oxo-4H-chromene-2-carboxylic acid (4-thiomorpholin-4-yl-phenyl)-amide;

6-Methoxy-8-(4-methyl-piperazin-1-yl)-4-oxo-4H-chromene-2-carboxylic acid [4-(2,6-dimethyl-morpholin-4-yl)-phenyl]-amide;

6-Methoxy-8-(4-methyl-piperazin-1-yl)-4-oxo-4H-chromene-2-carboxylic acid (3-morpholin-4-yl-phenyl)-amide;

6-Methoxy-8-(4-methyl-piperazin-1-yl)-4-oxo-4H-chromene-2-carboxylic acid {4-[4-(2-hydroxy-ethyl)piperazin-1-yl]-phenyl}-amide;

6-Methoxy-8-(4-methyl-piperazin-1-yl)-4-oxo-4H-chromene-2-carboxylic acid [4-(1-morpholin-4-yl-methanoyl)-phenyl]-amide;

6-Methoxy-8-(4-methyl-piperazin-1-yl)-4-oxo-4H-chromene-2-carboxylic acid (3-cyano-4-morpholin-4-yl-phenyl)-amide;

4-[4-({1-[6-Methoxy-8-(4-methyl-piperazin-1-yl)-4-oxo-4H-chromen-2-yl]-methanoyl}-amino)-phenyl]-piperazine-1-carboxylic acid tert-butyl ester;

6-Methoxy-8-(4-methyl-piperazin-1-yl)-4-oxo-4H-chromene-2-carboxylic acid (4-piperazin-1-yl-phenyl)-amide;

6-Methoxy-8-(4-methyl-piperazin-1-yl)-4-oxo-4H-chromene-2-carboxylic acid [4-(4-propionyl-piperazin-1-yl)-phenyl]-amide;

6-Methoxy-8-(4-methyl-piperazin-1-yl)-4-oxo-4H-chromene-2-carboxylic acid [4-(4-ethane sulfonyl-piperazin-1-yl)-phenyl]-amide;

6-Methoxy-8-(4-methyl-piperazin-1-yl)-4-oxo-4H-chromene-2-carboxylic acid [4-(4-dimethyl sulfamoyl-piperazin-1-yl)-phenyl]-amide;

4-[4-({1-[6-Methoxy-8-(4-methyl-piperazin-1-yl)-4-oxo-4H-chromen-2-yl]-methanoyl}-amino)-phenyl]-piperazine-1-carboxylic acid dimethylamide;

4-[4-({1-[6-Methoxy-8-(4-methyl-piperazin-1-yl)-4-oxo-4H-chromen-2-yl]-methanoyl}-amino)-phenyl]-piperazine-1-carboxylic acid ethylamide;

4-[4-({1-[6-Methoxy-8-(4-methyl-piperazin-1-yl)-4-oxo-4H-chromen-2-yl]-methanoyl}-amino)-phenyl]-piperazine-1-carboxylic acid cyclohexylamide;

4-[4-({1-[6-Methoxy-8-(4-methyl-piperazin-1-yl)-4-oxo-4H-chromen-2-yl]-methanoyl}-amino)-phenyl]-piperazine-1-carboxylic acid cyclopentylamide;

6-Methoxy-8-(4-methyl-piperazin-1-yl)-4-oxo-4H-chromene-2-carboxylic acid {4-[4-(1-pyrrolidin-1-yl-methanoyl)-piperazin-1-yl]-phenyl}-amide;

6-Methoxy-8-(4-methyl-piperazin-1-yl)-4-oxo-4H-chromene-2-carboxylic acid {1-[4-(propane-2-sulfonyl)-piperazin-1-yl]-phenyl}-amide;

6-Methoxy-8-(4-methyl-piperazin-1-yl)-4-oxo-4H-chromene-2-carboxylic acid {4-[4-(2-methyl-propanoyl)-piperazin-1-yl]-phenyl}-amide;

6-Methoxy-8-(4-methyl-piperazin-1-yl)-4-oxo-4H-chromene-2-carboxylic acid {4-[4-(1-morpholin-4-yl-methanoyl)-piperazin-1-yl]-phenyl}-amide;

6-Fluoro-8-(4-methyl-piperazin-1-yl)-4-oxo-4H-chromene-2-carboxylic acid (4-morpholin-4-yl-phenyl)-amide;

6-Fluoro-8-(4-methyl-piperazin-1-yl)-4-oxo-4H-chromene-2-carboxylic acid [4-(4-methanesulfonyl-piperazin-1-yl)phenyl]-amide;

6-Fluoro-8-(4-methyl-piperazin-1-yl)-4-oxo-4H-chromene-2-carboxylic acid [4-(4-acetyl-piperazin-1-yl)-phenyl]-amide;

6-Fluoro-8-(4-methyl-piperazin-1-yl)-4-oxo-4H-chromene-2-carboxylic acid (3-chloro-4-morpholin-4-yl-phenyl)-amide;

6-Fluoro-8-(4-methyl-piperazin-1-yl)-4-oxo-4H-chromene-2-carboxylic acid (3-fluoro-4-morpholin-4-yl-phenyl)-amide;

6-Fluoro-8-(4-methyl-piperazin-1-yl)-4-oxo-4H-chromene-2-carboxylic acid (3-cyano-4-morpholin-4-yl-phenyl)-amide;

6-Fluoro-8-(4-methyl-piperazin-1-yl)-4-oxo-4H-chromene-2-carboxylic acid [4-(1-morpholin-4-yl-methanoyl)-phenyl]-amide;

6-Methyl-8-(4-methyl-piperazin-1-yl)-4-oxo-4H-chromene-2-carboxylic acid (4-morpholin-4-yl-phenyl)-amide;

6-Methyl-8-(4-methyl-piperazin-1-yl)-4-oxo-4H-chromene-2-carboxylic acid [4-(1-morpholin-4-yl-methanoyl)-phenyl]-amide;

6-Methyl-8-(4-methyl-piperazin-1-yl)-4-oxo-4H-chromene-2-carboxylic acid (3-fluoro-4-morpholin-4-yl-phenyl)-amide;

6-Chloro-8-(4-methyl-piperazin-1-yl)-4-oxo-4H-chromene-2-carboxylic acid (4-morpholin-4-yl-phenyl)-amide;

5-Methyl-8-(4-methyl-piperazin-1-yl)-4-oxo-4H-chromene-2-carboxylic acid (4-morpholin-4-yl-phenyl)-amide;

5-Methoxy-8-(4-methyl-piperazin-1-yl)-4-oxo-4H-chromene-2-carboxylic acid (4-morpholin-4-yl-phenyl)-amide;

6-Methoxy-8-(4-methyl-piperazin-1-yl)-4-oxo-4H-chromene-2-carboxylic acid {4-[4-(3-hydroxy-propanoyl)-piperazin-1-yl]-phenyl}-amide;

4-[4-({1-[6-Fluoro-8-(4-methyl-piperazin-1-yl)-4-oxo-4H-chromen-2-yl]-methanoyl}-amino)-phenyl]-piperazine-1-carboxylic acid tert-butyl ester;

4-[4-({1-[6-Fluoro-8-(4-methyl-piperazin-1-yl)-4-oxo-4H-chromene-2-carboxylic acid (4-piperazin-1-yl-phenyl)-amide;

6-Fluoro-8-(4-methyl-piperazin-1-yl)-4-oxo-4H-chromene-2-carboxylic acid [4-(4-ethane sulfonyl-piperazin-1-yl)-phenyl]-amide;

6-Fluoro-8-(4-methyl-piperazin-1-yl)-4-oxo-4H-chromene-2-carboxylic acid [4-(4-propionyl-piperazin-1-yl)-phenyl]-amide; and 6-Fluoro-8-(4-methyl-piperazin-1-yl)-4-oxo-4H-chromene-2-carboxylic acid {4-[4-(3-hydroxy-propanoyl)-piperazin-1-yl]-phenyl}-amide;

or a pharmaceutically acceptable salt thereof 4-[4-({1-[6-Fluoro-8-(4-methyl-piperazin-1-yl)-4-oxo-4H-chromen-2-yl]-methanoyl}-amino)-phenyl]-piperazine-1-carboxylic acid ethylamide;

6-Methoxy-8-(4-methyl-[1,4]diazepan-1-yl)-4-oxo-4H-chromene-2-carboxylic acid (4-morpholin-4-yl-phenyl)-amide;

6-Ethoxy-8-(4-methyl-piperazin-1-yl)-4-oxo-4H-chromene-2-carboxylic acid (4-morpholin-4-yl-phenyl)-amide;

6-Ethoxy-8-(4-methyl-piperazin-1-yl)-4-oxo-4H-chromene-2-carboxylic acid [4-(4-propionyl-piperazin-1-yl)-phenyl]-amide;

6-Methoxy-4-oxo-8-piperazin-1-yl)-4-oxo-4H-chromene-2-carboxylic acid (4-morpholin-4-yl-phenyl)-amide;

6-Hydroxy-8-(4-methyl-piperazin-1-yl)-4-oxo-4H-chromene-2-carboxylic acid (4-morpholin-4-yl-phenyl)-amide;

6-Methoxy-8-(4-methyl-[1,4]diazepan-1-yl)-4-oxo-1,4-dihydro-quinoline-2-carboxylic acid (4-morpholin-4-yl-phenyl)-amide;

6-Fluoro-4-oxo-8-piperazin-1-yl-4H-chromene-2-carboxylic acid (4-morpholin-4-yl-phenyl)-amide.

2. A compound selected from: 8-(4-methyl-1-piperazinyl)-N-[4-(4-morpholinyl)phenyl]-4-oxo-4H-chromene-2-carboxamide;

6-Methoxy-8-(4-methyl-piperazin-1-yl)-4-oxo-4H-chromene-2-carboxylic acid (4-morpholin-4-yl-phenyl)-amide;

6-Methoxy-8-(4-methyl-piperazin-1-yl)-4-oxo-4H-chromene-2-carboxylic acid [4-(4-propionyl-piperazin-1-yl)-phenyl]-amide;

6-Methoxy-8-(4-methyl-piperazin-1-yl)-4-oxo-4H-chromene-2-carboxylic acid [4-(4-ethanesulfonyl-piperazin-1-yl)-phenyl]-amide;

6-Fluoro-8-(4-methyl-piperazin-1-yl)-4-oxo-4H-chromene-2-carboxylic acid [4-(4-acetyl-piperazin-1-yl)phenyl]-amide;

6-Fluoro-8-(4-methyl-piperazin-1-yl)-4-oxo-4H-chromene-2-carboxylic acid [4-(4-ethanesulfonyl-piperazin-1-yl)-phenyl]-amide; and 6-Fluoro-8-(4-methyl-piperazin-1-yl)-4-oxo-4H-chromene-2-carboxylic acid [4-(4-propionyl-perazin-1-yl)-phenyl]-amide;

or a pharmaceutically acceptable salt thereof.

3. 8-(4-methyl-1-piperazinyl)-N-[4-(4-morpholinyl)phenyl]-4-oxo-4H-chromene-2-carboxamide; or a pharmaceutically acceptable salt thereof.

4. 6-Methoxy-8-(4-methyl-piperazin-1-yl)-4-oxo-4H-chromene-2-carboxylic acid (4-morpholin-4-yl-phenyl)-amide; or a pharmaceutically acceptable salt thereof.

5. 6-Methoxy-8-(4-methyl-piperazin-1-yl)-4-oxo-4H-chromene-2-carboxylic acid [4-(4-propionyl-piperazin-1-yl)-phenyl]-amide; or a pharmaceutically acceptable salt thereof.

6. 6-Methoxy-8-(4-methyl-piperazin-1-yl)-4-oxo-4H-chromene-2-carboxylic acid [4-(4-ethane sulfonyl-piperazin-1-yl)-phenyl]-amide; or a pharmaceutically acceptable salt thereof.

7. 6-Fluoro-8-(4-methyl-piperazin-1-yl)-4-oxo-4H-chromene-2-carboxylic acid [4-(4-acetyl-piperazin-1-yl)-phenyl]-amide; or a pharmaceutically acceptable salt thereof.

8. 6-Fluoro-8-(4-methyl-piperazin-1-yl)-4-oxo-4H-chromene-2-carboxylic acid [4-(4-ethanesulfonyl-piperazin-1-yl)-phenyl]-amide; or a pharmaceutically acceptable salt thereof.

9. 6-Fluoro-8-(4-methyl-piperazin-1-yl)-4-oxo-4H-chromene-2-carboxylic acid [4-(4-propionyl-piperazin-1-yl)-phenyl]-amide; or a pharmaceutically acceptable salt thereof.

* * * * *